(12) United States Patent
Westfall et al.

(10) Patent No.: US 11,992,510 B2
(45) Date of Patent: May 28, 2024

(54) PROBIOTIC FORMULATIONS FOR THE TREATMENT AND ALLEVIATION OF METABOLIC AND OXIDATIVE STRESS, INFLAMMATION AND NEURODEGENERATION

(71) Applicant: PROVIVA PHARMA INC., Montreal (CA)

(72) Inventors: Susan Westfall, Montreal (CA); Satya Prakash, Montreal (CA)

(73) Assignee: Proviva Pharma Inc., Montreal (CA)

( * ) Notice: Subject to any disclaimer, the term of this patent is extended or adjusted under 35 U.S.C. 154(b) by 194 days.

(21) Appl. No.: 16/969,759

(22) PCT Filed: Feb. 12, 2019

(86) PCT No.: PCT/CA2019/000018
§ 371 (c)(1),
(2) Date: Aug. 13, 2020

(87) PCT Pub. No.: WO2019/157585
PCT Pub. Date: Aug. 22, 2019

(65) Prior Publication Data
US 2020/0405786 A1 Dec. 31, 2020

Related U.S. Application Data

(60) Provisional application No. 62/629,832, filed on Feb. 13, 2018.

(51) Int. Cl.
*A61K 35/747* (2015.01)
*A23L 33/135* (2016.01)
(Continued)

(52) U.S. Cl.
CPC .......... *A61K 35/745* (2013.01); *A23L 33/135* (2016.08); *A61K 35/747* (2013.01); *A61K 2035/115* (2013.01)

(58) Field of Classification Search
None
See application file for complete search history.

(56) References Cited

PUBLICATIONS

Xie et al. Diabetes Obes. Metab. 13(4): 289-301, 2011, Abstract.*
(Continued)

*Primary Examiner* — S. Devi

(57) ABSTRACT

In alternative embodiments, provided are probiotic formulations, including compositions, formulations, products of manufacture and kits comprising them, and methods of using them, for the treatment and alleviation of metabolic and oxidative stress, inflammation and neurodegeneration. In alternative embodiments, probiotic formulations as provided herein comprise or consist of any combination of the three probiotic strains: *Lactobacillus fermentum* NCIMB 5221, *Lactobacillus plantarum* NCIMB 8826 and *Bifidobacteria longum* spp. *infantis* NCIMB 702255. In alternative embodiments, probiotic formulations as provided herein are combined with a triphala. In alternative embodiments, probiotic formulations as provided herein are used for: the treatment of metabolic conditions such as diabetes and obesity, inflammatory conditions such as IBD, IBS, arthritis; and, neurodegenerative diseases such as Alzheimer's disease and Parkinson's disease. In alternative embodiments, probiotic formulations as provided herein are used for: resisting oxidative stress, reducing inflammation, lowering blood and total glucose levels, lowering triglycerides levels and managing insulin resistance.

24 Claims, 36 Drawing Sheets

Specification includes a Sequence Listing.

(51) Int. Cl.
A61K 35/00 (2006.01)
A61K 35/745 (2015.01)

(56) References Cited

PUBLICATIONS

Pavan et al. Clin. Diag. Lab. Immunol. 10: 696-701, 2003.*
Peterson et al. J. Alternat. Complement. Med. 23: 607-614, 2017.*
Formulab Chow 5008 & Formulab Chow, Irradiated 5008C33, LabChows, Purina, 1 page, Dec. 11, 2009.*
Westfall, S. et al., "Ferulic Acid Produced by Lactobacillus fermentum NCIBM 5221 Reduces Symptoms of Metabolic Syndrome in *Drosophila melanogaster*", Journal of Microbial and Biochemical Technology, 2016, v. 8(4), pp. 272-284.
Tomaro-Duchesneau, C. et al., "Effect of orally administered L. fermentum NCIMB 5521 on markers of metabolic syndrome: an in vivo analysis using ZDF rats", Appl Microbiol Biotechnol, 2014, v. 98, pp. 115-126.
Tomaro-Duchesneau, C. et al., "Probiotic Ferulic Acid Esterase Active Lactobacillus fermentum NCIMB 5221 APA Microcapsules for Oral Delivery: Preparation and In Vitro Characterization", 2012, Pharmaceuticals, v. 5, pp. 236-248.
Rathore, S. et al., "Production of potentially probiotic beverages using single and mixed cereal substrates fermented with lactic acid bacteria cultures", 2012, Food Microbiology, v. 30, pp. 239-244.
Charteris et al., "Edible table (bio)spread containing potentially probiotic *Lactobacillus* and *Bifidobacterium* species, 2002, International Journal of Dairy Technology", v. 55(1), pp. 44-56.
Westfall, S. et al., "A novel polyphenolic prebiotic and probiotic formulation have synergistic effects on the gut microbiota influencing *Drosophila melanogaster* physiology", Artificial Cells, Nanomedicine, and Biotechnology, Apr. 12, 2018, v. 46, No. S2, pp. S441-S455.
Westfall, S. et al., "Longevity extension in *Drosophila* through gut-brain communication", Scientific Reports, Nature, May 30, 2018, v. 8:8362, pp. 1-15.
Westfall, S. et al., "A polyphenol-rich prebiotic in combination with a novel probiotic formulation alleviates markers of obesity and diabetes in *Drosophila*, Journal of Functional Foods", Sep. 1, 2018, v. 48, pp. 374-386.
International Search Report, International Application No. PCT/CA2019/000018, dated Jun. 5, 2019.

* cited by examiner

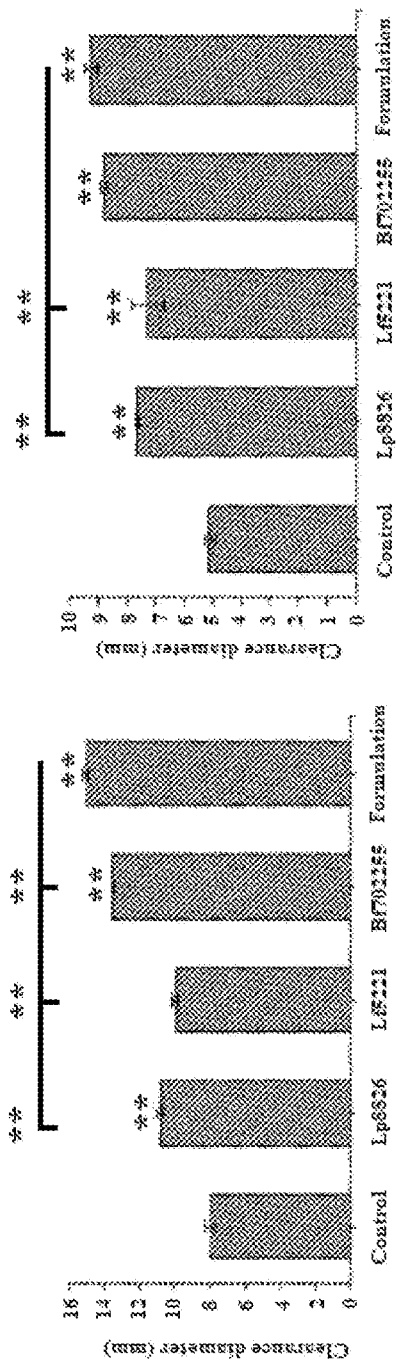
FIG. 2C
FIG. 2E
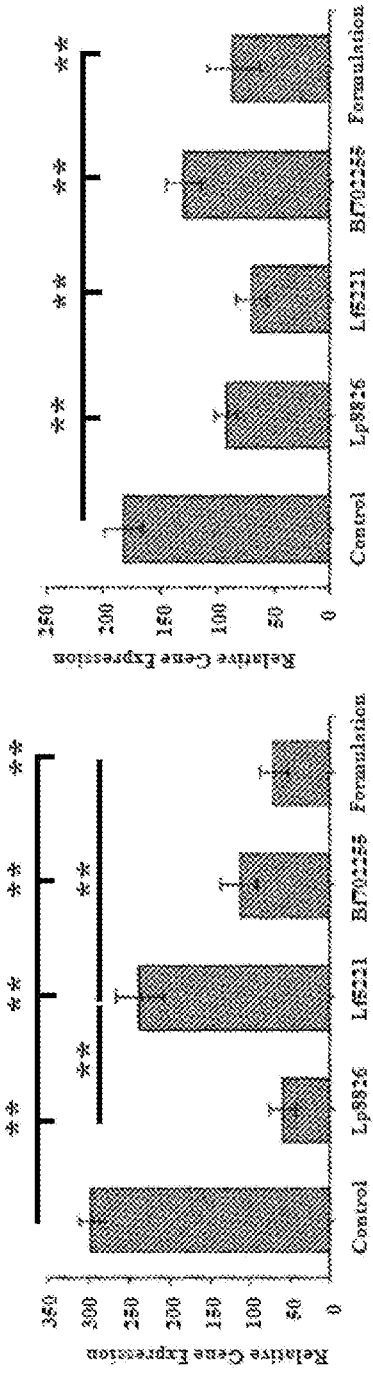
FIG. 2D
FIG. 2F

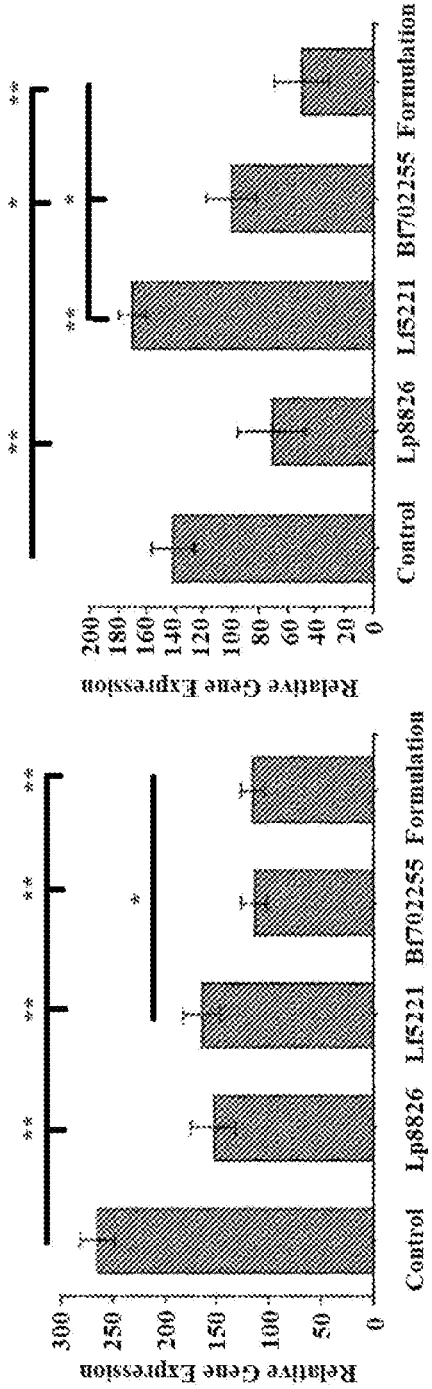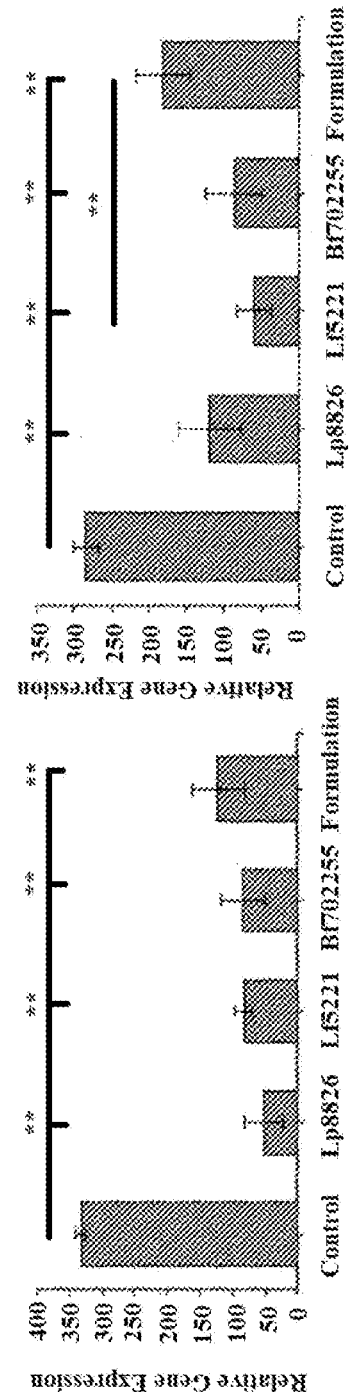

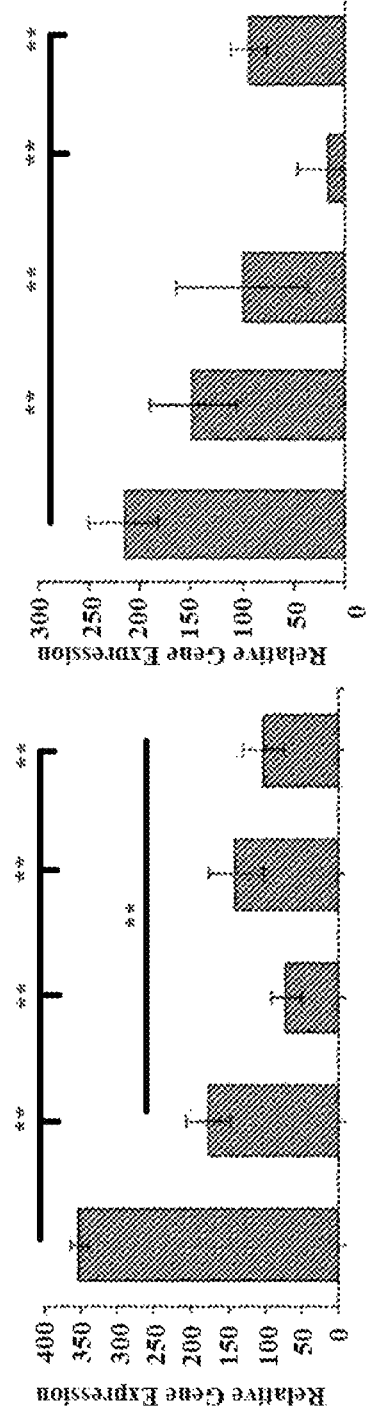
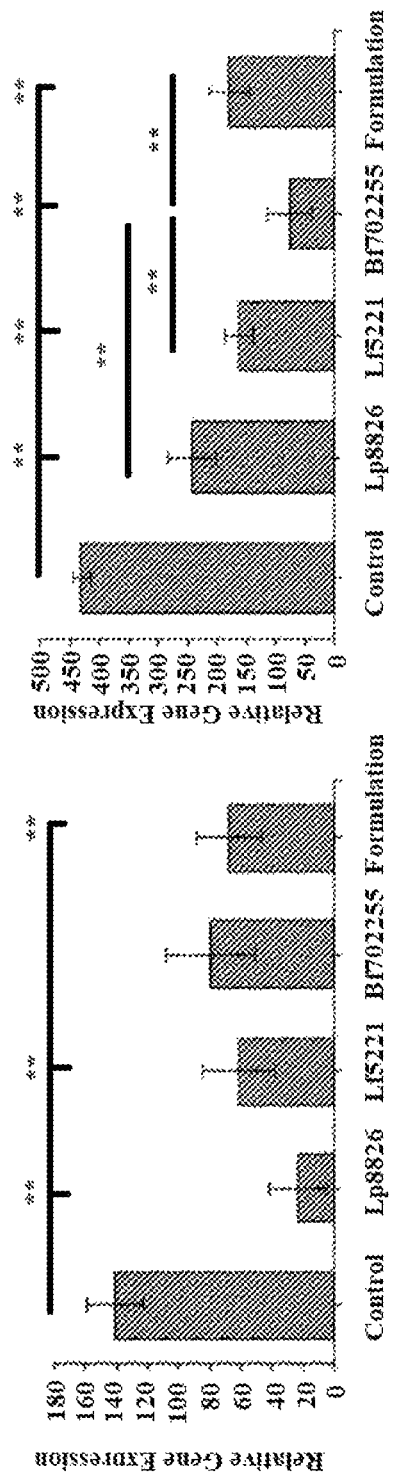
FIG. 2K
FIG. 2L
FIG. 2M
FIG. 2N

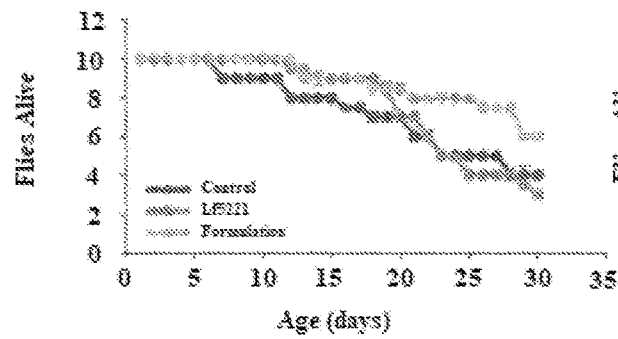
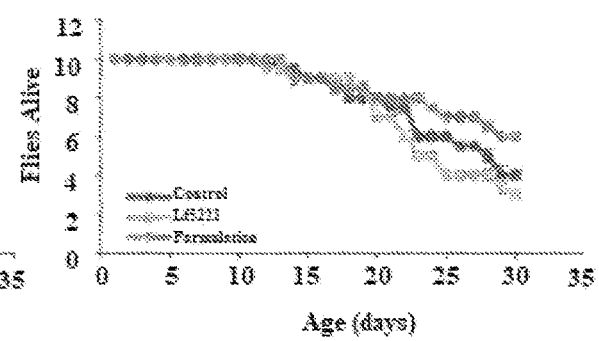
FIG. 4A  FIG. 4B
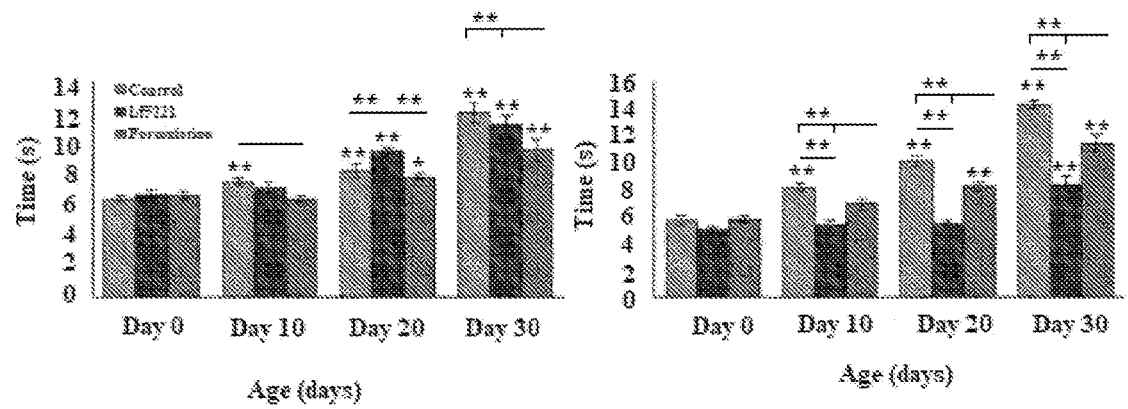
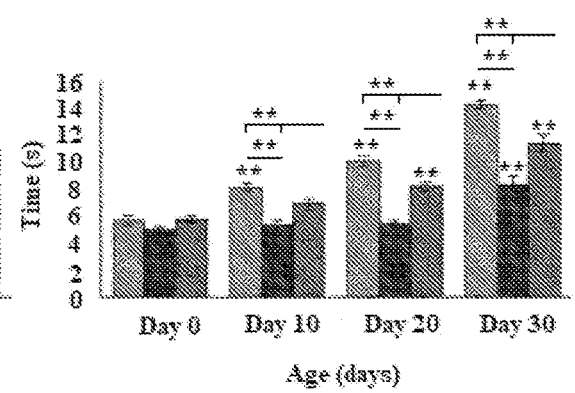
FIG. 4C  FIG. 4D

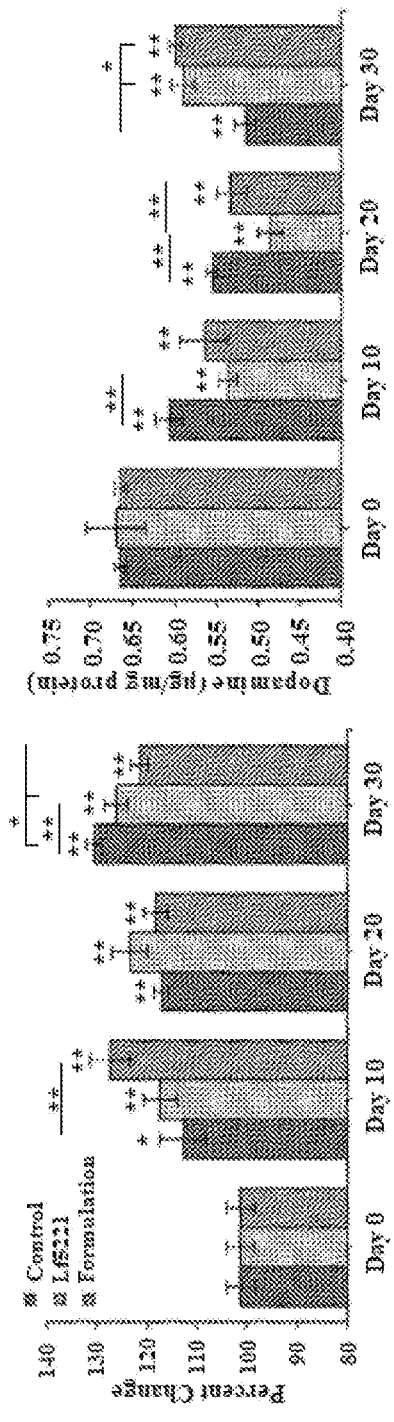
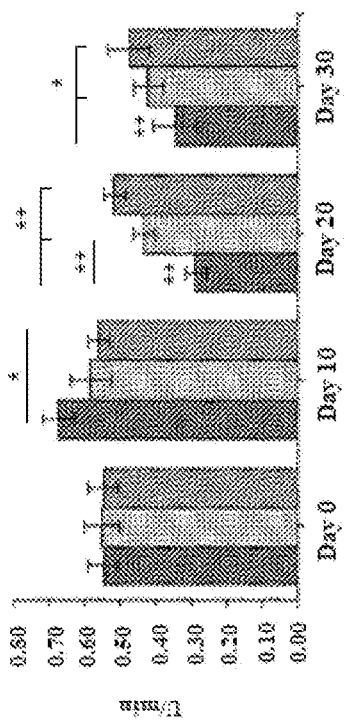
FIG. 4E
FIG. 4F
FIG. 4G

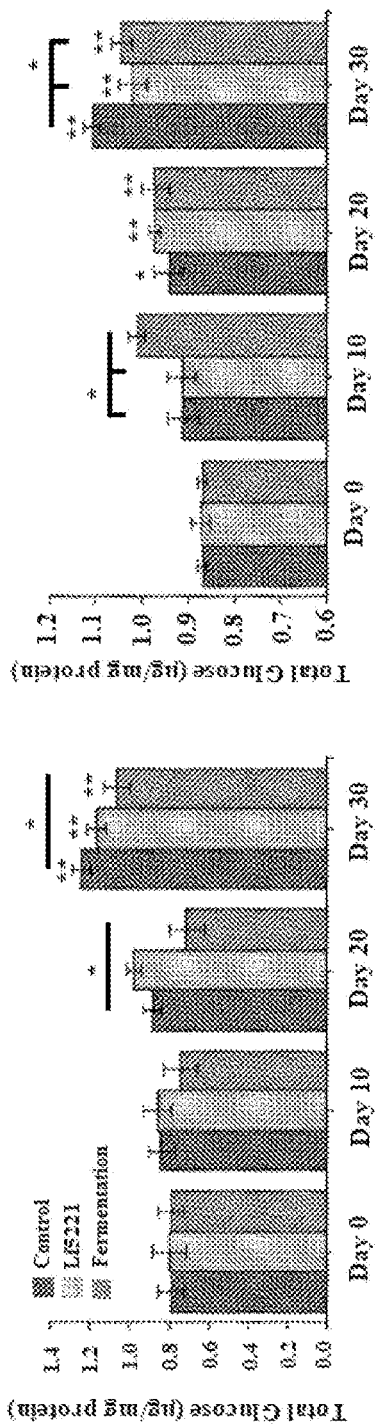
FIG. 4H
FIG. 4I
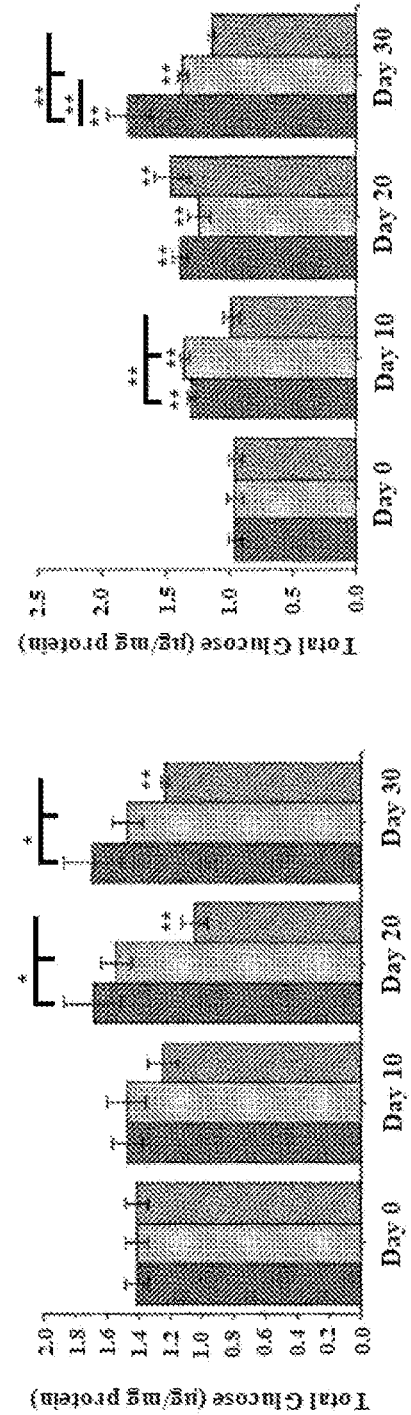
FIG. 4J
FIG. 4K

PROBIOTIC FORMULATIONS FOR THE TREATMENT AND ALLEVIATION OF METABOLIC AND OXIDATIVE STRESS, INFLAMMATION AND NEURODEGENERATION

CROSS REFERENCE TO RELATED APPLICATIONS

This application is a 371 National Phase application of International Application No. PCT/CA2019/000018 filed on Feb. 12, 2019 and claiming priority from U.S. Ser. No. 62/629,832 filed on Feb. 13, 2018, each of the entire contents of which are hereby incorporated by reference.

INCORPORATION-BY-REFERENCE OF SEQUENCE LISTING OR TABLE

The material in the accompanying sequence listing is hereby incorporated by reference in its entirety into this specification. The accompanying file, titled SEQUENCE LISTING.txt in ASCII format was created on Feb. 13, 2018 and is 13 kilobytes in size.

TECHNICAL FIELD

This invention generally relates to microbiology and probiotics. In alternative embodiments, provided are probiotic formulations, including compositions, products of manufacture and kits comprising them, and methods of using them, for the treatment and alleviation of metabolic and oxidative stress, inflammation and neurodegeneration. In alternative embodiments, probiotic formulations as provided herein consist of any combination of the three probiotic strains: *Lactobacillus fermentum* NCIMB S221, *Lactobacillus plantarum* NCIMB 8826 and *Bifidobacteria longum* spp. *infantis* NCIMB 702255. In alternative embodiments, probiotic formulations as provided herein are used for: the treatment of metabolic conditions such as diabetes and obesity, inflammatory conditions such as IBD, IBS, arthritis; and, neurodegenerative diseases such as Alzheimer's disease and Parkinson's disease. In alternative embodiments, probiotic formulations as provided herein are used for: resisting oxidative stress, reducing inflammation, lowering blood and total glucose levels, lowering triglycerides levels and managing insulin resistance.

BACKGROUND

The gut microbiota consists of a plethora of thousands of bacterial species residing synbiotically within the gastrointestinal tract (GIT). The co-evolution of the gut microbiota with the human host has made the activities and interaction of the gut microbiota indispensable for digestive health, gut motility, vitamin synthesis, mineral absorption, immune and neurological development, energy homeostasis and metabolic health. Imbalances in the gut microbiota (dysbiosis) caused by poor diet, antibiotic use and normal aging contributes to chronic diseases including metabolic syndrome, depression, osteoporosis and neurodegeneration. Modulation of the microbiota with beneficial bacterial species (probiotics) and flora-promoting indigestible carbohydrates (prebiotics) reverses dysbiosis and promotes an anti-inflammatory and anti-oxidative environment while positively regulating the immune system and energy homeostasis.

SUMMARY

In alternative embodiments, provided are products of manufacture, compositions, formulations, pharmaceutical compositions or kits comprising one or more probiotics comprising or consisting of: any combination of: *Lactobacillus fermentum* NCIMB 5221, *Lactobacillus plantarum* NCIMB 8826 and *Bifidobacteria longum* spp. *infantis* NCIMB 702255.

In alternative embodiments, the products of manufacture, compositions, formulations, pharmaceutical compositions or kits further comprise a prebiotic composition, wherein optionally the prebiotic composition comprises or consists of: a triphala, or any herbal rasayana formula, optionally an herbal rasayana formula comprising three myrobalans, or an herbal rasayana formula consisting of relatively equal parts of three myrobalans, optionally taken without seed, wherein optionally the three myrobalans are amalaki (*Emblica officinalis*), bibhitaki (*Terminalia bellirica*), and haritaki (*Terminalia chebula*), and optionally the triphala or the herbal rasayana—comprising formulation or pharmaceutical composition is an aqueous or water-based formulation, and optionally between about 0.5% and 50%, 1.0% and 40%, 5.0% and 30% or 10.0% and 25% of the product of manufacture, composition, formulation, pharmaceutical composition or kit is the triphala or the herbal rasayana.

In alternative embodiments, the products of manufacture, compositions, formulations, pharmaceutical compositions or kits, also comprise or further comprise:
  *Lactobacillus fermentum* NCIMB 5221,
  *Lactobacillus plantarum* NCIMB 8826,
  *Bifidobacteria longum* spp. *infantis* NCIMB 702255,
  *Lactobacillus fermentum* NCIMB 5221 and *Lactobacillus plantarum* NCIMB 8826,
  *Lactobacillus plantarum* NCIMB 8826 and *Bifidobacteria longum* spp. *infantis* NCIMB 702255,
  *Lactobacillus fermentum* NCIMB 5221, and *Bifidobacteria longum* spp. *infantis* NCIMB 702255, or
  *Lactobacillus fermentum* NCIMB 5221, *Lactobacillus plantarum* NCIMB 8826 and *Bifidobacteria longum* spp. *infantis* NCIMB 702255.

In alternative embodiments, active probiotic in the product of manufacture, composition, formulation, pharmaceutical composition or kit comprises, or consists of:
  *Lactobacillus fermentum* NCIMB 5221,
  *Lactobacillus plantarum* NCIMB 8826,
  *Bifidobacteria longum* spp. *infantis* NCIMB 702255,
  *Lactobacillus fermentum* NCIMB 5221 and *Lactobacillus plantarum* NCIMB 8826,
  *Lactobacillus plantarum* NCIMB 8826 and *Bifidobacteria longum* spp. *infantis* NCIMB 702255,
  *Lactobacillus fermentum* NCIMB 5221, and *Bifidobacteria longum* spp. *infantis* NCIMB 702255, or
  *Lactobacillus fermentum* NCIMB 5221, *Lactobacillus plantarum* NCIMB 8826 and *Bifidobacteria longum* spp. *infantis* NCIMB 702255.

In alternative embodiments, one, several or all of the probiotics are alive or dead. In alternative embodiments, the probiotics are:
  (a) present in relatively equal proportions;
  (b) a total of between about 10 s CFU/ml to 1011 CFU/ml, or between about $10^5$ CFU/gm to between about $3.0 \times 10^{11}$ CFU/gm,
  (b) a total of about $3.0 \times 10^9$ CFU/ml or about $3.0 \times 10^9$ CFU/gm, optionally with the relative proportions:
    *Lactobacillus fermentum* NCIMB 5221 (Lf5221) at about $1.0 \times 10^9$ CFU/ml,
    *Lactobacillus plantarum* NCIMB 8826 (Lp8826) at about $1.0 \times 10^9$ CFU/ml, and
    *Bifidobacteria longum* spp. *infantis* NCIMB 702255 (Bi702255) at about $1.0 \times 10^9$ CFU/ml.

In alternative embodiments, the products of manufacture, compositions, formulations, pharmaceutical compositions or kits, are manufactured or formulated in the form of a solution, a suspension, an emulsion, a powder, a lozenge, a pill, a syrup, a tablet, a capsule, a geltab, an aerosol, a suppository, a chewing gum, a capsule, a sachet or any equivalent thereof.

In alternative embodiments, the products of manufacture, compositions, formulations, pharmaceutical compositions or kits, are manufactured or formulated as an edible material, drink or foodstuff, optionally as a (or comprising a) water, a fluid or solid dairy product, a milk, a condensed milk, a drinkable yogurt, a yogurt, a fermented beverage, an ice cream, a cheese, a soy milk, a vegetable juice, a fruit juice, a sports drink, a dessert, a jelly, a candy, a baby food, a health food, a dietary supplement or an additive or any equivalent thereof.

In alternative embodiments, the products of manufacture, compositions, formulations, pharmaceutical compositions or kits, are manufactured or formulated to have a unit dosage of:
(a) total between about $10^5$ CFU/ml to about $10^{11}$ CFU/ml, or between about $10^5$ CFU/gm to between about $3.0 \times 10^{11}$ CFU/gm; or
(c) a total of about $3.0 \times 10^9$ CFU/ml or about $3.0 \times 10^9$ CFU/gm, optionally with the relative proportions:
Lactobacillus fermentum NCIMB 5221 (Lf5221) at about $1.0 \times 10^9$ CFU/ml,
Lactobacillus plantarum NCIMB 8826 (Lp8826) at about $1.0 \times 10^9$ CFU/ml, and
Bifidobacteria longum spp. infantis NCIMB 702255 (Bi702255) at about $1.0 \times 10^9$ CFU/ml.

In alternative embodiments, provided are methods for:
(a) the treatment, amelioration, prevention and/or alleviation of (e.g., reducing the symptoms of), or slowing the onset or progress of, metabolic and oxidative stress, inflammation, aging and/or neurodegeneration, or for enhancing longevity, in an individual in need thereof,
(b) the treatment, amelioration, prevention and/or alleviation of (e.g., reducing the symptoms of), or slowing the onset or progress of: metabolic conditions such as diabetes and obesity, inflammatory conditions such as Inflammatory Bowel Disease (IBD) and Irritable Bowel Syndrome (IBS); arthritis; neurodegenerative diseases such as Alzheimer's disease and Parkinson's disease; oxidative stress, including resisting oxidative stress; and/or inflammation, including reducing inflammation, in an individual in need thereof, or
(c) lowering blood and total glucose levels, lowering triglycerides levels and managing insulin resistance, in an individual in need thereof,
comprising administering to an individual in need thereof a product of manufacture, composition, formulation, pharmaceutical composition or kit as provided herein, wherein optionally the individual is a human or an animal, and optionally between about one to four dosages, or unit dosages, of the product of manufacture, composition, formulation or pharmaceutical composition are administered to the individual each day, and optionally the unit dosage is reduced, optionally reduced by between about 10% to 90%, for pediatric uses.

In alternative embodiments, provided are uses of a product of manufacture, composition, formulation, pharmaceutical composition or kit as provided herein, for:
(a) the treatment, amelioration, prevention and/or alleviation of (e.g., reducing the symptoms of), or slowing the onset or progress of, metabolic and oxidative stress, inflammation, aging and/or neurodegeneration, or for enhancing longevity, in an individual in need thereof,
(b) the treatment, amelioration, prevention and/or alleviation of (e.g., reducing the symptoms of), or slowing the onset or progress of: metabolic conditions such as diabetes and obesity, inflammatory conditions such as Inflammatory Bowel Disease (IBD) and Irritable Bowel Syndrome (IBS); arthritis; neurodegenerative diseases such as Alzheimer's disease and Parkinson's disease; oxidative stress, including resisting oxidative stress; and/or inflammation, including reducing inflammation, in an individual in need thereof, or
(c) lowering blood and total glucose levels, lowering triglycerides levels and managing insulin resistance, in an individual in need thereof,
comprising administering to an individual in need thereof a product of manufacture, composition, formulation, pharmaceutical composition or kit as provided herein, wherein optionally the individual is a human or an animal, and optionally between about one to four dosages, or unit dosages, of the product of manufacture, composition, formulation or pharmaceutical composition are administered to the individual each day, and optionally the unit dosage is reduced, optionally reduced by between about 10% to 90%, for pediatric uses.

In alternative embodiments, provided are products of manufacture, compositions, formulations, pharmaceutical compositions or kits as provided herein, for use in:
(a) the treatment, amelioration, prevention and/or alleviation of (e.g., reducing the symptoms of), or slowing the onset or progress of, metabolic and oxidative stress, inflammation, aging and/or neurodegeneration, or for enhancing longevity, in an individual in need thereof,
(b) the treatment, amelioration, prevention and/or alleviation of (e.g., reducing the symptoms of), or slowing the onset or progress of: metabolic conditions such as diabetes and obesity, inflammatory conditions such as Inflammatory Bowel Disease (IBD) and Irritable Bowel Syndrome (IBS); arthritis; neurodegenerative diseases such as Alzheimer's disease and Parkinson's disease; oxidative stress, including resisting oxidative stress; and or inflammation, including reducing inflammation, in an individual in need thereof, or
(c) lowering blood and total glucose levels, lowering triglycerides levels and managing insulin resistance, in an individual in need thereof,
comprising administering to an individual in need thereof a product of manufacture, composition, formulation, pharmaceutical composition or kit as provided herein, wherein optionally the individual is a human or an animal, and optionally between about one to four dosages, or unit dosages, of the product of manufacture, composition, formulation or pharmaceutical composition are administered to the individual each day, and optionally the unit dosage is reduced, optionally reduced by between about 10% to 90%, for pediatric uses.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIGS. 2A to 2N graphically illustrates data showing the measure of immune activation markers in *Drosophila melanogaster* treated with exemplary probiotics as provided herein and exposed to an acute oral infection:

*Drosophila* pre-treated with individual or an exemplary probiotic formulation as provided herein were placed on media inoculated with either *E. coli* (EC) or *S. aureus* (SA). FIGS. 2A and 2B show survivability of *Drosophila* on various concentrations of *E. coli* (FIG. 2A) and *S. aureus* (FIG. 2B), which are recorded as the time in days when 50% of the *Drosophila* died. FIGS. 2C and 2D show agar diffusion tests, which were conducted with the hemolymph of probiotic-treated *Drosophila* on lawns of both *E. coli* (FIG. 2C) and *S. aureus* (FIG. 2D) and are reported as the size of the zone of inhibition. Gene expression of various inflammatory markers is shown for pretreated *Drosophila* infected with $5.0 \times 10^9$ CFU/ml of either *E. coli* as shown in FIG. 2E, FIG. 2I, FIG. 2F and FIG. 2M) or *S. aureus* (FIG. 2F, FIG. 2J, FIG. 2L and FIG. 2N). Dual oxidase (Duox) (FIG. 2E and FIG. 2F), IMD (FIG. 2G and FIG. 2H), Attacin A (FIG. 2I and FIG. 2J), Diptercin (FIG. 2K and FIG. 2L) and Defensin (FIG. 2M and FIG. 2N) expression are all represented as the percentage change between *Drosophila* reared on the respective probiotic media vs. *Drosophila* with the probiotic treatment and infection with the pathogenic strain. Each group represents n=5 independent samples with significance indicated as black stars (*) between group differences and grey stars (*) relative to the control group with the same probiotic treatment regime. The level of significance is indicated as * $p<0.05$ and ** $p <0.01$.

FIGS. 3A to 2E graphically illustrates data showing the measure of *Drosophila melanogaster* tolerance to an acute oxidative stress challenge after treatment with exemplary probiotics as provided herein:

*Drosophila* were challenged with a 3% hydrogen peroxide acute oxidative stress for 72 h. Levels of (FIG. 3A) survival, (FIG. 3B) total oxidants, (FIG. 3C) superoxide dismutase (SOD) activity, (FIG. 3D) glutathione peroxidase (GPx) activity and (FIG. 3E) lipid peroxidation (LPO) were measured using various biochemical assays. All values are represented as the percentage compared to an unchallenged control treated with the same probiotic regime. Significance is indicated as grey stars () relative to the untreated control and black stars () between groups with * $p<0.05$ and ** $p<0.01$. Each group contains n=5 independent samples.

Figure 4L:
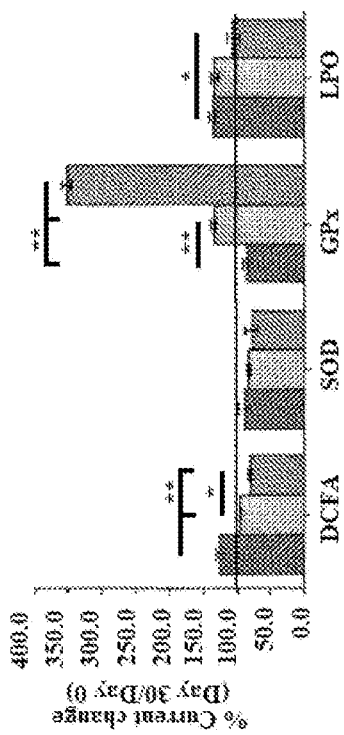
Figure 4M:
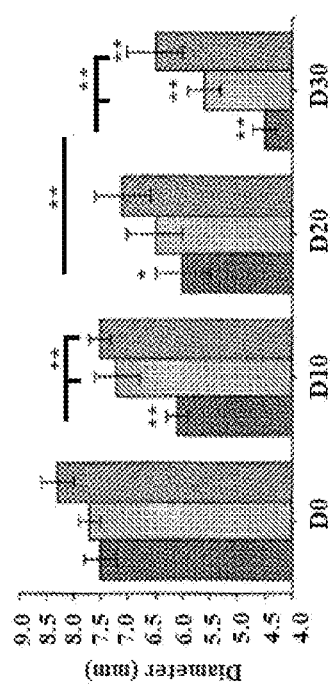
Figure 4N:
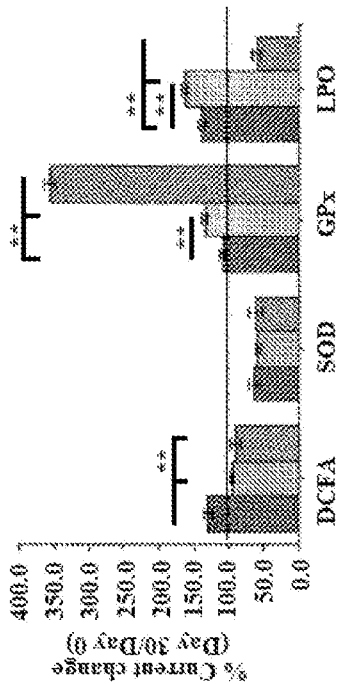
Figure 4O:
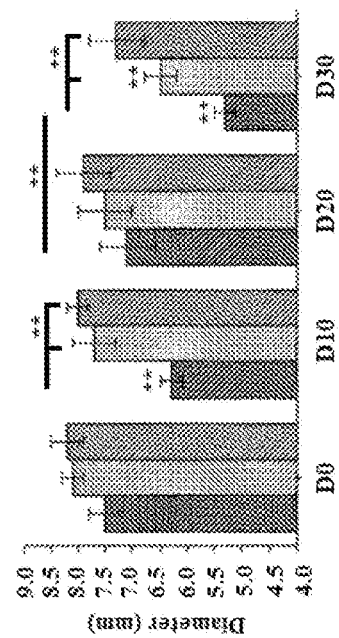
Figure 4P:
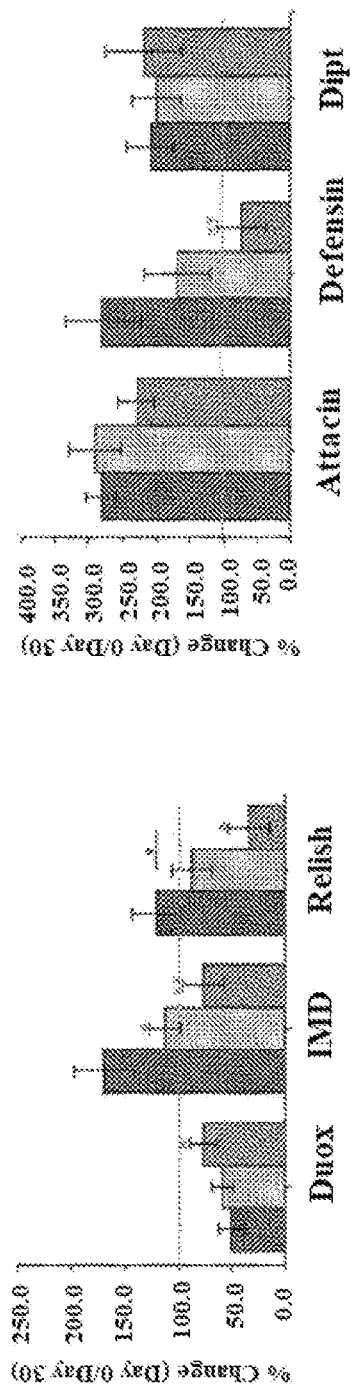
Figure 4Q:
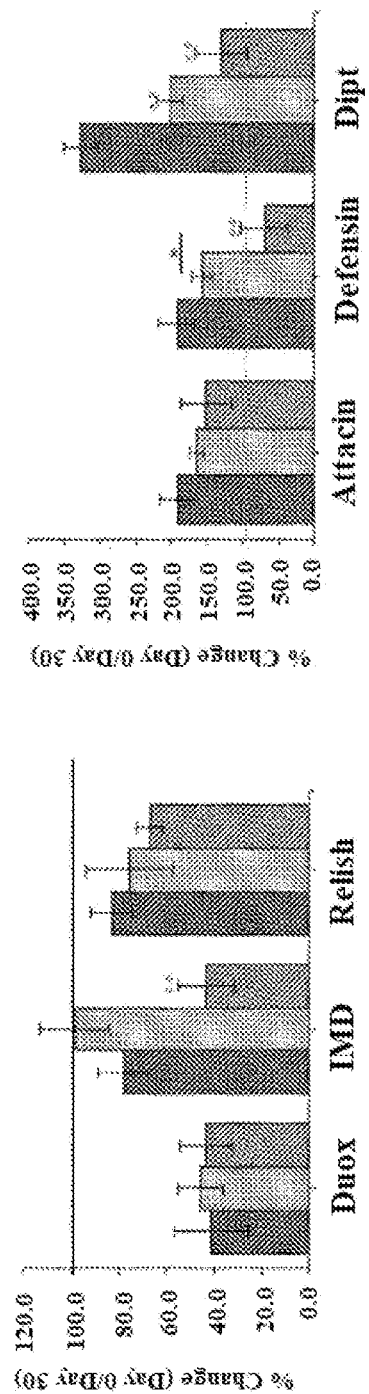

FIGS. 4A to 4Q graphically illustrates data showing that an exemplary probiotic formulation as provided herein has prophylactic efficacy against several markers of Alzheimer's disease and Parkinson's disease:

Humanized transgenic *Drosophila* expressing the α-synuclein mutant A30P (Parkinson's disease; PD) or APP-BACE1 (Alzheimer's disease; AD) were placed on media containing the indicated probiotic treatment throughout their lifecycle. Survivability in both AD (FIG. 4A) and PD (FIG. 4B) *Drosophila* were recorded daily up to 30 days by averaging the count of flies surviving over time. Motility was measured using the negative geotaxis test in both AD (FIG. 4C) and PD (FIG. 4D) flies and represented as the number of seconds it took for 50% of the flies to reach the 10 cm mark. In AD *Drosophila*, the level of amyloid R (A3) (FIG. 4E) was measured over time and represented as the percentage change compared to *Drosophila* at day 0. The total amount of dopamine was measured in g/mg protein from day 0, 10, 20 to 30 was measured (FIG. 4F). Acetylcholinesterase activity (FIG. 4G) was also calculated in AD *Drosophila* and represented as the number of U/min. The varation in the broad metabolic parameters in aging *Drosophila* were measured as total glucose in AD (FIG. 4H) and PD (FIG. 4I) models and total triglycerides in AD (FIG. 4J) and PD (FIG. 4K) models. A summary of the oxidative stress parameters in aging AD (FIG. 4L) and PD (FIG. 4M) *Drosophila* is outlined as the percentage change between *Drosophila* at day 0 to day 30. Regarding the inflammatory markers, the zone of inhibition following the agar diffusion test is represented for both AD (FIG. 4N) and PD (FIG. 4O) *Drosophila* as the diameter of the inhibitory zone. A summary of the immunomodulatory genes is also represented for AD (FIG. 4P) and PD (FIG. 4Q) *Drosophila* as percentage change between gene expression at day 0 to day 30. Finally, the mitochondrial ETC complex activity is again represented for AD (FIG. 4R) and PD (FIG. 4S) *Drosophila* as the percentage change from day 0 to day 30. In all cases, each group represents n=5 independent samples where significance is indicated as black stars (*) for between group comparisons and grey stars (*) compared to the control group where * indicated $p<0.05$ and ** indicated $p<0.01$.

Figure 5A:
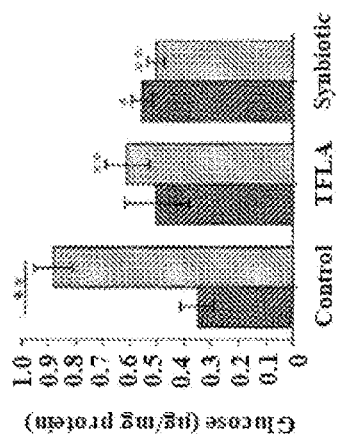
Figure 5A:
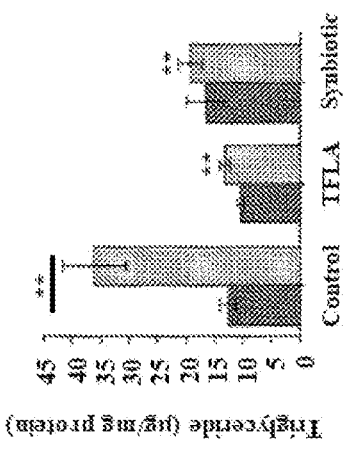
Figure 5B:
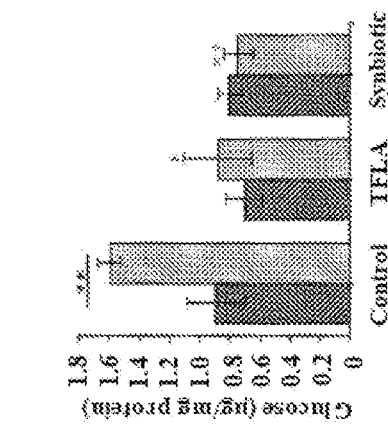
Figure 5B:
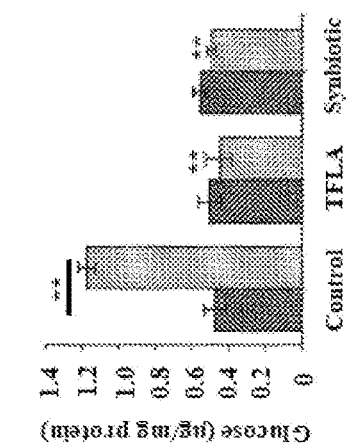
Figure 5B:
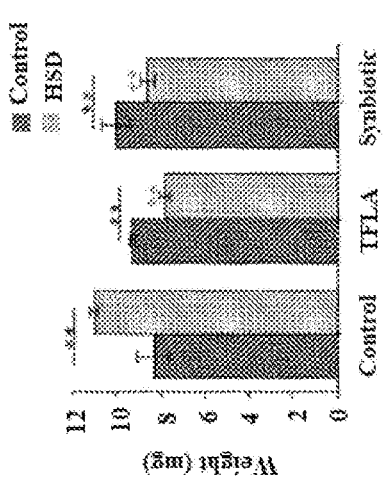
Figure 5B:
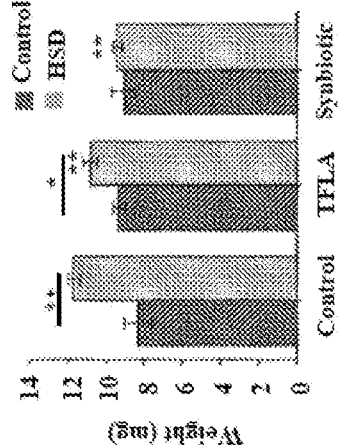
Figure 5C:
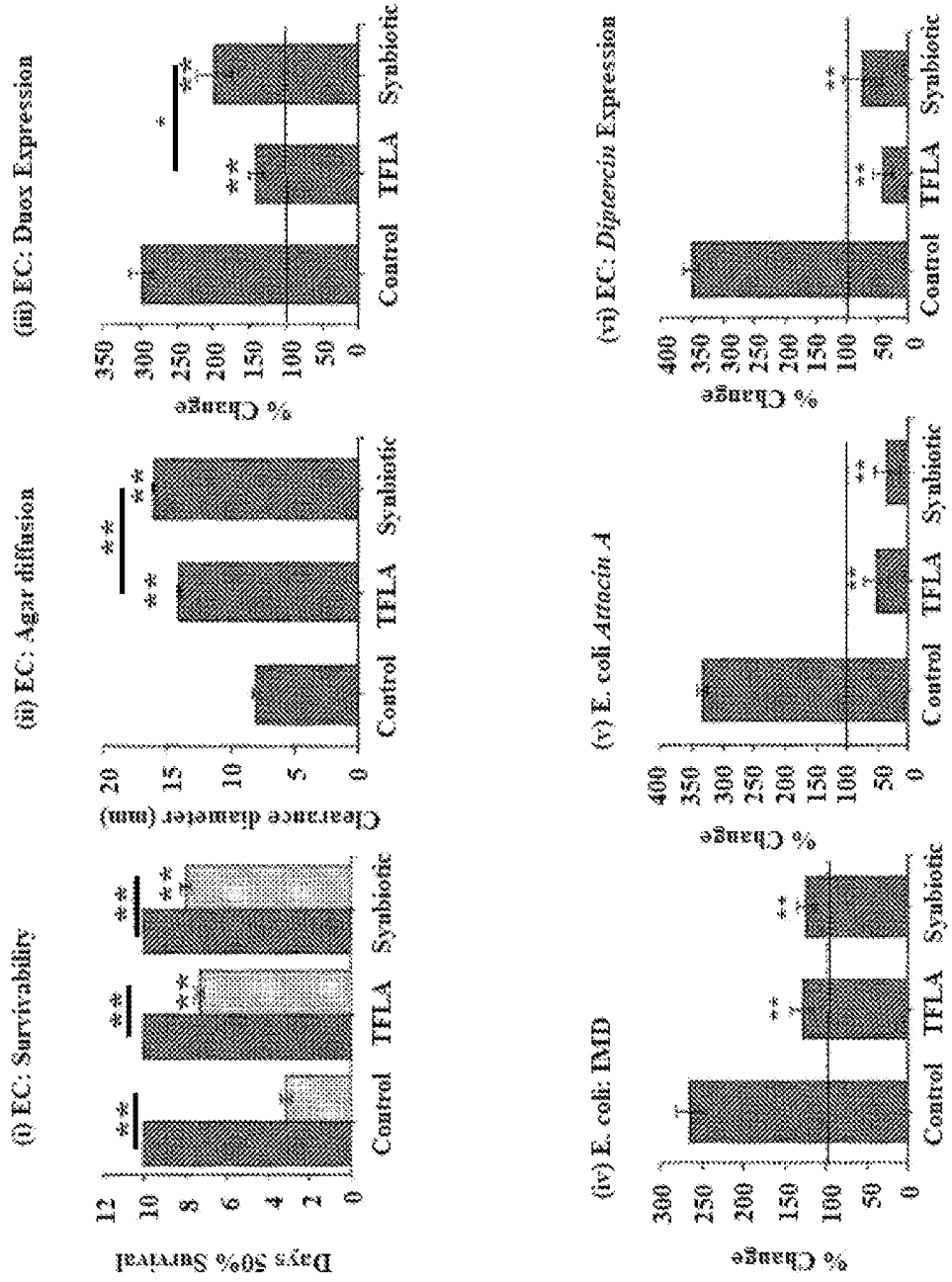

FIGS. 5A to 5F graphically illustrates data showing that an exemplary synbiotic formulation as provided herein does not impede the action of the probiotic formulation in any instance of gut-brain-axis communication:

A prebiotic agent, Triphala (TFLA) was combined with the probiotic formulation (synbiotic) and the activity of several physiological parameters compared between control, TFLA alone and the synbiotic formulation. Metabolic response was measured in either (FIG. 5A) high-sugar diet (HSD)-treated *Drosophila* in terms of variations in (i) body weight, (ii) circulating glucose and (iii) total glucose or (FIG. 5B) high-fat diet (HFD)-treated *Drosophila* including (i) body weight, (ii) total glucose and (iii) total triglycerides. All values are represented as the total enumeration of the parameter in both *Drosophila* on a regular diet (dark grey bars) or the dietary-challenged diet (light grey bars). *Drosophila* treated with the synbiotic formulation were challenged with an acute oral infection with *E. coli* (FIG. 5C). (i) Survivability, (ii) zone of inhibition diameter and gene expression of (iii) Duox, (iv) IMD, (v) Attacin A and (vi) Diptercin are outlined. *Drosophila* treated with the synbiotic formulation were also challenged with an acute oral infection with *S. aureus* (FIG. 5D). (i) Survivability, (ii) zone of inhibition diameter and gene expression of (iii) Duox, (iv) IMD, (v) Attacin A and (vi) Diptercin are outlined. The total level of oxidative stress (FIG. 5E) is shown between untreated (dark grey bars) and hydrogen peroxide challenged (light grey bars) *Drosophila*. (i) Survivability, (ii)

total oxidants, (iii) superoxide dismutase (SOD) activity, (iv) glutathione peroxidase (GPx) activity and (v) lipid peroxidation levels are shown. In humanized transgenic *Drosophila* models of both Alzheimer's disease (AD) and Parkinson's disease (PD) (FIG. 5F) various markers of the disease pathways are depicted in response to the synbiotic treatment. Survivability in both AD (i) and PD (ii) *Drosophila* is shown as the number of surviving flies over 30 days. Motility in both AD (iii) and PD (iv) *Drosophila* is shown according to the negative geotaxis test and the time it took SO % of the *Drosophila* to reach a 10 cm climbing mark. Disease markers for AD including (v) amyloid beta (A3) and (vii) acetylcholinesterase (ACh) activity are shown and in PD *Drosophila* the total dopamine levels (vi). Metabolic markers in both AD (viii) and PD (ix) *Drosophila* depicted including total glucose levels and total triglyceride levels as percentage change compared to *Drosophila* at Day 0. Inflammatory markers in both AD (x) and PD (xi) *Drosophila* are shown as the percentage change between day 30 and day 0 for the gene expression of Duox, IMD, Relish, Attacin A, Defensin and Diptercin. Oxidative stress in both AD (xii) and PD (xiii) *Drosophila* is summarized as the percentage change between days 0 and 30, measuring total oxidants, SOD, GPx and LPO levels. Finally, mitochondrial complex activity in both AD (xiv) and PD (xv) is shown, outlining the % change between days 0 and 30 for ETC complexes 1 through 4. In all cases, each group represents n=5 independent samples where significance is indicated as black stars (*) for between group comparisons and grey stars (*) compared to the control group where * indicated $p<0.05$ and ** indicated $p<0.01$.

Figure 6A:
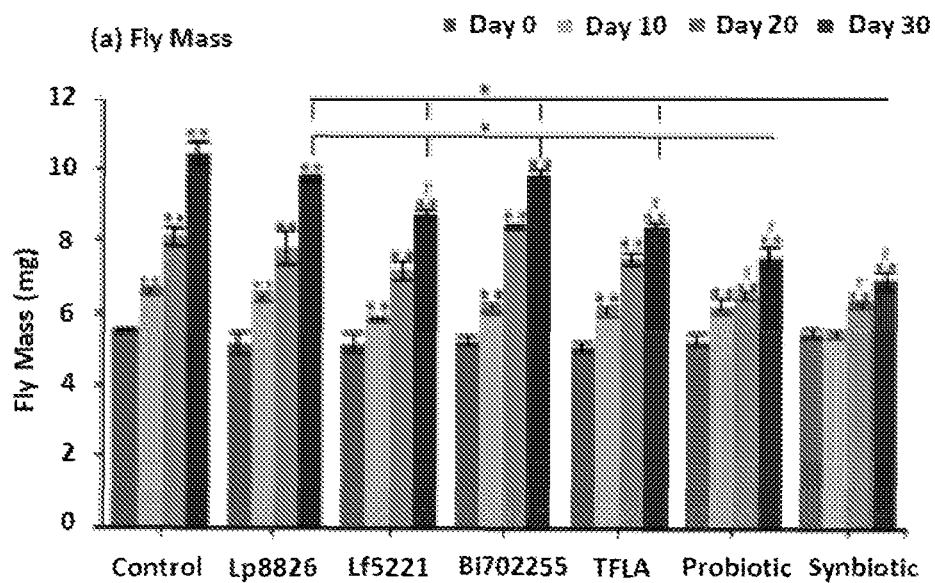
Figure 6B:
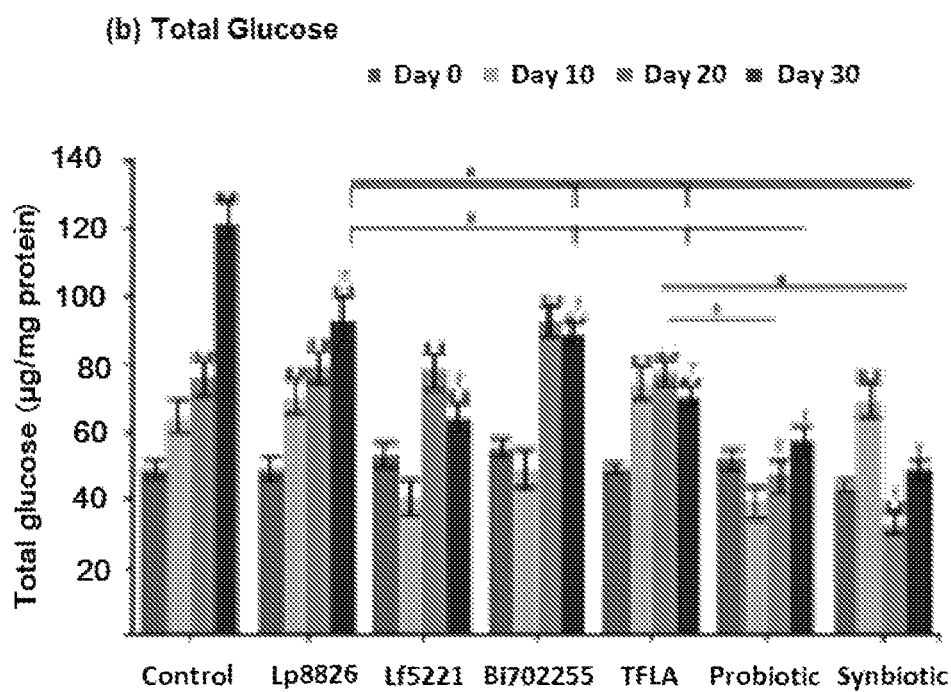
Figure 6C:
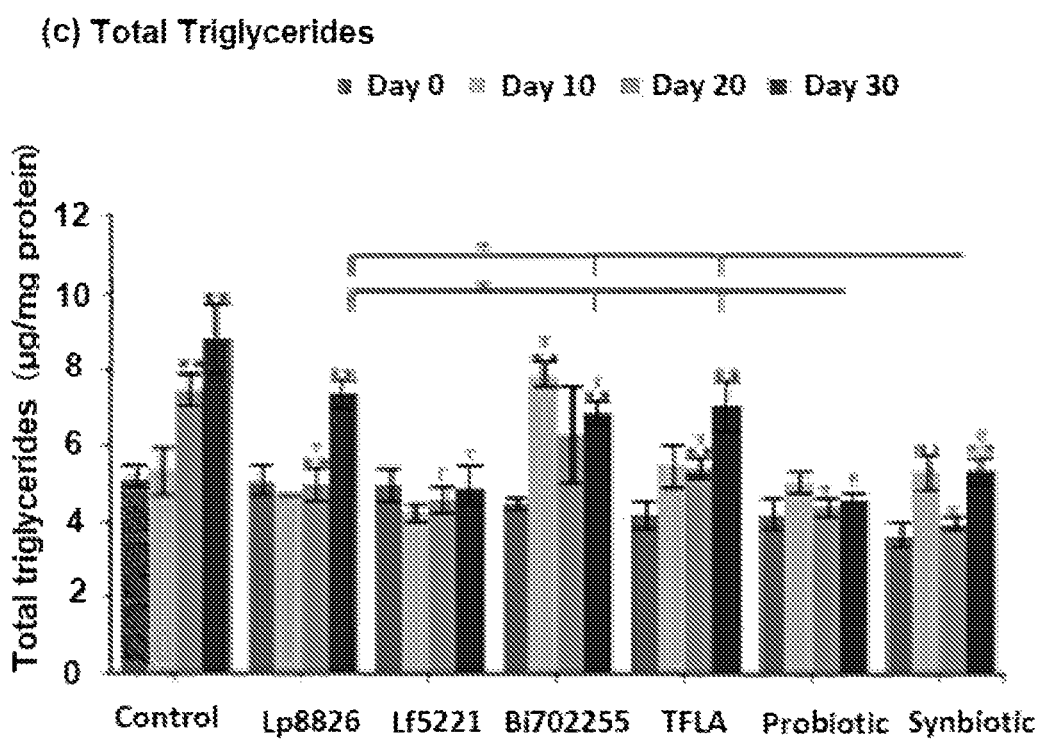

FIGS. 6A to 6C graphically illustrates supplementation with probiotics, a prebiotic or their combination impacts metabolic parameters in aging *Drosophila melanogaster*. Metabolic parameters including (FIG. 5A) weight, (FIG. 5B) total glucose and (FIG. 5C) total triglycerides were measured in aging *Drosophila melanogaster* at days 0, 10, 20 and 30. Each group contained n=5 independent groups and significance is indicated as stars (*) relative to the control day 0 group with * $p<0.05$ and ** $p<0.01$ and as tau (τ) as relative to the no-treatment control at the same time point where r $p<0.05$.

FIG. 7A to 7F graphically illustrates genetic markers of diabetes in aging *Drosophila melanogaster* supplemented with the probiotic and synbiotic formulation. At 0, 10, 20 and 30 days, samples of IS flies were isolated for RNA extraction to measure the expression of several insulin-signaling genes, namely (FIG. 7A) *Drosophila* insulin-like peptide (dilp)2, (FIG. 7B) dilp3, (FIG. 7C) insulin receptor (InR), (FIG. 7C) dAkt, (FIG. 7E) dTOR and (FIG. 7F) dFOXO. Each group contained n=5 independent groups and significance is indicated as stars (*) relative to the control day 0 group with * $p<0.05$ and ** $p<0.01$ and as tau (r) as relative to the no-treatment control at the same time point where T $p<0.05$.

FIGS. 8A to 8D graphically illustrates genetic markers of obesity in aging *Drosophila melanogaster* supplemented with the probiotic and/or synbiotic formulation. At 0, 10, 20 and 30 days, samples of 15 flies were isolated for RNA extraction to measure the expression of fat metabolism genes, namely (FIG. 8A) acetyl-CoA carboxylase, (FIG. 8B) fatty acid synthase (FAS), (FIG. 8C) phospholenol pyruvate carboxykinase (PEPK) (FIG. 8D) sterol-regulatory element binding protein (SREBP) (e) Lipid storgae droplet (Lsd)2 and (f) E75. Each group contained n=5 independent groups and significance is indicated as stars (*) relative to the control day 0 group with * $p<0.05$ and ** $p<0.01$ and as tau (r) as relative to the no-treatment control at the same time point where r $p<0.05$.

Figure 9A:
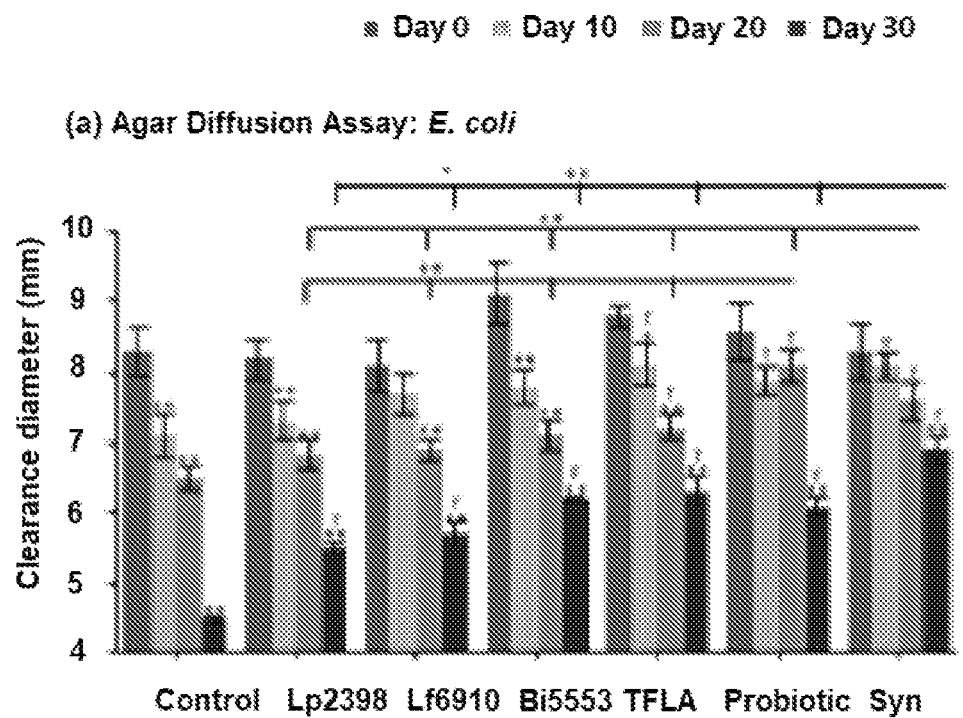
Figure 9B:
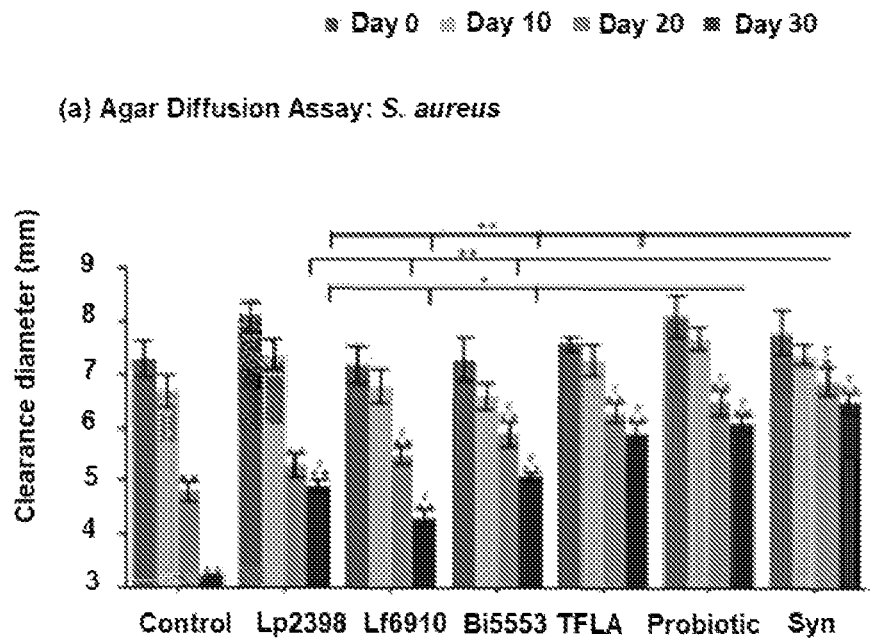

FIGS. 9A to 9G graphically illustrates age-related variations in innate immunity factors in *Drosophila melanogaster* are ameliorated by the synbiotic formulation. At days 0, 10, 20 and 30, *Drosophila melanogaster* on media supplemented with the individual probiotics, prebiotic or a combination of the probiotics and/or prebiotics were tested for their immunological response. The agar diffusion test measuring the production of antimicrobial factors was performed on plates with lawns of (FIG. 9A) *E. coli* and (FIG. 9B) *S. aureus* pathogenic species. Gene expression of several immunological genes were also assessed including (FIG. 9C) dual oxidase (duox), (FIG. 9D) immune deficiency (IMD), (FIG. 9E) Relish, (FIG. 9F) Attacin A, (FIG. 9G) Defensin and Diptercin (FIG. 9H). Each group contained n=5 independent groups and significance is indicated as stars (*) relative to the control day 0 group with * $p<0.05$ and ** $p<0.01$ and as tau (r) as relative to the no-treatment control at the same time point where r $p<0.05$.

FIGS. 10A to 10H graphically illustrates that the probiotic and synbiotic formulation has a combinatorial effect on markers of oxidative sXrsss. *Drosophila melanogaster* were supplemented with the individual probiotic, prebiotic, the probiotic or synbiotic formulation and the levels of (FIG. 10A) total oxidants, (FIG. 10B) superoxide dismutase activity, (FIG. 10C) glutathione peroxidase activity and (FIG. 10D) lipid peroxidation were measured at 0, 10, 20 and 30 days of age. The activity of ETC (FIG. 10E) complex 1 (NADH coenzyme Q reductase), (FIG. 10F) complex 2 (succinate dehydrogenase), (FIG. 10G) complex 3 (cytochrome bcl complex) and (h) complex 4 (cytochrome c oxidase) was also assessed using various biochemical assays. Each group contained n=5 independent groups of 25 flies and significance is indicated as stars (*) relative to the control day 0 group with * $p<0.05$ and ** $p<0.01$ and as tau (τ) as relative to the no-treatment control at the same concentration where τ $p<0.05$.

Figure 11:
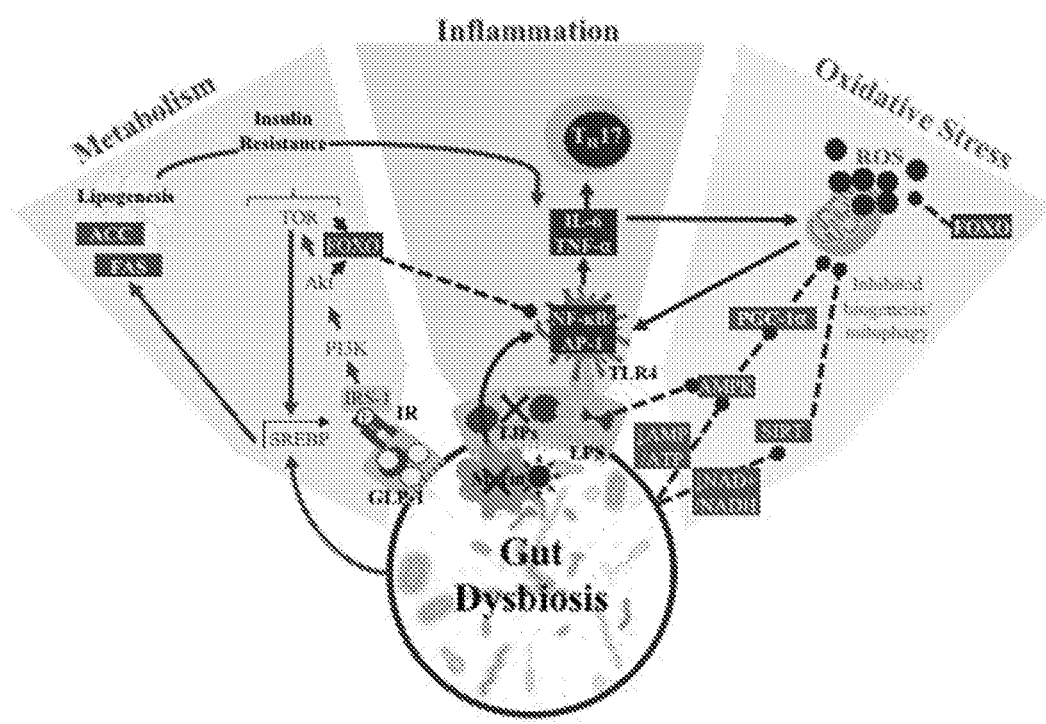

FIG. 11 depicts a model of mechanisms of gut microbiota-host communication influencing aging factors. The gut microbiota communicates with the metabolic, inflammatory and oxidative stress pathways via direct and indirect mechanisms. As the physiological changes in all three of these axes are cross-regulatory, the simultaneous action implemented by the gut microbiota makes it a powerful influence in aging and age-related chronic disease development.

Abbreviations: glucagon-like peptide (GLP)-1, insulin receptor (IR), insulin receptor substrate (IRS)-1, phosphoinositide 3-kinase (PI3K), protein kinase B (Akt), target of rapamycin (TOR), Forkhead Box O protein (FOXO), sterol regulatory element binding protein (SREBP), acetyl CoA carboxylase (ACC), fatty acid synthase (FAS), tight junction proteins (TJPs), lipopolysaccharide (LPS), toll-like receptor (TLR)4, nuclear factor kappa-light-chain enhancer of activated B cells (NF-kB), activator protein (AP)-1, tumor necrosis factor (TNF)-a, interleukin (IL)-6, T helper (Th)17, AMP-activated protein kinase (AMP), peroxisome proliferator-activated receptor gamma coactivator (PGC)-lct, sirtuin (SIRT), reactive oxygen species (ROS).

Like reference symbols in the various drawings indicate like elements.

DETAILED DESCRIPTION

In alternative embodiments, provided are probiotic formulations, including compositions, products of manufacture and kits comprising them, and methods of using them, for the treatment, amelioration, prevention and/or alleviation of (e.g., reducing the symptoms of) metabolic and oxidative stress, inflammation and neurodegeneration. In alternative embodiments, probiotic formulations as provided herein are used for: the treatment, amelioration, prevention and/or alleviation of (e.g., reducing the symptoms of) of: metabolic conditions such as diabetes and obesity, inflammatory conditions such as Inflammatory Bowel Disease (IBD) and Irritable Bowel Syndrome (IBS); arthritis; neurodegenerative diseases such as Alzheimer's disease and Parkinson's disease; oxidative stress, including resisting oxidative stress; inflammation, including reducing inflammation. In alternative embodiments, probiotic formulations as provided herein are used for lowering blood and total glucose levels, lowering triglycerides levels and managing insulin resistance.

In alternative embodiments, probiotic formulations as provided herein consist of any combination of the three probiotic strains: *Lactobacillus fermentum* NCIMB S221, *Lactobacillus plantarum* NCIMB 8826 and *Bifidobacteria longum* spp. *infantis* NCIMB 702255.

Probiotic formulations as provided herein have proven efficacy for resisting oxidative stress, reducing inflammation, lowering blood and total glucose levels, lowering triglycerides levels and managing insulin resistance.

In alternative embodiments, probiotic formulations as provided herein are combined with a triphala, or any herbal rasayana formula consisting of relatively equal parts of three myrobalans, taken without seed: amalaki (*Emblica officinalis*), bibhitaki (*Terminalia bellirica*), and haritaki (*Terminalia chebula*). In alternative embodiments, use of triphala improves the efficacy of probiotic formulations as provided herein. This embodiment provides a novel probiotic and synbiotic formulations.

In alternative embodiments, probiotic formulations as provided herein, including probiotic formulations combined with triphala, or any herbal rasayana formula consisting of relatively equal parts of three myrobalans, taken without seed: amalaki (*Emblica officinalis*), bibhitaki (*Terminalia bellirica*), and haritaki (*Terminalia chebula*), provide an efficacious solution for managing age- and diet-related chronic diseases through healing the gut microbiota and beneficially altering signaling pathways implicated in gut-brain axis signaling.

In alternative embodiments, probiotic formulations further comprise any one or several (e.g., one, two, three, four or five of more) of the following microorganisms and all strains therein: *Lactobacillus fermentum* 11976, *Lactobacillus leichmanni* NCIMB 7854, *Lactobacillus farciminis* NCIMB 11717, *Lactobacillus fermentum* NCFB 1751, *Lactobacillus fermentum* NCIMB 2797, *Lactobacillus reuteri* NCIMB11951, *L. acetotolerans, L. acidifarinae, L. acidipiscis, L. acidophilus, L. agilis, L. algidus, L. alimentarius, L. amylofyticus, L. amylophilus, L. amylotrophicus, L. amylovorus, L. animalis, L. antri, L. apodemi, L. aviaries, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *bulgaricus, L. delbrueckii* subsp. *delbrueckii, L. delbrueckii* subsp. *lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamster, L. harbinensis, L. hayakitensis, L. helveticus, L. hilgardii, L. homohiochii, L. iners, L. ingluviei, L. intestinalis, Ljensenii, Ljohnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L ultunensis, L. vaccinostercus, L. vaginalis, L. versmoldensis, L. vini, L. vitulinus, L. zeae, L. zymae, Bacillus subtilis* FMCC 193, *Bacillus subtilis* FMCC 267, *Bacillus subtilis* FMCC PL-1, *Bacillus subtilis* FMCC 511, *Bacillus subtilis* NCIMB 11034 *Bacillus subtilis* NCIMB 3610, *Bacillus pumilis* ATCC 7661, *Bacillus sphaericus* ATCC 14577 and *Bacillus licheniformis* ATCC 14580 *Bifidobacterium lactis, Bifidobacterium longum, Bifidobacterium bifidum, Bifidobacterium infantis, Bifidobacterium adolescentis, Bifidobacterium angulatum, Bifidobacterium breve, Bifidobacterium catenulatum, Bifidobacterium denticolens, Bifidobacterium dentium, Bifidobacterium gallicum Bifidobacterium inopinatum, Bifidobacterium pseudocatenulatum Bifidobacterium lactis, Bifidobacterium minimum, Bifidobacterium subtile, Bifidobacterium thermacidaphilum, Bifidobacterium animalis, Bifidobacterium asteroids, Bifidobacterium boum, Bifidobacterium choerum, Bifidobacterium coryneforme, Bifidobacterium cuniculi, Bifidobacterium gallmarum, Bifidobacterium indicum, Bifidobacterium magnum, Bifidobacterium merycicum, Bifidobacterium pseudolongum* subsp *Pseudolongum, Bifidobacterium pseudolongum* subsp *Globosum, Bifidobacterium pullorum, Bifidobacterium rummantium, Bifidobacterium saeculare, Bifidobacterium suis, Bifidobacterium thermophilum* or yeast cells chosen from *Saccharomyces cerevisiae, Saccharomyces carlsbergensis Saccharomyces chevalien Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxu, Saccharomyces sake, Saccharomyces uvarum, Saccharomyces willianus, Saccharomyces* sp, *Schizosaccharomyces octosporus Schizosaccharomyces pombe, Sporobolomyces roseus Torulopsis Candida, Torulopsis famta, Torulopsis globosa, Torulopsis inconspicua, Trichosporon behrendu, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyu, Geotrichum candidum, Hansenula anomala, Hansenula arabitolgens, Hansenula jadinn, Hansenula saturnus, Hansenula schneggn, Hansenula subpelliculosa, Kloeckera apiculata, Lipomyces starkeyi, Pichia fannosa, Pichia membranaefaciens RhodospoKdium toruloides, Rhodotorula glutinis, Rhodotorula minuta, Rhodotorula rubor, Rhodotorula aurantiaca, Saccharomycodes ludwign, Saccharomycodes sinenses, Saccharomyces cerevisiae* Hansen AS2 375, AS2 501, AS2 502, AS2 503, AS2 504, AS2 535, AS2 558, AS2 560, AS2 561, AS2 562, or IFFI1048, or *Saccharomyces carlsbergensis* Hansen AS2 420 and AS2 444, and any equivalent thereof or combination thereof.

In alternative embodiments, probiotic formulations further comprise any one or several (e.g., one, two, three, four or five of more) of the following prebiotics, or prebiotic-like materials, including e.g.: fructooligosaccharides, galactooligosaccharides, glucose, galactose, xylose, maltose, sucrose, lactose, starch, xylan, hemicellulose, inulin, gum, *Panax ginseng* (red, Korean ginseng), *Panax ginseng* (white, Chinese ginseng), *Rhodiola rosea* (golden root), *Panax quinquefolium* (American ginseng), *Eleutherococcus senticosus* (Siberian ginseng), *Cynara scofymus* (artichoke), *Uncaria tomentosa* (Cat's claw), *Lepidium meyenii* (maca, Peruvian ginseng), *Paullinia cupana* (guarana), *Croton lechleri* (Sangre de Grado), *Wliitania somnifera* (ashwagandha, Indian ginseng), *Panax japonicus* (Japanese ginseng), *Panax vietnamensis* (Vietnamese ginseng), *Panax trifolius, Panax pseudoginseng, Panax notoginseng, Malpighia glabra* (acerola), *Ylex paraguayiensis* (Y erba mate), *Astragalus membranaceus* (astragalus), *Stevia rebaudiana* (stevia), *Pfaffia paniculata* (Brazilian ginseng, suma), *Ginkgo biloba, Tabebuia impetiginosa* (Pau d'arco), *Echinacea purpurea, Peumus boldus* (boldo), *Gynostemma pentaphyllum* (Jiaogulan, also known as Southern Ginseng or Xiancao), *Sutherlandia frutescens* (African ginseng), *Aloe vera* (aloe), *Cistanche salsa, Cistanche deserticola* (and other *Cistanche* sp.), *Codonopsis pilosula* ("poor man's ginseng."), *Nopal opuntia* (Prickly pear cactus), *Citrus sinensis* (*Citrus aurantium*) and other members of the citrus family (lemon, lime, tangerine, grapefruit), *Camelia sinensis* (tea), *Plantago psyllium* (psyllium), *Amaranth edulis* and other *amaranth* sp. (amaranth), *Commiphora mukul* (guggul lipid), *Serenoa repens, Serenoa serrulata* (saw palmetto), *Cordyceps sinensis* (Cordycaps), *Lentinula edodes* (Shitake), *Ganoderma lucidium* (Reishi), *Grifola rondosa* (maitake), *Tremella fuciformis* (Silver ear), *Poria cocos* (Hoelen), *Hericium erinaceus* (Lion's Mane), *Agaricus blazei* (Sun mushroom), *Phellinus linteus* (Mulberry yellow polypore), *Trametes versicolor, Coriolus versicolor* (Turkey tails), *Schizophyllum commune* (Split gill), *Inonotus obliquus* (Cinder conk), oat bran, rice bran, linseed, garlic, *Ceratonia siliqua* (locust been gum or flour from the seeds of carob tree), *Cyanopsis tetragonoloba* (guar gum, EU Food additive code E412), *Xanthomonas campestris* (xanthan gum), and any equivalent thereof or combination thereof.

In alternative embodiments, the products of manufacture, compositions, formulations, pharmaceutical compositions or kit as provided herein are used prophylactically and/or therapeutically in animals (e.g., animal models) and humans suffering from type II diabetes or insulin resistance; by optionally, lowering total and circulating glucose levels, triglyceride levels, total weight, inflammation, oxidative stress and/or any mitochondrial dysfunction.

In alternative embodiments, the products of manufacture, compositions, formulations, pharmaceutical compositions or kit as provided herein are used prophylactically and/or therapeutically in animals (e.g., animal models) and humans suffering from obesity, hyperlipidemia or are overweight by lowering total weight, triglyceride levels, glucose levels, insulin resistance, inflammation, oxidative stress and/or mitochondrial dysfunction.

In alternative embodiments, the products of manufacture, compositions, formulations, pharmaceutical compositions or kit as provided herein are used prophylactically and/or therapeutically in animals (e.g., animal models) and humans suffering from inflammatory conditions including pathogenic infection, arthritis, inflammatory bowel disease, inflammatory bowel syndrome, Crohn's disease, ulcerative colitis and symptoms of inflamm-aging by lowering circulating inflammatory markers (cytokines, chemokines, etc.).

In alternative embodiments, the products of manufacture, compositions, formulations, pharmaceutical compositions or kit as provided herein are used prophylactically and/or therapeutically in animals (e.g., animal models) and humans suffering from acute and/or chronic oxidative stress via lowering total oxidants counts, lipid peroxidation and increasing the activity of superoxide dismutase and glutathione peroxidase.

In alternative embodiments, the products of manufacture, compositions, formulations, pharmaceutical compositions or kit as provided herein are used prophylactically and/or therapeutically in animals (e.g., animal models) and humans suffering from neurodegeneration including Alzheimer's disease and Parkinson's disease by lowering metabolic distress (e.g., high glucose, high triglyceride, obesity, insulin resistance), inflammation, oxidative stress and through affecting mitochondrial electron chain complex activity. In alternative embodiments, probiotic formulations as provided herein are combined with any other probiotic bacteria or prebiotic substance, optionally providing enhanced effect, and optionally without any negative effect on the formulation's efficacy on the aforementioned parameters.

The invention will be further described with reference to the examples described herein; however, it is to be understood that the invention is not limited to such examples.

EXAMPLES

The *Drosophila melanogaster* model is an effective and predictive model for assessing various treatment in humans, e.g., for: treating diet-induced diabetes/insulin resistance and/or obesity/hyperlipidemia; treating or ameliorating inflammation; or, for treating or ameliorating acute stress; treating or ameliorating, or slowing the progress of or slowing the onset of a Neurodegenerative Disease, including Alzheimer's disease (AD) and Parkinson's disease (PD). While *Drosophila melanogaster* may be small, they retain a great amount of cellular and molecular homology to humans, including regulation of gene expression, membrane trafficking, neuronal connectivity, cell signaling, synaptogenesis and cell death. Further, *Drosophila* are highly genetically amenable, making the modeling of genetic disorders more feasible than with higher organisms. One of the most common expression transgenic systems in *Drosophila* is the UAS (upstream activation system)-Gal4 system that allows genes downstream of the UAS element to be driven by the specific cell expression of Gal4 driven by the promoter of choice. Indeed, 75% of human genes that are associated with disease have a functional homolog in the fly with an 80-90% conservation of functional domains (Reiter, Potocki, Chien, Gribskov, & Bier, 2001). *Drosophila* also have a well-organized brain, albeit with fewer cells and a different neuroanatomical organization. The simplicity of *Drosophila* may be its most significant strength as the functional redundancy present in mammals is not found as extensively in flies allowing the molecular pathways to be deciphered. Finally, its short life cycle and completely sequenced genome is another experimental advantage possessed by the organism (Sang & Jackson, 200S); see also: Reiter, et al (2001) A systematic analysis of human disease-associated gene sequences in *Drosophila melanogaster*. Genome Research, 11(6), 1114-112S. and Sang, T.-K. et al (2005) *Drosophila* models of neurodegenerative disease. NeuroRx: the Journal of the American Society for Experimental NeuroTherapeutics, 2(3), 438-446.

Example 1: Exemplary Compositions for Treating Diabetes and Obesity

The following example demonstrates the efficacy of exemplary probiotic formulations for treating or ameliorating diabetes and obesity.

We have outlined several parameters of diabetes and obesity that are positively affected by the probiotic formulation supported by mechanistic studies that outline how the probiotics are communicating with the host physiology supporting the robust nature of the probiotic treatment. We assessed the ability of an exemplary probiotic formulation as provided herein to affect the physiological attributes of diet-induced diabetes/insulin resistance or obesity hyperlipidemia in the art-accepted model of Drosophila melanogaster.

Methods

Bacterial Culture

Bacterial cultures (Lp8826, Lf5221, Bi702255) from a frozen glycerol stock were cultured in Man-Rogosa-Sharpe (MRS) media obtained from Sigma Aldrich (Oakville, ON, Canada) at 37° C. on MRS-agar plates or in liquid media. After one round of liquid culture, several bacterial stocks were made in MRS containing 20% (v/v) glycerol and stored at −80° C. as working stocks. As constant culturing was required to carry out all experiments, bacterial stocks were renewed from the frozen stock biweekly to maintain culture purity. To perform each individual experiment, a 1% (v/v) inoculum was used for subculturing, incubated at 37° C. for 18 h and removed immediately before use. To prepare the individual Drosophila treatment bottles, the overnight culture was centrifuged at 4000 rpm for 10 min at 4° C. The pellet was washed once and resuspended in 0.8S % (w v) sterile physiological saline. Total colony counts were determined by spectrophotometry compared to a standard curve prepared with colony forming units (CFUs) on MRS plates.

Drosophila Husbandry

Wildtype Drosophila melanogaster (Oregon R) were procured from the Bloomington Drosophila Stock Center (Indiana University, Bloomington Indiana). Flies were reared on a standard cornmeal-sucrose-yeast media without active yeast culture prepared by boiling the cornmeal (83 g), sucrose (SO g) and yeast extract (30 g) in distilled water for 30 min. Drosophila were kept in controlled conditions with a 12 h:12 h light-dark cycle at 25° C. Inoculated media was prepared by partitioning the concentrated bacterial culture into the cooled, yet liquid, media. The bacteria were deemed viable in the Drosophila media for up to two weeks before a detectable loss of concentration by daily CFU counting. The viability of the inoculated bacterial strains was also verified in the GIT of the flies through real-time PCR quantification. Nevertheless, flies were transferred to newly inoculated bottles every 3-4 days during the course of an experiment to ensure constant inoculation of pure probiotic bacteria.

Freshly enclosed flies were acclimatized for 7 days on media containing either a control media, media inoculated with a single bacterium (Lp8826, Lf5221, Bi702255) at 3.0×109 CFU/ml, or the probiotic formulation with each bacterium at 1.0×109 CFU/ml. Each group consisted of 5 independent samples of 20-50 flies, depending on the experimental procedure. Following acclimatization and proper construction of the gut microbiota, flies were transferred to similarly treated media with the addition of a high-sugar-diet (HSD) containing 1 M sucrose or a high-fat diet (HFD) containing in addition to the normal media, 30% coconut oil. Flies were allowed to feed for 10 days on the new treated media after which they were anesthetized, weighed, rinsed in a 10% bleach solution and thrice in water before processing.

Physiological Metabolic Parameters

Physiological parameters were assessed on freshly anesthetized flies. Body weight was assessed by weighing ten flies in replicates of five. Glucose measurements were taken from both hemolymph (circulating glucose) and whole-body homogenates of Drosophila. Before measurement, the homogenate was heat-treated for 20 min at 70° C. to remove any complexes. Glucose levels were measured in 2 µl of hemolymph or 5 µl of whole-body homogenate using the Glucose (HK) Assay kit (Sigma, Oakvilla, ON, Canada) according to the manufacturer's instructions. Whole-body triglycerides were determined in 10 µl of homogenate using the Triglycerides Liquicolor Test Mono (Stanbio, TX, USA) according to the manufacturer's instructions. Measurements were all normalized to the protein content in each sample and statistical differences were calculated using a 2-way ANOVA with Tukey's post hoc analyses.

Gene Expression Analyses

RNA was extracted from whole flies using Trizol (ThermoFisher, MA, USA) according to the manufacturer's instructions. cDNA was synthesized from 1 ug of RNA measured with the ND-2000 Nanodrop (FisherScientific, Ottawa, ON, Canada) using the High-Capacity cDNA Synthesis Kit (ThermoFisher, MA, USA) according 5 to the manufacturer's instructions. Real-time PCR was conducted on the Eco Realtime PCR System (Illumina, CA, USA) using SybrGreen detection method (Diamed, Mississauga, ON, Canada) and quantification according to the 2"ddCT method using Rp49 as a reference standard. Primer pairs and annealing temperatures are listed in Table 1:

TABLE 1

Primer pairs and annealing temperatures

| Gene Name | Sequence (5'-3') | SEQ ID NO: | Annealing Temp |
|---|---|---|---|
| InR | F: AACAGTGGCGGATTCGGTT | SEQ ID NO: 1 | 54° C. |
| | R: TACTCGGAGCATTGGAGGCAT | SEQ ID NO: 2 | |
| Dilp 2 | F: AGCAAGCCTTTGTCCTTCATCTC | SEQ ID NO: 3 | 50° C. |
| | R: ACACCATACTCAGCACCTCGTTG | SEQ ID NO: 4 | |
| Dilp 3 | F: TGTGTGTATGGCTTCAACGCAATG | SEQ ID NO: 5 | 50° C. |
| | R: CACTCAACAGTCTTTCCAGCAGGG | SEQ ID NO: 6 | |
| dTOR | F: GGCCGTCCAGGTTCAAAAAC | SEQ ID NO: 7 | 59° C. |
| | R: AATCCGGCGATAGTTCCGTC | SEQ ID NO: 8 | |
| dAkt | F: GAGTCGTGTGCTCAAGTCCA | SEQ ID NO: 9 | 59° C. |
| | R: TGCATCACAAAACACAGGCG | SEQ ID NO: 10 | |
| dFOXO | F: TCGCCGAACTCAGTAACCAC | SEQ ID NO: 11 | 59° C. |
| | R: TCCTATCAAAGTAGAGGCGCA | SEQ ID NO: 12 | |

TABLE 1-continued

Primer pairs and annealing temperatures

| Gene Name | Sequence (5'-3') | SEQ ID NO: | Annealing Temp |
|---|---|---|---|
| ACC | F: TTAGTCAGCTGCAGGCAAAG | SEQ ID NO: 13 | 54° C. |
| | R: CGGAAGCTAACGCCACACA | SEQ ID NO: 14 | |
| FAS | F: CAACAAGCCGAACCCAGATCTT | SEQ ID NO: 15 | 50° C. |
| | R: CAAAGGAGTTCAGGCCGATGAT | SEQ ID NO: 16 | |
| PEPCK | F: CGCCCAGCGACATGGATGCT | SEQ ID NO: 17 | 60° C. |
| | R: GTACATGGTGCGACCCTTCA | SEQ ID NO: 18 | |
| LSD | F: ACTTGTAGTGCCAGTTCCCG | SEQ ID NO: 19 | 52° C. |
| | R: ACCAGACTGCTCCACATTCG | SEQ ID NO: 20 | |
| E78 | F: CAGTGTCTCTCGTTGCTCA | SEQ ID NO: 21 | 54° C. |
| | R: AACCGATTGCTTCGCTCTCT | SEQ ID NO: 22 | |
| SREBP1 | F: GGCAGTTTGTCGCCTGATG | SEQ ID NO: 23 | 56° C. |
| | R: CAGACTCCTGTCCAAGAGCTGTT | SEQ ID NO: 24 | |
| Rp49 | F: AGATCGTGAAGAAGCGCACCAAG | SEQ ID NO: 25 | 52° C. |
| | R: CACCAGGAACTTCTTGAATCCGG | SEQ ID NO: 26 | |

Statistics

Statistics were all conducted using R statistical software. A multi-variant 2-way ANOVA was conducted for all groups with Tukey post-hoc analysis. Significance was determined with $p<0.05$.

Results & Discussion

Figure 1A:
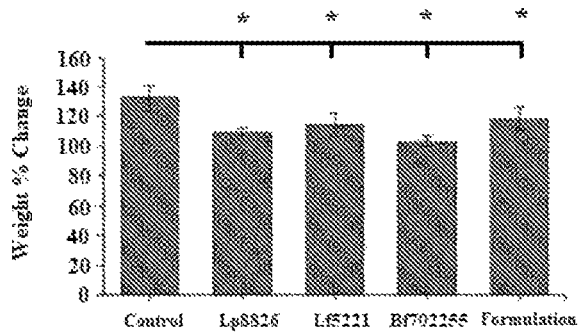
FIGS. 1A to F graphically illustrate data showing that an exemplary Probiotic Formulation as provided herein reduces markers of diabetes and obesity in *Drosophila*. *Drosophila* fed on a high-sugar diet (HSD) exhibited elevations in several physiological markers of the diabetic phenotype, which were effectively reduced by the probiotic formulation. The results are set forth in FIG. 1A showing the reductions in body weight, FIG. 1B showing the reductions in circulating glucose levels and FIG. 1C showing the reductions in total glucose levels. *Drosophila* fed on a high-fat diet (HFD) exhibited elevations in several physiological markers of obesity, which were effectively reduced by the probiotic formulation. This includes reductions in body weight shown in FIG. 1D, reductions in total glucose shown in FIG. 1E and reductions in total triglycerides shown in FIG. 1F. Each group is represented as the percentage change of the HFD group compared to controls on normal diet with the same respective treatment probiotic treatment. Each group contained n=5 individual samples and significance is marked as * $p<0.05$ and ** $p<0.01$.
Figure 1B:
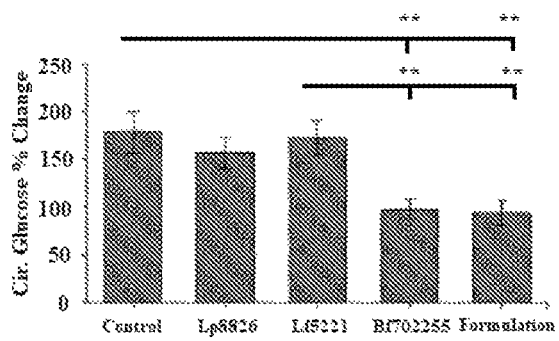
Figure 1C:
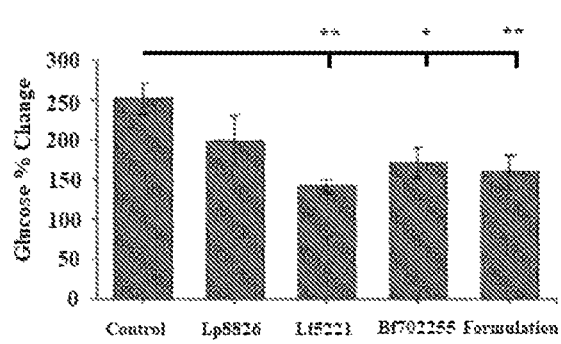

Physiological parameters that were measured to assess the impact of a HSD (emulating diet-induced diabetes) or a HFD (emulating obesity) on Drosophila include 1) total weight, 2) circulating glucose, 3) total glucose and 4) total triglycerides. In HSD flies, there was a 32.4% increase in the total body weight of control flies (FIG. 1a). Lp8826, Lf5221 and Bi702255 significantly reduced this elevation to 9.8%, 14.3% and 3.40% respectively while the probiotic formulation reduced the total weight gain by 18.1%. As expected with a diabetic phenotype, there was a sharp increase in the levels of circulating glucose in control flies by 78.7% (FIG. 1b). This elevation was significantly higher than both the Bi702255 and probiotic formulation groups which demonstrated a reduction in circulating glucose levels compared to untreated controls by 2.2% and 5.7%, respectively. For the circulating glucose measure, the probiotic formulation more effectively reduced glucose levels compared to both Lp8826 and Lf5221 single probiotic treatments. Similarly, total glucose levels were significantly elevated in the HSD control groups by IS 1.4% (FIG. 1c). This elevation was significantly higher than the LfS221, Bi702255 and probiotic formulation groups which showed elevations of 41.0%, 71.0% and S8.7%, respectively, compared to controls. Overall, the probiotic formulation consistently demonstrated the ability to reduce the physiological parameters of diet-induced diabetes to a similar if not better extent than the individual probiotics. Although some of the individual probiotics demonstrated the ability to reduce the physiological parameters of diabetes to the same extent as the probiotic formulation, none could consistently reduce all of the parameters to the same level as the probiotic formulation indicating that the formulation can robustly treat all aspects of diet-induced diabetes.

Figure 1D:
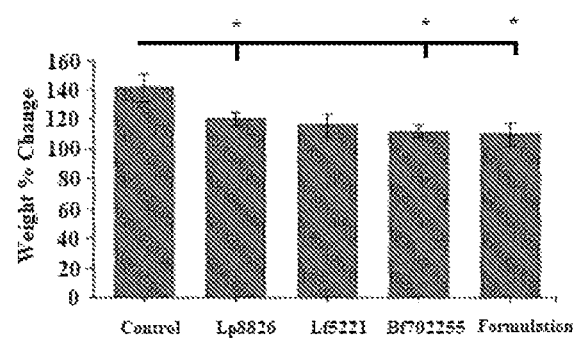
Figure 1E:
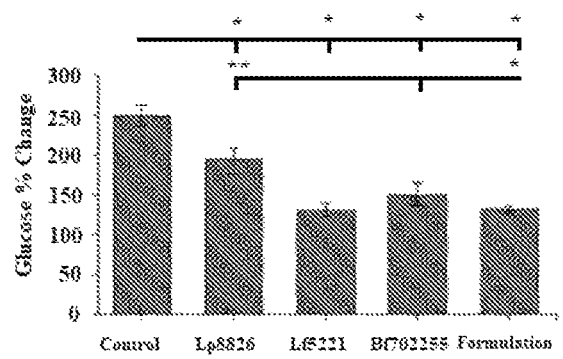
Figure 1F:
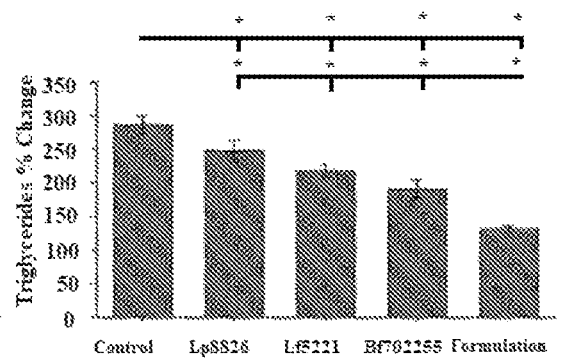

In the HFD-fed Drosophila melanogaster, there was a significant 41.0% increase in total body weight in controls (FIG. 1d). This increase was significantly higher than the Lp8826, Bi702255 and probiotic formulation groups which demonstrated weight increases of 20.4%, 1 1.9% and 9.1%, respectively, compared to controls. Total glucose levels were elevated by 148% in control flies (FIG. 1e), which was significantly higher than elevations in any of the single probiotics or the probiotic formulation. Notably, the probiotic formulation demonstrated a significantly lower level of total glucose (31.0% increase above untreated controls) compared to both the Lp8826 and Bi702255 groups. Finally, total triglycerides were significantly elevated in the HFD-fed Drosophila controls by 187% (FIG. 1f). This increase was significantly higher than Drosophila treated with LfS221, Bi702255 and the probiotic formulation, which demonstrated 119.0%, 91.2% and 32.3% increases in total triglycerides, respectively. Notably, the probiotic formulation demonstrated the smallest increase in total triglycerides compared to any of the single probiotic treatments indicating a cumulative effect. Again, although some of the individual probiotics demonstrated similar ability to reduce the physiological parameters of diet-induced obesity, none were as robust as the probiotic formulation at reducing all of the physiological parameters of obesity.

Various genetic markers of insulin signaling, fatty acid metabolism and their underlying signaling pathways were assessed by real-time PCR. All of the reported values are expressed as percent change compared to control flies with the same probiotic treatment but on a normal diet. Of particular importance, expression of the insulin receptor (InR) gene was elevated by 148.1% in control flies on a HSD, which was significantly higher than flies treated with Lp8826 (7.0% increase) or the probiotic formulation (6.5% increase). Similarly, the insulin effector molecules {Drosophila insulin-like peptides; dilps) were significantly elevated 174.7% (dilpl) and 1 18.2% (dilp3) in control flies fed on a HSD. The elevation of dilp2 in control Drosophila was significantly higher than flies treated with Lp8826 (13.0% increase), Lf5221 (24.3% increase) or the probiotic formulation, which actually demonstrated a decrease in dilp2 expression by S8.3%, significantly lower than any of the other individual probiotics. Similarly, the probiotic formulation significantly reduced dilp3 expression by 37.2%, which was significantly lower than any of the individual probiotic treatments. This indicates that the probiotic formulation is far more effective at reducing the HSD-induced genetic variations contributing to insulin resistance than the individual probiotics, which only had mild and inconsistent effects on the key markers of diabetes.

Analyzing the results even more closely, the probiotic formulation also significantly impacted pathways downstream of insulin signaling, such as the canonical Akt-TOR-FOXO pathway. dAkt was significantly elevated by 241.0% in HSD control flies, which was significantly higher than each of the single probiotic treatments Lp8826 (33.3% increase), Lf5221 (83.6% increase) and Bi702255 (130.4% increase). The probiotic formulation completely attenuated the increase in dAkt signaling in HSD-fed flies compared to the normal control diet, which was significantly lower than each of the individual probiotics. dTOR was also significantly elevated in control Drosophila fed a HSD diet (164.1%). This elevation was significantly reduced by each of the individual probiotic formulations Lp8826 (1.5% increase), LfS221 (3.0% decrease) and Bi702255 (68.3% increase) as well as the probiotic formulation which completely rescued the elevation in dTOR expression. A similar phenomenon was noted with the transcription factor dFOXO, which was significantly reduced by 62.S % by the HSD diet, a decrease which was significantly lower than LfS221 (4.7%) and especially the probiotic formulation which again completely rescued the decrease of dFOXO expression.

A similar trend was observed in the regulation of fatty acid oxidation genes in Drosophila fed a HFD. Several genetic markers of fatty acid synthesis (SREBP, ACC, FAS), gluconeogenesis (PEPCK) and the regulation of triglyceride content (E78 and LSD) were assessed by real-time PCR. Acetyl-CoA carboxylase (ACC) was elevated by 79.9% in control flies fed a HFD, which was significantly higher than Drosophila treated with either Lf5221 (0.8% increase) or Bi702255 (27.8% increase). The probiotic formulation rescued the expression of ACC, which was significantly lower than each of the individual probiotics. Fatty acid synthase (FAS) was also significantly elevated in control Drosophila fed a HSD by 82.1%. This elevation was significantly higher than Drosophila treated with either Lf5221 (26.7% decrease) or the probiotic formulation which rescued the expression of FAS in HFD-fed Drosophila. Phosphoenolpyruvate carboxykinase (PEPCK) was significantly upregulated in control Drosophila fed a HFD by 239.8%. This elevation was significantly higher than any of the individual probiotics Lp8826 (36.8% increase), Lf5221 (49.9% increase) and Bi702255 (165.8% increase); however PEPCK expression was completely rescued by the probiotic formulation, which was significantly lower than any of the individual probiotics.

Looking at the upstream regulatory factors, sterol regulatory element binding protein (SREBP), which regulates the expression of all the aforementioned fatty acid oxidation genes, was significantly elevated in control Drosophila fed a HFD by 165.0%. This elevation was significantly reduced by each of the individual probiotics Lf5221 (109.1% increase), Lp8826 (51.7% increase) and Bi702255 (42.1% decrease) as well as the probiotic formulation (114.2% increase). dTOR was also significantly upregulated in control Drosophila (93.7%) which was significantly higher than each of the individual probiotics Lp8826 (52.0% increase), Lf5221 (5.9% decrease) and Bi702255 (29.3% increase) and was completely rescued by the probiotic formulation. Ecdysone-induced protein 78 (E78) is a nuclear receptor in Drosophila similar to Rev-erba and PPARγ, which is known to be involved in energy regulation in Drosophila. E78 was elevated by 253.6% in control HFD treated Drosophila, which was significantly reduced by LfS221 (53.7% increase) and Bi702255 (84.1% increase) while rescued by Lp8826 and the probiotic formulation. Finally, Drosophila Lipid Storage Droplet (LSD) 2 controls the storage of triglycerides in the fat body of flies. LSD2 was elevated by 169.8% in control HFD Drosophila which was only reduced in in Drosophila treated with the probiotic formulation (7.5% increase). Examination of the genetic markers of diabetes and obesity, a similar phenomena was observed as the physiological markers in that the probiotic formulation more robustly and consistently rescued the disease markers, whereas the individual probiotics only had an inconsistent effect on the gene expression.

Conclusion

The individual probiotic bacteria tested (Lp8826, LfS221 and Bi702255) all had some efficacy on a variety of markers of diet-induced diabetes in Drosophila; however, their effects were inconsistent among all the parameters tested and limited to one or two of the underlying genetic pathways. Insulin signaling is a dynamic multi-pathway system that has a natural robustness, hence the greatest benefit comes from unanimously attenuating the canonical signaling pathway (InR-Akt-TOR-FOXO) while controlling the expression of insulin and insulin effector factors (dilps). Similarly, with fatty acid oxidation, there are several levels of regulation controlling the accumulation of fatty acids in the adipose tissue, which are most effectively controlled by the simultaneous targeting by the probiotic formulation. In mis case, the probiotic formulation provided a more complete, consistent and reliable effect on the physiological and genetic parameters of diabetes and obesity indicating that the exemplary Lp8826, Lf5221 and Bi702255 formula as provided herein is better at treating the entirety of the disease pathology than a single probiotic bacterium.

Example 2: Exemplary Compositions for Treating Inflammation

The following example demonstrates the efficacy of exemplary probiotic formulations for treating or ameliorating inflammation.

To test the inflammatory resistance of Drosophila melanogaster, they were treated with a probiotic formulation and challenged with an oral bacterial infection of gram-negative (E. coli) or gram-positive (S. aureus) bacteria. Basic immune parameters including survivability and production of anti-microbial agents are assessed along with genetic markers of immune activation.

Methods

Bacterial Strains

Two pathogenic strains, Escherichia coli ATCC 8739 (gram negative pathogen) and Stapphylococcus aureus ATCC 10832 (gram positive pathogen) were kept at −80° C. in a 20% glycerol stock until streaked onto nutrient agar plates containing 3 g L beef extract and 5 g L peptone adjusted to pH 7.0 (Nutrient Broth; NB). Colonies were seeded into NB and grown for 18 h at 37° C. with shaking (2S0 rpm). Overnight colonies were seeded at 1% inoculum in NB and the bacterial suspension was isolated for either incorporation into the Drosophila media or to be spread on nutrient-agar plates.

Oral Infection

Flies were transferred to media supplemented with probiotics (Lp8826, Lf5221, Bi702255 or the probiotic formulation) immediately after eclosion. After 10 days, flies were transferred to media containing both the probiotic therapy and either E. coli or S. aureus at doses of 0, $1 \times 10^9$, $5.0 \times 10^9$ or $1.0 \times 10^{10}$ CFU/ml. Survivability was measured in triplicate for 10 flies isolated on S. aureus or E. coli inoculated media and the time it took for 50% of the flies to die was recorded. Otherwise, flies were kept on the media for 5 days (time for approximately 50% death rate in control groups), after which flies were removed, rinsed in a 10% bleach solution and 3× in distilled water before being placed at −80° C. for further processing.

Agar Disk Diffusion Assay

To assess the flies' direct ability to inhibit the growth of both E. coli and S. aureus, hemolymph from flies reared for 10 days on media containing the probiotic therapy was placed on a lawn of either S. aureus or E. coli on TSC-agar plates. To isolate hemolymph, 50 flies were pierced with a fine needle in the thorax region and placed in a small Eppendorf tube perforated with several holes, situated in a larger Eppendorf tube. The pierced flies were centrifuged at 3000×g, at 4° C. for 20 min to remove sufficient hemolymph for analysis. The hemolymph (20 μl) was diluted to 50 μl with sterile saline water and pipetted onto a 5 mm sterile circle of filter paper situated on the nutrient-agar plates freshly spread with 100 μl of overnight S. aureus or E. coli solution. The inoculated plates with the hemolymph saturated filter paper were placed at 37° C. for 24 h and the zone of inhibition was measured. Each treatment was run in triplicate on separate nutrient-agar plates.

Real-Time PCR mRNA isolation, cDNA synthesis and real-time PCR was conducted as described in the metabolic section. Specific primers used for the analysis of inflammatory markers are outlined in Table 2:

TABLE 2

Primers for the analysis of inflammatory markers

| Gene Name | Sequence (5'-3') | SEQ ID NO: | Annealing Temp |
|---|---|---|---|
| Duox | F: GCTGCACGCCAACCAC AAGAGACT | SEQ ID NO: 27 | 54° C. |
| | R: CACGCGCAGCAGGATG TAAGGTTT | SEQ ID NO: 28 | |
| IMD | F: TCGAATGCCAATAATC TGCA | SEQ ID NO: 29 | 52° C. |
| | R: CGCGATGCTGGGACTC CCAC | SEQ ID NO: 30 | |
| Relish | F: TGGGAGGCATACGCAA AGT | SEQ ID NO: 31 | 55° C. |
| | R: CAATTACGCTCCGTGG CTTG | SEQ ID NO: 32 | |
| Attacin A | F: GGCCCATGCCAATTTA TTCA | SEQ ID NO: 33 | 56° C. |
| | R: CATTGCGCTGGAACTC GAA | SEQ ID NO: 34 | |
| Diptericin | F: AGGTGTGGACCAGCGA CAA | SEQ ID NO: 35 | 56° C. |
| | R: TGCTGTCCATATCCTC CATTCA | SEQ ID NO: 36 | |
| Drosocin | F: GCACAATGAAGTTCAC CATCGT | SEQ ID NO: 37 | 56° C. |
| | R: CCACACCCATGGCAAA AAC | SEQ ID NO: 38 | |

Results

Survivability

Figure 2A:
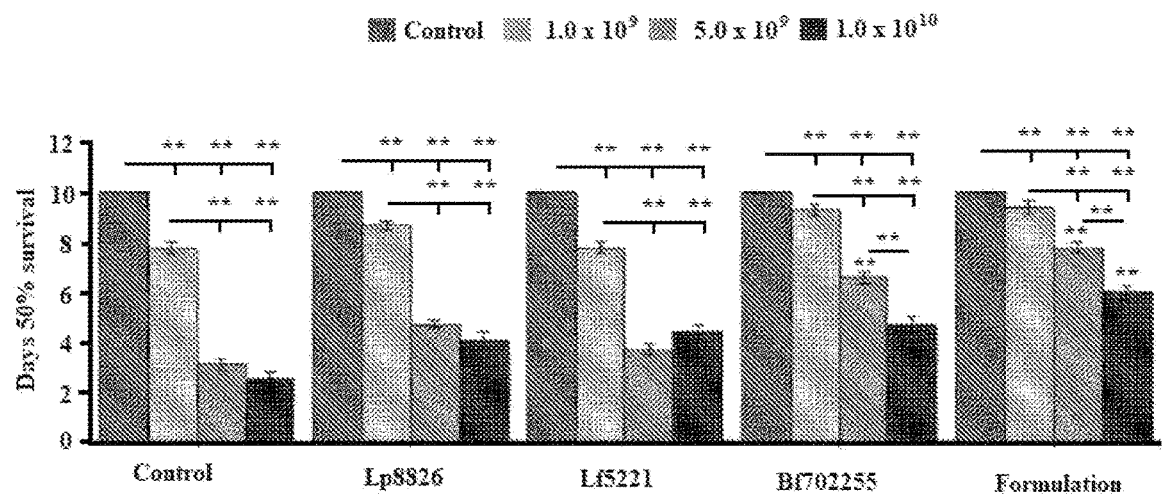

As expected, there was a dose-dependent decrease in survivability in the control groups fed E. coli or S. aureus. As the concentration of E. coli was raised from $1.0\times10^9$, $5.0\times10^9$ to $1.0\times10^{10}$ CFU/ml, the 50% survivability in the control group dropped 7.8, 3.1 to 2.5 days, respectively (FIG. 2a; p<0.01). In all treatment groups, there was a dose-dependent decrease in survivability, albeit to different extents depending on the group. There was little variation in the E. coli 1.0×109 CFU/ml group between different treatments, however in the $5.0\times10^9$ CFU/ml E. coli group, there were significant increase in the survivability for the Bi702255 and probiotic formulation groups (FIG. 2a; p<0.01). In the 1.0×10 CFU/ml group, there were significant increases in survivability only in the triple formulation group (FIG. 2a, p<0.01) indicating a synergistic effect in immune effectiveness against an E. coli challenge.

Figure 2B:
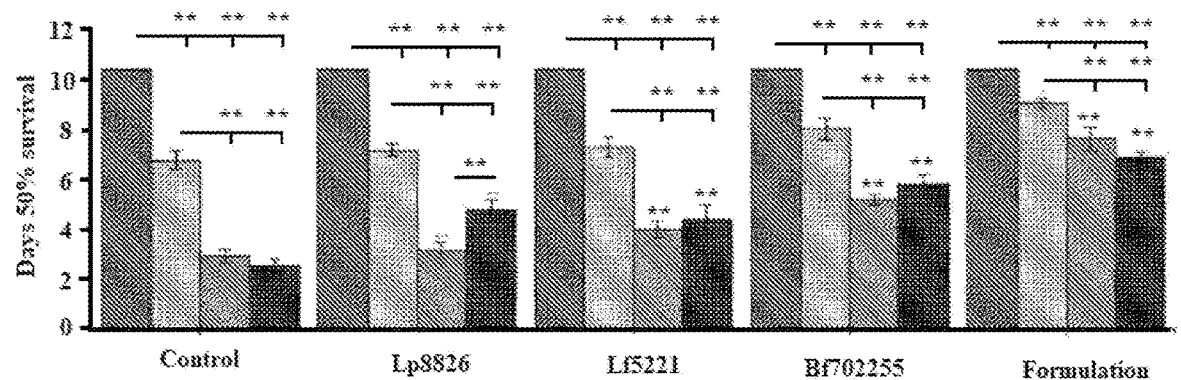

Survivability to S. aureus oral infection was similar to Drosophila challenged with E coli. As the concentration of S. aureus infection in the control group was raised from $1.0\times10^9$, $5.0\times10^9$ to $1.0\times10^{10}$ CFU/ml, the 50% survivability dropped from 6.5, 2.8 to 2.4 days, respectively (FIG. 2b; p<0.01), although there was no significant difference between the $5.0\times10^9$ and $1.0\times10^{10}$ CFU/ml groups. Like E. coli, there was no significant difference in the survivability in the $1.0\times10^9$ CFU/ml dosage group between treatment groups. However, there was a significant increase in survivability in the $5.0\times10^9$ CFU/ml group when treated with Bi702255 or the probiotic formulation (FIG. 2b, p<0.01). There were also significant increases in survivability in the $1.0\times10^{10}$ CFU/ml dosage group for all treatment groups with the probiotic formulations being slightly more effective than the single probiotic treatment groups.

An agar disk diffusion assay was conducted with Drosophila pretreated with each of the respective probiotic treatments, exposed to plates containing a lawn of either E. coli or S. aureus. Hemolymph from Drosophila was isolated, and spotted on a small filter paper disc situated on the inoculated plate. On the E. coli plate, there was a significant increase in the zone of inhibition in the Lp8826, Bi702255, and probiotic formulation groups compared to the untreated controls (FIG. 2c, p<0.01). In addition, the probiotic formulation created a larger zone of inhibition than each of the individual probiotic groups indicating a synergistic effect. Similarly, for the agar plates inoculated with S. aureus, there was a significant increase in the zone of inhibition for all treatment groups (FIG. 2d; p<0.05) with the probiotic formulation group having a larger zone of inhibition compared to the Lp8826 and Lf5221 group. Overall, the probiotic formulation against both the E. coli and S. aureus challenge were synergistically more effective than the single probiotic species, indicating their potential to inhibit both gram-negative and gram-positive bacterial insults.

To assess the immune activity on the molecular level, expression of several immune-activated genes was assessed by real-time PCR. Based on the survivability data presented, the optimal acute inoculation concentration of both E. coli and S. aureus was chosen at $5.0\times10^9$ CFU/ml, and the genetic analysis only for this concentration is shown. To investigate the upstream and first-response elements of the Drosophila immune response, the expression of Duox, IMD and Relish was determined. Dual oxidase (Duox) is a member of the intestinal nicotinamide adenine dinucleotide phosphate (NADPH) oxidase family involved in several aspects of gut-microbe interactions such as microbial clearance, intestinal epithelial cell renewal and redox-dependent modulation of signaling pathways (see e.g., Kim & Lee, 2014). In response to invading pathogens and signaling from the Drosophila gut microbiota, Duox produces ROS particles eliminate those pathogens in an indiscriminate arm of the innate immune system. Typically, duox expression is elevated upon immunological insult and this is precisely what was observed in the control group of both the *E. coli* challenged *Drosophila* (197.1% increase; FIG. 2e) and *S. aureus* challenged *Drosophila* (814% increase; FIG. 2f). In the *E. coli* treated *Drosophila*, all treatment groups significantly reduced the level of Duox expression where the probiotic formulation group had a significantly lower Duox expression than the Lf5221 group (FIG. 2e; p<0.01). Similarly, in the *S. aureus* group, all of the treatment groups significantly reduced Duox expression (FIG. 2f; p<0.01).

The immune-deficiency (IMD) factor in *Drosophila* is strongly activated downstream of gram-negative bacterial infection and works to induce expression of effector molecules including the cytokine-like Relish and AMPs Attacin A and Diptericin. As expected, there was a strong upregulation of IMD expression in the *E. coli* treated controls (165.4% increase; FIG. 2g; p<0.01). The IMD expression was significantly downregulated in all treatment groups with the probiotic formulation having a significantly larger effect than the Lp8826 and Lf5221 groups. After *S. aureus* treatment, there was a significant 41.1% elevation of IMD expression in control *Drosophila*, which was significantly higher than the Lp8826, Bi702255 and probiotic formulation groups (FIG. 2h; p<0.05). Notably, the probiotic formulation reduced ID expression to a greater extent than both the Lf5221 and Bi702255 groups.

The antimicrobial peptides (AMPs) are the effector molecules for the *Drosophila* immune system and have several modes of action due to their amphipathic nature, but generally target a particular subset of invading pathogens. For example, Defensin targets gram-positive bacteria while Attacin and Diptericin target gram-negative bacteria. In the *E. coli* challenged flies, there was a strong increase in Attacin A expression in the control group (232.7% increase) as expected for a gram-negative bacteria (FIG. 2i, p<0.01). This increase was significantly higher than any of the treatment groups. There was also a significant elevation of Attacin A expression in the *S. aureus* treated control group (183.9% increase; FIG. 2j; p<0.01), which was significantly higher than any of the treatment groups. Diptercin expression in the *E. coli* control group was strongly elevated in as expected (251.2% increase, FIG. 2k; p<0.01) and this elevation was significantly higher man any of the treatment groups. Notably, Diptericin expression in the probiotic formulation group was significantly lower than the Lp8826 treatment group. In the *S. aureus* control group, there was also a significant elevation of Diptercin expression (115.1% increase), which was greater than both the Bi702255 and probiotic formulation expression (FIG. 2l; p<0.01). Finally, Defensin expression was assessed and it was found to be mildly upregulated in the *E. coli* inoculated control group (41.0%; FIG. 2m). This was significantly higher than the Lp8826, Lf5221 and probiotic formulation groups which actually reduced Defensin expression to levels less than the control. In the *S. aureus* control group, there was a very significant increase in Defensin expression (329.9%; FIG. 2n) as would be expected for a gram-positive bacterial challenge. This elevation was significantly higher than any of the treatment groups where Defensin expression in the Bi702255 group was the lowest, being at or near the level of the baseline.

Conclusions

The increased survivability of flies treated with the exemplary probiotic formulation as provided herein coupled with a reduced expression of immune effector genes indicates that the gut microbiota in the treatment groups was favorably altered to make a non-permissive environment for the growth of pathogenic organisms. This could include mechanisms such as reduced intestinal permeability or the outcompeting of good bacteria for growth resources over the pathogenic strains.

Example 3: Exemplary Compositions for Treating Acute Stress

The following example demonstrates the efficacy of exemplary probiotic formulations for treating or ameliorating acute stress.

Methods:

*Drosophila* and Oxidative Challenge

Wild-type *Drosophila melanogaster* (Oregen®) were reared on conventional cornmeal-yeast-sucrose media as described in previous sections. Immediately after eclosion, flies were transferred to media containing $3.0 \times 10^9$ CFU/ml of Lp2389, Lf5221, Bi702255, or the Triple formulation. After ten days, flies were transferred to either control media or media containing 3.0% hydrogen peroxide to simulate an acute oral oxidative stress. After 3 days when approximately 50% mortality was observed in the control-hydrogen peroxide group, flies were anesthesized and immediately homogenized in Tris-EDTA-TRITON X-100 buffer to release intracellular anti-oxidant enzymes. Tests for several enzymes were conducted:

Total Oxidants

Total oxidants were assayed using 2'-7'-dichlorofluorescein diacetate (DCFA) (Sigma, Oakville, ON) as outlined by Hosamani et al. (Archives Insect Biochem). Briefly, 20 µl of fly homogenate was mixed with 170 µL, of Locke's buffer. Following, 10 µl of 1 mM DCFA solution was added to each well and after 3 min incubation, fluorescently read at 474 nm excitation and 530 nm emission wavelengths.

Superoxide dismutase (SOD) Assay

SOD was assayed using xanthine-xanthine oxidase to generate superoxide radicals and nitrotetrazolium blue (NBT) reduction as an indicator of superoxide production (Mockett 2002, Methods Enzymol). Briefly, the working solution consisted of 1 10 µl of potassium phosphate buffer with 20 mg/ml BSA, 6.2 µl catalase (40 U/ml), 6.2 µl of NBT and SO µl of xanthine (1.8 mM). To the working solution, 7.S µl of sample and 20 µl of xanthine oxidase (XOD, S U/ml) was added and incubated at 37° C. for 20 min in the dark with agitation to allow colour to develop. Absorbance of reduced NBT was recorded at S70 nm and compared to a standard curve of SOD.

Glutathione Peroxidase (GPx) Activity

GPx activity was assessed based on the oxidation of glutathione (GSSG), which was constantly supplied by an excess of glutathione reductase (GR). To measure GPx activity the consequent reduction of the cosubstrate NADPH was monitored at 340 nm as outlined in (Weydert & Cullen 2010 Nature Protocols) with modifications. Briefly, a GPx buffer was made containing 0.S M sodium phosphate (pH 7.2), 100 mM EDTA and 1.1 mM sodium aztde. The GPx assay buffer consisted of 1.33 mM of GSSH and 1.33 U/ml GR in GPx buffer. The assay solution consisted of 160 µl of GPx assay solution, 10 µl of NADPH (5 mM), 20 µl hydrogen peroxide (0.5%) and IS µl of homogenate. The absorbance at 340 nm was monitored for 3 min and the linear portion of the curve was assessed for GPx activity.

Lipid Peroxidation

The level of lipid peroxidation was assessed as bound malondialdehyde (MDA) was hydrolyzed in the presence of butylated hydroxytolene (BHT) as adapted from Gerard-Monnier 1998, *Chem Red Toxicol*. The reaction solution contained 10 mM of 1-methyl-2-phenylindole in a 3:1 mixture of acetonitrile:methanol. To 120 µl of this solution, 20 µl of sample and 40 µl of 37% HCl was added and allowed to react at 100° C. for 60 min. The absorbance of the resulting solution was measured at 550 run and compared to MDA standard solution.

Results

Figure 3A:
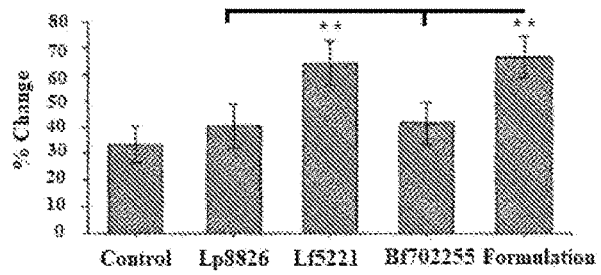
Figure 3B:
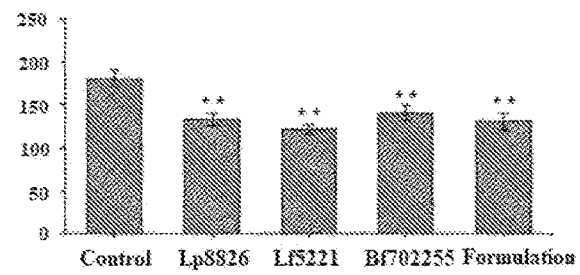
Figure 3C:
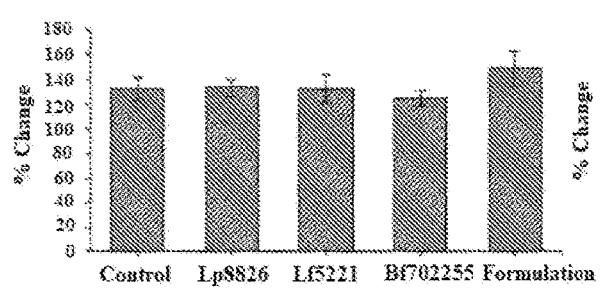

After transfer to media containing 3% hydrogen peroxide, flies acclimatized on untreated media demonstrated a 50% mortality after 3.4 days, which is represented as a 33.3% change compared to untreated controls (FIG. 3a; p<0.01). This reduction in survivability was significantly elevated by both Lf5221 and the probiotic formulation treatment (p<0.01). Notably, the probiotic formulation was more efficient than Lp8826 and Bi702255 at improving the survivability of *Drosophila* treated with the hydrogen peroxide. The measure of total oxidants was significantly reduced by all treatment groups, with the probiotic formulation not having a significant improvement compared to the individual probiotic treatments (FIG. 3b; p<0.01).

Figure 3D:
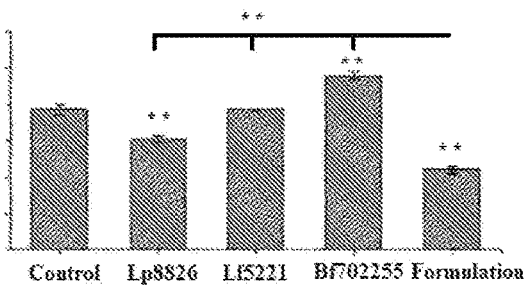
Figure 3E:
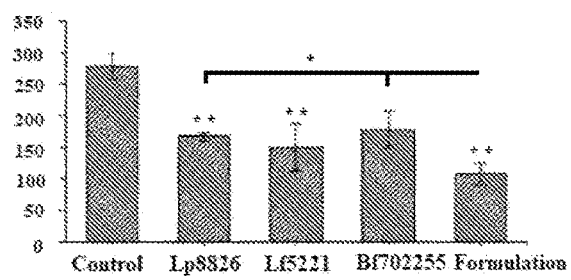

Activity of the antioxidant enzymes reflects both the ability of the *Drosophila* to deal with the oxidative challenge, but also the level of inherent protection due to the probiotic treatment. SOD activity, which was mildly elevated in the control hydrogen peroxide treated group (132.3%), was not affected by any of the probiotic treatments. In contrast, glutathione peroxidase activity, which significantly elevated in the control hydrogen peroxide treated group (192.9%), was significantly reduced by the Lp8826 and probiotic formulation treatments, with the probiotic formulation having a greater effect than any of the individual probiotic groups, including Lp8826 (FIG. 3d). Finally, LPO levels which were significantly elevated in the control hydrogen peroxide treated group (278.4%), were significantly reduced by Lp8826, Lf5221 and the probiotic formulation, with the probiotic formulation completely rescuing the levels of lipid peroxidation (FIG. 3e).

Conclusions

An acute oxidative stress challenge reduced *Drosophila*'s survivability and elevated the levels of total oxidants, lipid peroxidation along with the activity of two key anti-oxidant enzymes, SOD and GPx. Administration of an exemplary probiotic formulation as provided herein was the most effective at increasing survivability to the oxidative stress and reducing total oxidants and lipid peroxidation levels; however, the exemplary probiotic formulation also showed beneficial effects on elevating the activity of SOD and GPx anti-oxidant enzymes.

Example 4: Exemplary Compositions for Treating Neurodegenerative Diseases

The following example demonstrates the efficacy of exemplary probiotic formulations for treating or ameliorating, or slowing the progress of or slowing the onset of a Neurodegenerative Disease, including Alzheimer's disease (AD) and Parkinson's disease (PD).

We show that through modification of the gut microbiota with the probiotic formulation that the three main environmental causes of neurodegeneration (inflammation, oxidative stress and faulty metabolism) can be alleviated and hence improve the molecular markers of the disease. This unique construction utilizes the mechanisms of the gut-brain-axis to sustainably and safely treat the pathology of neurodegeneration at its source.

Methods

*Drosophila* Genetic Models of Parkinson's and Alzheimer's Disease

Genetic models of PD and AD will be modeled in *Drosophila* using the UAS (upstream activation sequence)-GAL4 system. For PD, a mutant form of human o synuclein with high aggregability (UAS-A30P kindly donated from Dr. Mel Feany, Harvard, MA) will be expressed in *Drosophila* neurons using the neuronal-specific e/v-GAL4 driver element (Indiana University, Bloomington, IN) by mating virgin female A30P flies with male e/ov-GAL4 flies. The expression of A30P-a-synuclein induces a PD phenotype after 30 days, see e.g., Feany & Bender, 2000). AD will be modeled by expression of the UAS-(-secretase) BACE1-APP gene (Indiana University, Bloomington, IN) within neurons with the elav-GAL4 driver. *Drosophila* have an endogenous APP ortholog and γ-secretase machinery but the *Drosophila* β-secretase has low activity and *Drosophila* APP lacks homology in the region corresponding to the harmful Aβ peptide, see e.g., Luo, Tully, & White, 1992. However, expression of human BACE1 produces Aβ-like particles instigating AD pathogenesis in 3-4 weeks.

Following eclosion, flies will be placed on media supplemented with either control, Lf5221, TFLA or the probiotic formulation. Bottles will be changed every 3-4 days to prevent the build up of wastes and mould.

Physiological Tests

Total lifespan and motility will be assessed in flies afflicted with both PD and AD to determine their overall fitness with age. Lifespan was calculated by first separating 10 flies into isolated vials and tallying daily the number of flies alive with the respective treatment. Each test was conducted with 5 separate vials of 10 flies. Motility was assessed using the negative geotaxis test. Briefly, 10 flies were lightly anesthetized and transferred to an empty vial 15 cm in height. After 45 min of acclimatization, flies were gently tapped to the bottom of the vial and the time it took for SO % of the flies to reach a 10 cm mark on the vial was recorded. Each test was repeated with three independent samples of ten flies.

Metabolic Tests

To assess the metabolic activity of the AD and PD flies, tests are previously described for the total glucose and total triglycerides will be conducted (see section on diabetes obesity).

Acetylcholine Esterase Activity Assay

ACh activity was assessed in fly head homogenates using a modified Ellman's method, see e.g., Benabent, Vilanova, Sogorb, & Estevez, 2014. Twenty fly heads were homogenized in 200 µl of ice-cold Tris-EDTA-TRITON X-100 in the presence of protease inhibitors followed by centrifugation at 10,000 rpm for 2 min to remove body fragments. 5 µL of homogenate was added to 100 of 10 mM acetylthiocholine and incubated at 37° C. for 10 min to run the enzymatic reaction. The reaction was stopped with 50 µL, of 6 mM Dithiobis(2-nitrobenzoic acid). After diluting with another 50 µL. of buffer solution, absorbance was read at 410 nm and total ACh activity amounts was normalized to total sample protein.

Total Amyloid Content

Total amyloid content was assessed using the Thioflavin T (Tht) assay protocol, see e.g., Khurana et al., 2005. Similar as the ACh activity assay, 20 fly heads were homogenized in a Tris-EDTA-TRITON X-100 buffer with protease inhibitors and centrifuged to remove cellular debris. A stock solution of Tht was made by diluting 8 mg of Tht into 10 mL of PBS, pH 7.0. For the working solution, the Tht stock solution was diluted 1:5 into PBS and 2 μL of sample homogenate was added to 198 μL, of working Tht solution. Fluorescence was measured at 440 nm excitation/482 nm emission and the total quantification of amyloids was normalized to total sample protein.

Dopamine Quantification

Dopamine quantification will be assessed using a commercial Fast-Dopamine ELISA kit (LDN; Nordhom Germany) with some modifications. Homogenates of 40 fly heads will be made in PBS with assay buffer (1 M HCl) before addition to the elution plate. The remaining procedure follows the manufacture's instructions.

Results

The pathology of AD and PD were measured through broad physiological parameters (lifespan and motility) as well as specific neurological markers of the disease. In AD flies, control flies had only a 40% survival rate at day 30 while flies treated with both Lf5221 had a non-significant decrease in survivability (30% at day 30) while the probiotic formulation significantly increased survivability to 60% (FIG. 4a; p<0.01). A similar trend was observed for PD flies. Control flies had a survival rate of 40% while there was no change after Lf5221 treatment, the probiotic formulation increased survivability to 60% (FIG. 4b; p <0.01). Motility is a good measure of overall physical health in aging Drosophila. Over time, AD control flies had an increased time for the negative geotaxis test from 6.4 s, 7.5 s, 8.2 s, 12 s at days 0, 10, 20 and 30 (FIG. 4c; p<0.01). Although there were significant elevated in the negative geotaxis time for both the Lf5221 and probiotic formulation groups starting at day 20, the probiotic formulation had a significantly lower time for the negative geotaxis time at day 30 compared to either the control of the Lf5221 group (p<0.01). In the PD flies, the control group also had a steady increase in time to complete the negative geotaxis test ranging from 5.7 s, 8.1 s, 10.1 s and 14.3 s at day 0, 10, 20 and 30, respectively (FIG. 4d; p<0.01). There were significant elevations in the Lf5221 group starting at day 30 and in the probiotic formulation group starting at day 20 (p<0.01). At day 10, 20 and 30 the time for negative geotaxis for the Lf5221 and probiotic formulation groups was significantly lower than in the control group (p<0.01).

To measure the specific disease pathology of AD, the level of Aβ plaques and ACh activity was measured in Drosophila head homogenates over time. As expected, there was a steady increase in the amount of Aβ plaques in the control group with a 30% increase by day 30 (FIG. 4e; p<0.01). There were significant elevations in both the Lf5221 (26%) and probiotic formulation groups (21%) at day 30 with the Lf5221 being significantly lower than the control group (p<0.05) the probiotic formulation lower than the both the Lf5221 and control group (p<0.01). ACh activity, as expected, was significantly reduced in the control group at day 20 and 30 (FIG. 4g; p<0.01). Lf5221 treatment significantly increased ACh activity at day 20 and day 30 while the probiotic formulation significantly elevated ACh activity at day 20 and 30 compared to both Lf5221 and the control group (p<0.01).

To measure the progression of PD, dopamine levels in the head homogenates were measured over time. As expected, the total amount of dopamine in the control group steadily decreased from 0.67, 0.61, 0.55 to 0.52 μg mg protein from day 0, 10, 20 to 30, respectively (FIG. 4F; p<0.01). By day 30, dopamine levels were significantly elevated by both the Lf5221 and probiotic formulation treated groups (p<0.01).

Variation in the basic metabolic parameters was assessed in aging AD and PD flies. In AD Drosophila, the level of total glucose in control Drosophila increased to 1.24 μg/mg protein at day 30, a 60% increase compared to flies at day 0 (FIG. 4h; p<0.01). Although there were also significant elevation sin the Lf5221 and probiotic formulation groups at day 30, the increase in the probiotic formulation group was significantly less than the control and LfS221 group (p<0.05). Total glucose in PD flies was also significantly increased by day 30 to 1.1 1 μg mg protein, a 27% increase compared to day 0 (FIG. 4i; p<0.01). The elevation in control Drosophila was significantly higher than both Lf5221 and the probiotic formulation treated groups (p<0.05). Total triglyceride levels in the AD control Drosophila had a non-significant 20% increase by day 30 (FIG. 4j; p>0.05). However, the probiotic formulation significantly lowered the total triglyceride levels at both day 20 and 30 compared to the control and Lf5221 groups (p<0.05). In PD control Drosophila, there was a significant increase in total triglycerides at day 10, 20 and 30 with an increase of 88% by day 30 (FIG. 4k, p<0.01). At day 30, the elevation in Lf5221 and the probiotic formulation were significantly lower than the control group with the probiotic formulation being more effective than Lf5221 at reducing total triglyceride levels (p<0.01).

The levels of oxidative stress were measured by measuring the total number of oxidants, peroxidation and the activity of the antioxidant resistance enzymes. In AD Drosophila, there was a 30% increase in the total oxidants of control Drosophila from day 0 to day 30 (FIG. 4l; p<0.01). The level of total oxidants in Lf5221 treatment AD flies was reduced by 5% at day 30 while the probiotic formulation reduced total oxidants by 11%: both reductions were significantly lower than the increase in control Drosophila. Superoxide dismutase activity was significantly lowered by 36% in control AD Drosophila, and remained low at day 30 in the Lf5221 (41% decrease) and probiotic formulation (38% decrease) treated groups. In contrast, glutathione peroxidase activity was relatively unchanged in the control Drosophila by day 30 (9% increase); however, there was a slight increase in GPx activity by LfS221 treatment (34%) and a massive increase by the probiotic formulation (257% increase) at day 30 (FIG. 4l; p<0.01). Finally, the LPO levels in control AD Drosophila were significantly elevated by 38%. There was also a significant rise in LPO levels with the Lf5221 treatment (62%); however the probiotic formulation significantly lowered LPO levels (41% decrease) compared to both the control and Lf5221-treated Drosophila (FIG. 4l; p<0.01).

Similar effects were seen in the PD Drosophila. In the control group, by day 30 there was a 24% increase in total oxidants, an increase which was rescued by LfS221 treatment and reduced by the probiotic formulation by 20% (FIG. 4m; p<0.01). Again, SOD levels were slightly reduced in all groups in the aging PD Drosophila. GPx activity was significantly lower (15%) by day 30 in control Drosophila though increased by Lf5221 (34% increase) and very effectively by the probiotic formulation 252% (FIG. 4m, p<0.01). Finally, LPO levels were significantly elevated in the control group at day 30 to 37%, which was rescued by the probiotic formulation (FIG. 4m; p<0.01).

The activity of the immune system was measured through a direct measure of antimicrobial agent production using an agar diffusion test. The zone of inhibition was recorded as the diameter of the zone. In AD control *Drosophila*, there was a significant decrease in the zone of inhibition in aging *Drosophila* starting at day 10 indicating that the *Drosophila* produced less antimicrobial agent (FIG. 4*n*; p<0.01). In contract, *Drosophila* treated with Lf5221 only observed a reduction in the zone of inhibition at Day 30 while *Drosophila* treated with the probiotic formulation had no reduction in the zone of inhibition indicating that probiotic treatment significantly elevated the production of antimicrobial agents, and hence immune tolerability in aging AD *Drosophila* (FIG. 4*n*; p<0.01). Similarly in PD *Drosophila*, control flies had a significant decrease in the zone of inhibition beginning at Day 10 (FIG. 4*o*; p<0.01). Treatment with either Lf5221 or the probiotic formulation delayed any reduction in the zone of inhibition to Day 30 (FIG. 4*o*; p<0.01). Expression of several immunological genes was also examined to determine the specific immune response in aging AD and PD flies. In control AD *Drosophila*, there was a significant decline in the expression of Duox and a significant increase in the expression of IvD and the AMPs Attacin A, Defensin and Diptericin (FIG. 4*p*; p<0.01). Duox expression was significantly elevated by the probiotic formulation while IMD expression was lowered by both Lf5221 and the probiotic formulation (FIG. 4*p*; p<0.05). The probiotic treatment had less effect on the expression of the AMPs, though the probiotic formulation significantly reduced the expression of Defensin. In control PD *Drosophila*, there were significant reductions in the expression of Duox and IMD while the AMPs were similarly elevated (FIG. 4*q*; p<0.01). Treatment with Lf5221 only had a reducing effect on the expression of Diptercin while the probiotic formulation significantly lowered the expression of IMD, Defensin and Diptercin (FIG. 4*q*; p<0.01). With aging, it is known that the efficiency of the *Drosophila* immune system decreases, while contributes to an increase in pathogenic load. This would explain the reduction in the indiscriminate immunological genes (Duox and IMD) while an increase in the pathogen-specific factors (AMPs).

Figure 4R:
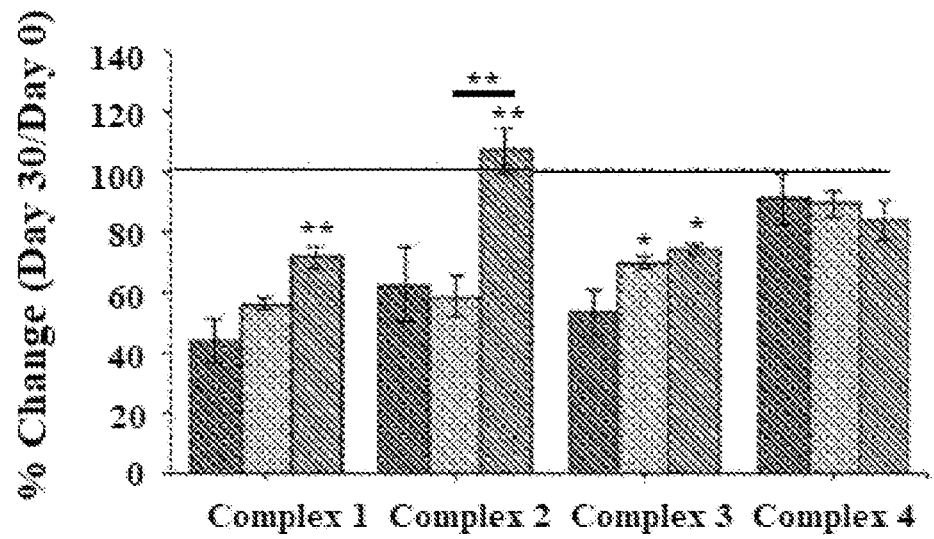
Figure 4S:
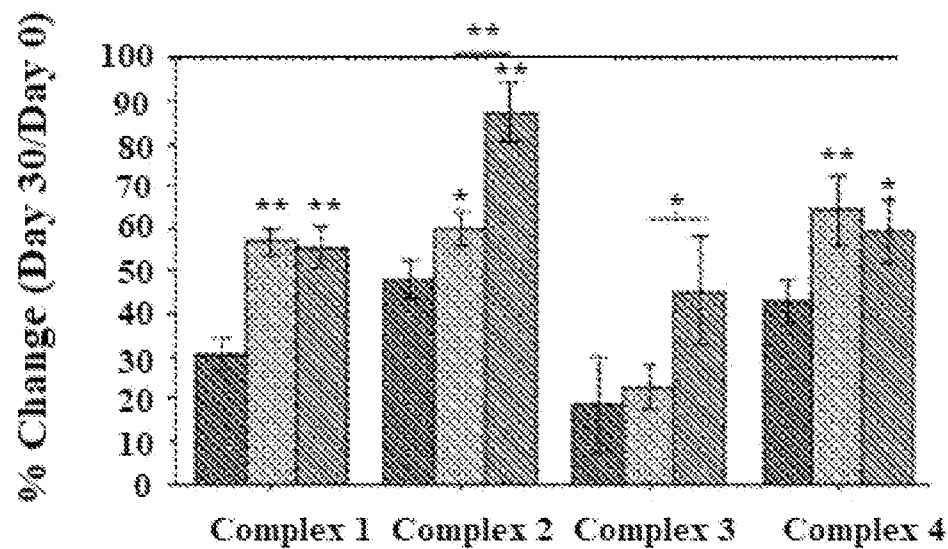

Finally, the activity of the individual mitochondrial ETC complexes in aging AD and PD *Drosophila* was assessed. In control AD *Drosophila*, there were significant decreases in the activity of complexes 1, 2 and 3 (FIG. 4*r*; p<0.01). Treatment with LfS221 significantly elevated the activity of complex 3 at day 30 (p<0.05) while the probiotic formulation elevated the activity of all complexes (FIG. 4*r*; p<0.05). In control PD *Drosophila*, there were significant reductions in all of the mitochondrial ETC complexes 1 through 4. Both LfS221 and the probiotic formulation significantly elevated activity in mitochondrial complex 1, 2 and 4 while the probiotic formulation was more effective at increasing the activity of ETC complexes 2 and 3 (FIG. 4*s*; p<0.05).

Conclusion

Many of the canonical physiological changes in AD and PD including disease markers, metabolic changes, immunological stress, oxidative stress and mitochondrial complex activity were positively affected by administration of an exemplary probiotic treatment as provided herein, with the exemplary probiotic formulation providing more beneficial effects than a single probiotic alone.

Example 5: Exemplary Compositions Combined with Triphala (TFLA)

The following example demonstrates the efficacy of exemplary probiotic formulations combined with triphala (TFLA).

In alternative embodiments, a product of manufacture, composition, formulation, pharmaceutical composition or kit also comprises triphala (TFLA), which is a polyherbal formulation known in the traditional medical practice in India (Ayurveda) for its positive effects on digestive distress. Traditionally, TFLA is taken as a cold infusion, where the powdered formulation is mixed in cool water and consumed on an empty stomach in order to increase GI transit, relieve bloating and increase nutrient absorption. TFLA literally means 'three fruits' and the formulation is composed of equal amounts of *Emblica officinalis* (amalaki), *Terminalia chebula* (haritaki) and *Terminalia belerica* (bibhitaki). TFLA is an antioxidant-rich herbal formulation and rasayana (rejuvenator) with adaptogenic properties. Recently, the ethnomedicinal claims of TFLA have be confirmed by researchers and these activities include anti-oxidant, anti-inflammatory, serum cholesterol level maintenance, analgesic, wound healing, adaptogenic, hypoglycaemic and chemoprevenative effects. In addition, the traditional uses of TFLA as a gastrointestinal tonic including relief of GI tightness, constipation, diarrhea relief, symptoms of IBD and IBS, and an increase in GI motility all indicate that the TFLA could have prebiotic activity and that it conducts some of its beneficial effects through modifications of the gut microbiota.

Based on the broad physiological action of TFLA and its untapped potential as a prebiotic agent, TFLA-water extract was combined with an exemplary probiotic formulation as provided herein to create a novel synbiotic formulation (a product containing both probiotics and prebiotics). This exemplary formulation was tested, and it was determined that the addition of a prebiotic agent did not affect the activity of the probiotic formulation in vivo.

We tested if the addition of the plant formulation TFLA to an exemplary probiotic formulation as provided herein, to make a new synbiotic formula, has any effect on the efficacy of the probiotic formulation: the results demonstrated that this synbiotic formula either had no effect on the efficacy of the original exemplary probiotic formulation, or enhance its potency.

Methods

Triphala and Synbiotic Formulas

The dried components of Triphala (*Emblica officinalis, Terminalia bellirica* and *Terminalia chebula*) were obtained from the Ayurvedic Pharmacy at Banaras Hindu University in Varanasi, India. Each component was individually weighed and combined in equal parts (by weight) before being manually crushed and ground with a mortar and pestle into a fine powder. The resulting fine powder was used in all extractions. Extractions were performed by gently agitating 5 g of the Triphala powder in 100 mL of double distilled water for 72 h at room temperature. Following extraction, the solvent phase was filtered and evaporated with a roto-vap under vacuum pressure at 40° C. to complete dryness. The dry mass was recorded, reconstituted in 100 ml of double-distilled water and stored at 4° C. until further processing.

To make the TFLA and Synbiotic media for the *Drosophila*, the TFLA extract as described above was treated as a 10× formulation and incorporated in the cooled yet liquid media along with the probiotic formulation as described above. All physiological tests were performed as previously outlined in the above sections.

Results

The TFLA and synbiotic formulation were both tested with the same combination of metabolic, inflammation and oxidative stress tests along with testing in the AD and PD models of neurodegeneration. In the HSD metabolic model of diabetes, both TFLA and the synbiotic group reduced the total body weight by 30% and 22%, respectively (FIG. 5*ai*, p<0.01). Further, TFLA and the synbiotic formulation rescued both the circulating glucose levels (FIG. 4*aii*, p<0.05) and total glucose levels (FIG. 4*iii*; p<0.01) in the HSD treated *Drosophila*. Similar in the HFD metabolic model of obesity, there was a significant reduction in the weight gain in HFD-treated *Drosophila* treated with either TFLA (8.5%) or the synbiotic formulation (20%) (FIG. 5*bi*; p<0.01). Both the TFLA and synbiotic formulations also rescued the increase in total glucose in H1FD-treated *Drosophila* (FIG. 5*bii*, p<0.01) and the elevation in total triglycerides (FIG. 5*biii*; p<0.01). These results indicating that TFLA is very potent at reducing metabolic stress markers and combined with the probiotic formulation does not change its efficacy against metabolic challenge and can even increase its potency as the synbiotic formulation.

Markers of inflammation were also assessed in *Drosophila* pre-treated with either TFLA or the synbiotic formulation followed by an acute oral challenge with either 1.0×1010 CFU/ml of *E. coli* or *S. aureus*. In response to the *E. coli* stress, the almost 70% reduction in survivability in the control group was significantly increased by both the TFLA (25% reduction) and the synbiotic formulation (20% reduction) (Fig. Sci; p<0.01). There was also a significant increase in the zone of inhibition in the agar diffusion assay by both the TFLA and the synbiotic formulation, with the synbiotic formulation having a larger zone of inhibition compared to the TFLA alone group (Fig. Scii; p<0.01). Considering the expression of canonical inflammatory genes, Duox expression in the control group was significantly elevated by *E. coli* infection, an effect which was significantly reduced by both TFLA and the synbiotic formulation (Fig. ciii; p<0.01). Similar for IMD expression, the strong elevation of IMD in the control group was significantly reduced by the TFLA and synbiotic formulation (Fig. civ; p<0.01). Attacin A, a gram-negative sensitive AMP was also significantly reduced by both TFLA and the synbiotic formulation (FIG. 5*cv*; p<0.01). Finally, expression of the gram-negative sensitive AMP Diptercin, which was also extremely elevated in the control *E. coli* treated group, was significantly reduced by both the TFLA and synbiotic treatments (FIG. 5*c* vi; p<0.01). Overall, treatment with TFLA had a potent anti-inflammatory effect after oral infection with *E. coli*, which did not interfere with the action of the probiotic formulation in the synbiotic formulation and even accentuated its effect.

An acute oral infection with the gram-positive pathogen *S. aureus* was also conducted. In control *Drosophila*, there was a significant 70% loss in survivability after exposure to *S. aureus*, which was significantly reduced to 35% by TFLA treatment and 20% by the synbiotic formulation (data not shown; p<0.01). Similarly, both TFLA and the synbiotic formulation increased the clearance diameter by the agar diffusion test by 72% and 98%, respectively (data not shown, p<0.01). Regarding gene expression, there was a significant elevation of duox expression in the control *Drosophila* treated with *S. aureus*, which was significantly reduced by the synbiotic formulation (data not shown; p<0.01). IMD expression was moderately elevated by *S. aureus* expression and further elevated by TFLA and the synbiotic formulation (data not shown, p<0.01). Expression of the AMP Attacin A was elevated by 180% in the control *Drosophila*, which was significantly reduced by both the TFLA treatment (43% increase) and the synbiotic formulation (7% increase) (data not shown, p<0.01). Finally, the gram-positive response AMP Defensin was significantly elevated by the *S. aureus* treatment by almost 300%, which was completely rescued by both the TFLA and synbiotic formulation treatments (data not shown, p<0.01). Similar to the *E. coli* oral infection, *S. aureus* infection reared a potent immune response that was attenuated by TFLA and the synbiotic formulation treatment; similar to the probiotic formulation indicting that the prebiotic supplement does not affect the potency of the probiotic formulation.

Acute oxidative stress was introduced by exposing *Drosophila* to hydrogen peroxide after pre-treatment with either TFLA or the synbiotic formulation. Survivability of control *Drosophila* was greatly reduced by almost 70% after hydrogen peroxide exposure, which was significantly reduced to 30% reduction with TFLA treatment and 25% reduction in the synbiotic formulation group (data not shown; p<0.01). The elevated level of total oxidants in the control group was also significantly reduced by TFLA treatment and rescued by the synbiotic treatment (data not shown; p<0.01). Activity of superoxide dismutase was elevated in the control group exposed to the hydrogen peroxide stress, which was significantly reduced by TFLA pre-treatment and rescued by the synbiotic formulation pre-treatment (data not shown; p<0.01) indicating that the pre-treatment protected the *Drosophila* against having to mount a significant antioxidant response. Glutathione peroxidase was also significantly increased in the control group exposed to the hydrogen peroxide treatment, which was significantly reduced by only the synbiotic formulation (data not shown; p<0.01). Finally, the levels of lipid peroxidation were very significantly increased in the control by almost 300%, an increase that was completely rescued by both TFLA pre-treatment and the synbiotic formulation (data not shown; p<0.01). The reduction in total oxidants and reduction in the antioxidant enzyme induction indicates that similarly to the probiotic formulation, TFLA and together in the synbiotic, there is a higher innate anti-oxidant defense and that the combination of the probiotic formulation with TFLA does not impede the probiotic formulation's efficacy against oxidative stress.

The action of both TFLA and the synbiotic formulation was also tested in *Drosophila* afflicted with both AD and PD. In AD *Drosophila*, both TFLA and the synbiotic formulation increased the survivability of the aging flies with the synbiotic formulation being more effective than the TFLA (data not shown; p<0.01). Similarly, in the PD *Drosophila*, both TFLA and the synbiotic formulation significantly increased the Drosophilas' survivability with the synbiotic formulation being more effective than TFLA alone (data not shown; p<0.05). Measuring motility, aging AD *Drosophila* has a gradual loss of motility, most pronounced at day 30. Both the TFLA and synbiotic formulations significantly improved the AD *Drosophila*'s motility by 12% and 39%, respectively (data not shown, p<0.05). In the control PD *Drosophila*, the reduction in motility was gradually significant being at day 10 and continuously worsening. Both the TFLA and synbiotic formulation delayed motility impairment until day 20 and at both day 20 and day 30 significantly improve motility compared to the control (data not shown; p<0.01).

As expected, the level of Aβ in control flies with AD increased over time. Although with some variation, both the TFLA and synbiotic formulation reduced total Aβ accumulation at day 30, almost to the level of *Drosophila* at day 0 (data not shown; p<0.01). Similarly, with the activity of acetylcholinesterase, as predicted there was a decrease in ACh activity in control AD *Drosophila* over time, and this was significantly elevated by both the TFLA and the synbiotic formulation at day 30 (data not shown; p<0.01). Dopamine levels in control PD *Drosophila* was significantly reduced starting at day 10 and continuing to fall until day 30. Both the synbiotic formulation delayed the fall in dopamine levels until day 30 and both TFLA and the synbiotic formulation induced an increase in dopamine levels at day 30 compared to controls (data not shown; $p<0.05$).

Finally, to assess how both TFLA and the synbiotic formulation affects the mechanisms of the gut-brain axis in the context of AD and PD, the same physiological markers were assessed. In AD control *Drosophila*, there was a significant increase in the total glucose levels by 157%, which was significantly reduced by the synbiotic formulation (data not shown; $p<0.01$). Similarly, the 120% increase in total triglyceride levels in control AD *Drosophila* was significantly reduced by the synbiotic treatment (data not shown; $p<0.01$). In PD *Drosophila*, there was a significant 127% increase in total glucose levels, which were unchanged by either the TFLA or synbiotic formulation (data not shownix; $p>0.05$). However, in the PD *Drosophila*, the significant 187% increase in total triglycerides were significantly reduced by both the TFLA and symbiotic formulation to 143% and 119%, respectively (data not shown; $p<0.01$), with the synbiotic formulation being more effective than the TFLA treatment.

In the AD and PD *Drosophila* treated with either TFLA or the synbiotic formulation, the same combination of inflammatory markers was assessed in the aging flies. Duox expression in the PD *Drosophila* was significantly reduced by SO % at day 30 (data not shown; $p<0.01$) and treatment with the synbiotic formulation significantly elevated Duox expression. IMD was elevated in the aging PD *Drosophila*, though neither TFLA nor the synbiotic formulation had any significant effect on its expression. Relish was not significantly altered in the control group over time, although there was a significant decrease in its expression with the TFLA treatment. AMP expression was significantly elevated in the control aging PD *Drosophila*. The 180% increase in Attacin A was not affected by either TFLA or the synbiotic formulation (data not shown; $p>0.05$). The similar elevation of Defensin however was completely rescued by both the TFLA and synbiotic formulation ($p<0.01$). Finally, the almost 200% increase in Diptercin expression was unaffected by TFLA treatment though significantly reduced by the synbiotic formulation.

In PD *Drosophila*, Duox expression was reduced in the aging control flies, which was not affected by either TFLA or the synbiotic formulation (data not shown; $p>0.05$). IMD expression was reduced by about 20% in aging control flies, and significantly elevated by both TFLA and the synbiotic formulation (data not shown; $p<0.01$). Similar to the AD group, Relish expression was not significantly changed by either age or treatment. The AMP expression in PD *Drosophila* was elevated in the aging controls. The almost 200% elevated in Attacin A was significantly reduced by both TFLA and the synbiotic formulation treatment (data not shown; $p<0.01$). The similar elevation in Defensin expression was reduced only by the synbiotic formulation and not TFLA ($p<0.01$). Finally, the almost 300% elevation in Diptercin expression was significantly reduced by both TFLA and the synbiotic formulation ($p<0.01$). Overall, both TFLA and the synbiotic formulation had positive effects on the immune parameters affected in both AD and PD *Drosophila* disease models and the combination of TFLA with the probiotic formulation did not have a negative impact on its efficacy and even increased its potency in some instances.

Considering the oxidative stress markers, there was a 30% increase in total oxidants in the aging AD model in the control flies. This elevation was significantly reduced by both the TFLA and the synbiotic formulation with the synbiotic formulation being more effective than the TFLA treatment alone (data not shown; $p<0.01$). Superoxide dismutase activity was relatively unchanged in the aging control *Drosophila* and there was no effect by either the TFLA or synbiotic formulation treatment. Activity of glutathione peroxidase was elevated by almost 10% in the aging control AD *Drosophila*, and significantly reduced by TFLA treatment (data not shown; $p<0.01$). Finally, the level of lipid peroxidation was elevated by 38% in the aging control AD *Drosophila*, which was significantly reduced by both the TFLA and the synbiotic formulation, with the synbiotic formulation being slightly more effective than the TFLA formulation at reducing the LPO levels (data not shown; $p<0.010$. In the aging PD *Drosophila*, the 24% increase in total oxidants in the control *Drosophila* was reduced only by the synbiotic formulation (data not shown; $p<0.01$). Similar to the AD *Drosophila*, there was no significant differences in SOD activity in the aging control flies and little effect by either TFLA or synbiotic formulation treatment. GPx activity was slightly reduced in the control aging PD *Drosophila*, which was significantly elevated by both TFLA and synbiotic formulation treatment, with the TFLA treatment increasing the GPx activity significantly higher than the synbiotic formulation (data not shown; $p<0.01$). Finally, the 37% increase in lipid peroxidation in aging control PD *Drosophila* was significantly reduced only by the synbiotic formulation, which in fact completely reduced the LPO levels to the level of young controls (data not shown; $p<0.01$). The TFLA prebiotic had significant impacts on several markers of oxidative stress, and the combination with the probiotic formulation did not affect the efficacy of the formulation's action, and even accentuated in some parameters.

Mitochondrial ETC complex activity in AD and PD was also affected by the TFLA and synbiotic formulation treatment. In aging AD control *Drosophila*, the activity of ETC complex 1 was reduced by 57% after 30 days, while synbiotic treatment, but not TFLA, significantly elevated complex 1 activity (data not shown; $p<0.05$). ETC complex 2 activity was also reduced in the aging AD flies, unaffected by TFLA treatment and completely rescued by the synbiotic formulation at day 30 (data not shown; $p<0.01$). ETC complex 3 activity was reduced by almost SO % in aging AD control *Drosophila*, which was equally elevated by both TFLA and the synbiotic formulation (data not shown; $p<0.01$). Finally, ETC complex 4 in AD *Drosophila* was not affected over time or by the treatment with either TFLA or the synbiotic formulation (data not shown; $p>0.05$). In aging PD *Drosophila*, there was a significant reduction in ETC complex 1 activity by 70%, a reduction which was significantly increased by treatment with both TFLA and the synbiotic formulation (data not shown; $p<0.01$). ETC complex 2 activity was reduced by over SO % in control PD *Drosophila* and further elevated by both TFLA and the synbiotic formulation (data not shown; $p<0.01$). There was a very strong 80% reduction of ETC complex 3 activity in aging PD *Drosophila*, which was only elevated by the synbiotic formulation (data not shown; $p<0.05$). Finally, the almost 60% reduction in ETC complex 4 activity in aging PD *Drosophila* was only elevated by the synbiotic formulation (data not shown; $p<0.05$). Overall, the reduction in ETC complex activity in both the AD and PD *Drosophila* models was elevated by treatment with TFLA and the combination of TFLA with the probiotic formulation to make the synbiotic formulation had either no effect on the formulation's efficacy or increased its potency.

Conclusions

Overall combination of the prebiotic plant product TFLA with the probiotic formulation did not have any effect on the efficacy of the exemplary synbiotic formulation and even elevated its potency in some instances.

Example 6: Exemplary Methods for Enhancing Longevity: Longevity Extension in *Drosophila melanogaster* Through Gut-Brain-Axis Communication The following example describes data that demonstrates the efficacy of exemplary compositions and methods as provided herein to enhance (increase) longevity and ameliorate aging.

In this study, novel probiotic and synbiotic formulations are shown to combinatorially extend longevity in *Drosophila melanogaster* through mechanisms of gut-brain-axis communication with implications in chronic disease management. Both the probiotic and synbiotic formulations rescued markers of metabolic stress by managing insulin resistance and energy regulatory pathways. Aging and chronic disease development are multifactorial processes involving the cumulative effects of metabolic distress, inflammation, oxidative stress and mitochondrial dynamics, and variations in the gut microbiota are associated with age-related phenotypes.

Both formulations also ameliorated elevations in inflammation, oxidative stress and the loss of mitochondrial complex integrity. In almost all the measured pathways, the synbiotic formulation has a more robust impact than its individual components insinuating its combinatorial effect. The concomitant action of the gut microbiota on each of the key risk factors of aging and makes it a powerful therapeutic tool against neurodegeneration, diabetes, obesity, cardiovascular disease and other age-related chronic diseases.

This study describes how a novel probiotic and synbiotic formulation impacts *Drosophila melanogaster* longevity through mechanisms of the GBA. The present probiotic and synbiotic formulations showed combinatorial action on reducing markers of physiological stress, oxidative stress, inflammation and mitochondrial ETC complex integrity therefore targeting most of the main aging mechanisms. This action benefits not only longevity but would prevent many age-related chronic diseases that are associated with the aforementioned states.

Results

The Probiotic and Synbiotic Formulation has Beneficial Effects on Physiological Metabolic Markers in Aging *Drosophila melanogaster*

The physiological metabolic parameters of *Drosophila* were determined every ten days for thirty days in aging *Drosophila* exposed to either probiotic, prebiotic, the probiotic or synbiotic formulation beginning at the first day after eclosion. As expected, the total weight of *Drosophila* in the untreated controls showed a time-dependent elevation (FIG. 6a; F (3,18)=3.24; p<0.05). This trend was observed in all the groups; however, by day 30, the probiotic and synbiotic formulation invoked a significant reduction in total weight compared to controls, the individual probiotics and TFLA-treated group (FIG. 6a). Similarly for the total glucose measurement in aging *Drosophila*, there was a time-dependent increase in total glucose in control *Drosophila* peaking with a 2.5-fold increase by day 30 (FIG. 6b; F (3,18)=4.13, p<0.05). Each of the individual probiotics and TFLA prebiotic showed similar time-dependent increase in total glucose levels however at day 30, there was a reduction in total glucose in all groups. Notably, both the probiotic and synbiotic formulation completely rescued the elevation in total glucose by day 30, which was significantly lower than Lp8826, Bi702255 and the TFLA-treated groups (p<0.01). Finally, variation in total triglyceride levels (F (3,18)=5.34, p<0.05) were elevated by 1.7-fold in untreated controls by day 30 (FIG. 6c, p<0.01). By day 30, there were reductions in total triglyceride levels in the Lf5221, Bi702255, probiotic and synbiotic formulation groups, with Lf5221 and the probiotic formulation completely reducing the total triglyceride levels to the level of day 0 flies. Overall, the probiotic formulation was the most effective at reducing all the physiological markers of metabolic stress in *Drosophila*, while the synbiotic formulation showed almost as effective results.

Figure 7A:
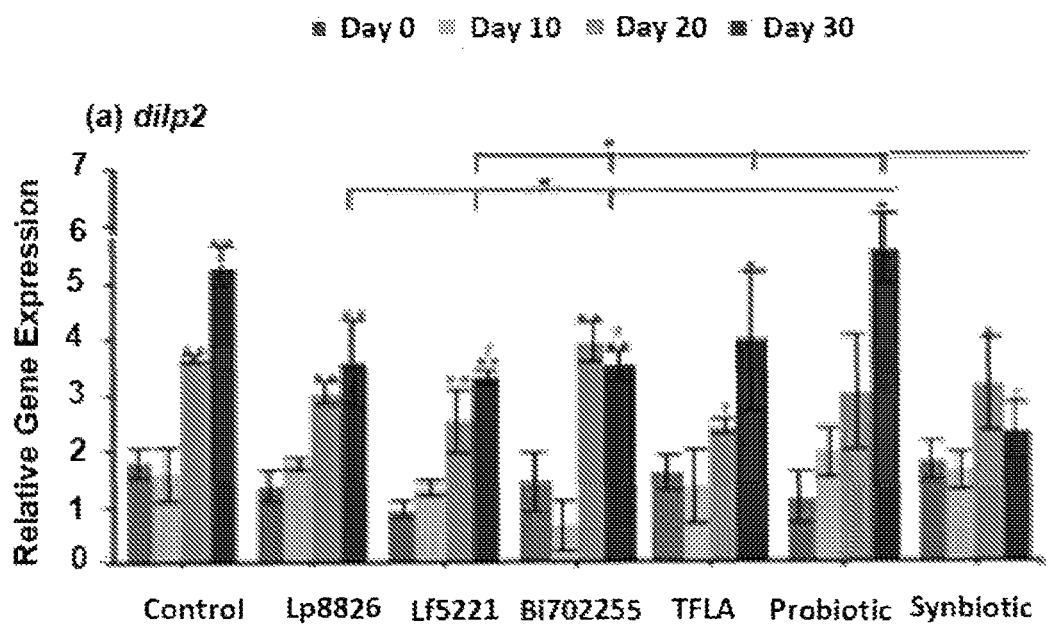
Figure 7B:
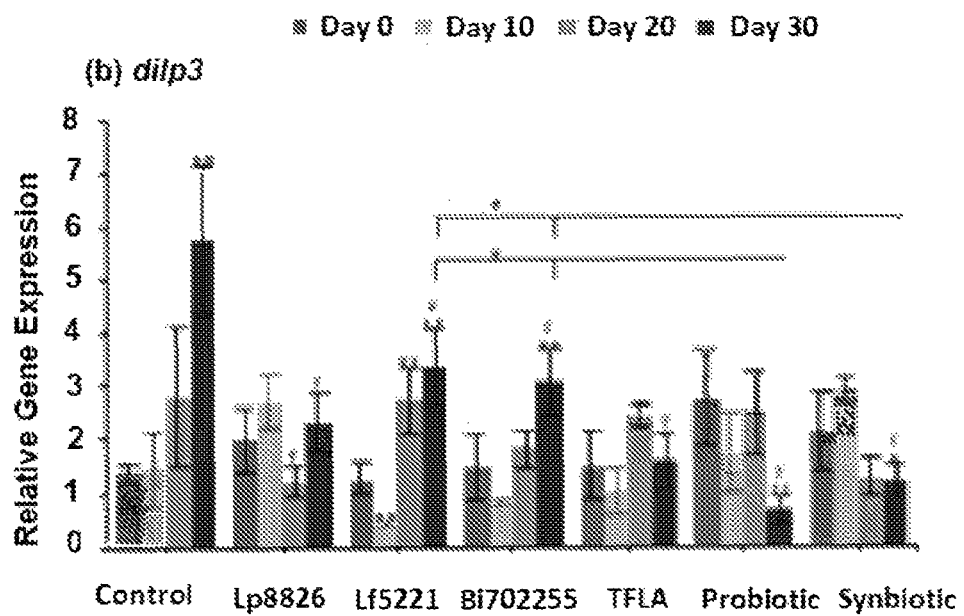
Figure 7C:
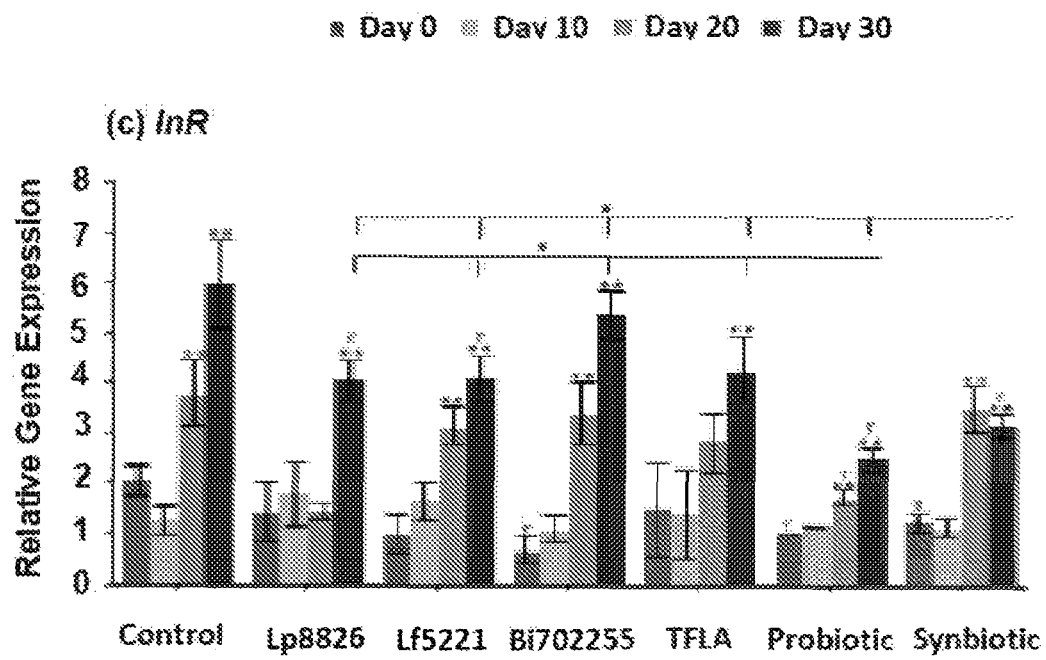

Insulin-Like Signaling in Aging *Drosophila melanogaster* is Positively Affected by Probiotic and/or Prebiotic Treatment To assess the underlying genetic regulatory mechanisms of metabolism affected by the prebiotic or probiotic supplementation, the expression of a battery of insulin signaling genes was assessed using real-time PCR. *Drosophila* insulin-like peptide (dilp)2 expression (F (3,18)=3.47, p<0.05) was elevated at days 20 and 30 in control flies (FIG. 7a; p<0.01). At day 20, only TFLA supplementation lowered dilp1 expression while at day 30, Bi702255 and synbiotic formulation reduced dilp2 expression by 33% and 57%, respectively (p<0.01). Notably, only synbiotic formulation was able to rescue dilp1 expression, which was significantly lower than any of the other treatment groups. Similarly, dilp3 expression (F (3,18)=4.87, p<0.05) was elevated at day 30 in the control group (FIG. 7b; p<0.01), which was significantly reduced by all groups. Supplementation with Lp8826 and TFLA rescued dilp3 expression to the level of day 0 controls while the probiotic and synbiotic formulation reduced dilpi expression further; a decrease that was significantly lower than Lf5221 and Bi702255 at day 30. The insulin receptor (InR) (F (3,18=4.53, p<0.05) was likewise elevated at days 20 and 30 in control *Drosophila* (FIG. 7c; p<0.01). At day 20, only the probiotic formulation significantly reduced InR expression while at day 30, Lp8826, Lf5221, the probiotic and synbiotic formulation elicited significant reductions (p<0.01). Notably, the probiotic formulation reduced InR level at day 30 to a greater extent than all the other groups while the synbiotic formulation was lower than all groups spare the probiotic formulation.

Figure 7D:
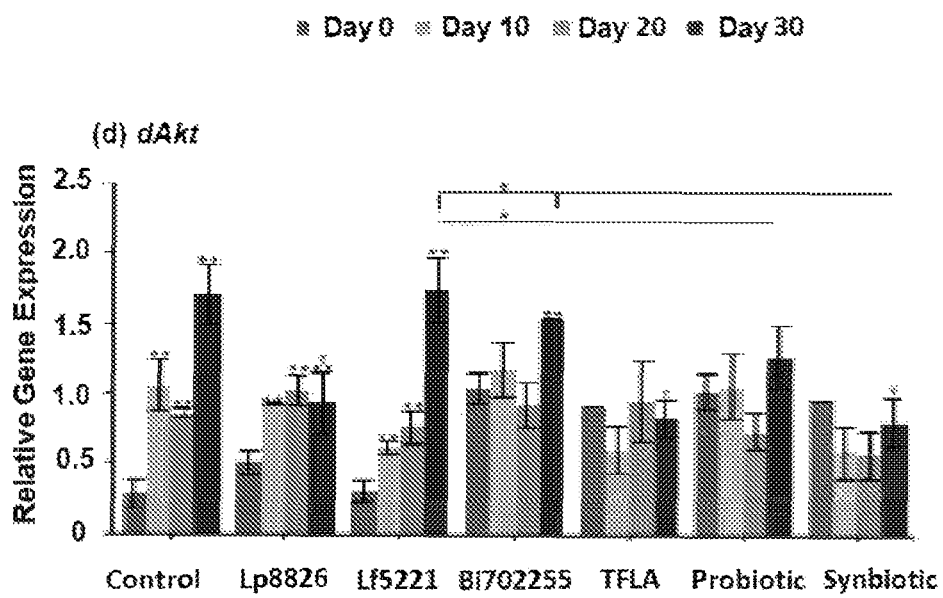
Figure 7E:
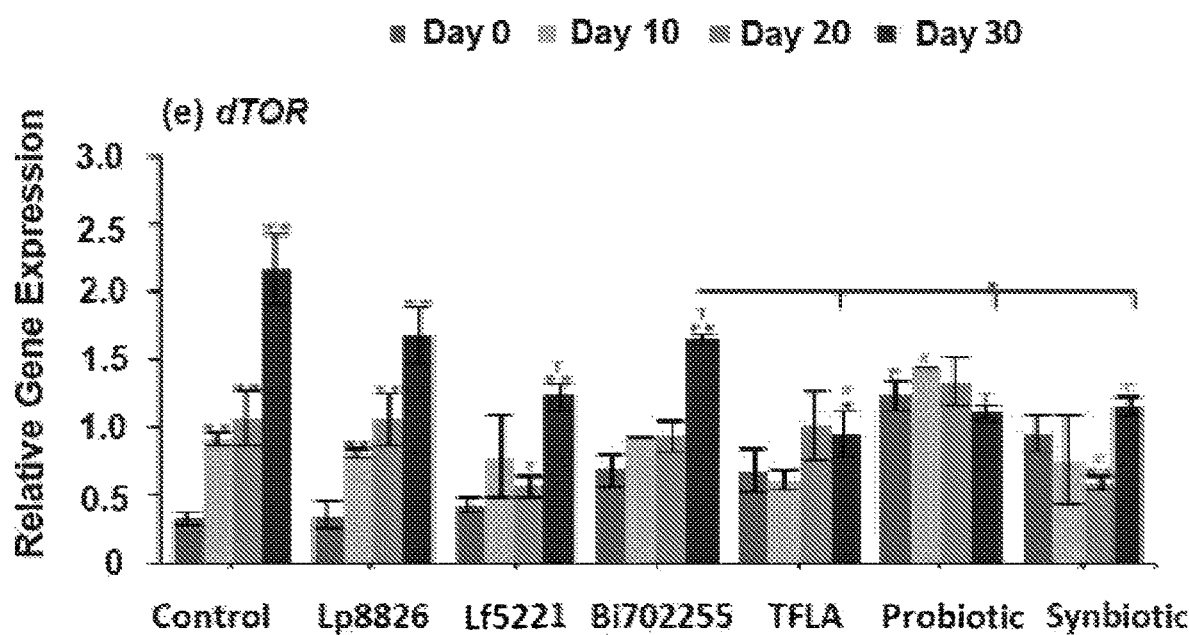

Examining the insulin signaling pathways downstream of the insulin receptor, similar yet intriguing results were obtained. dAkt expression (F (3,18)=4.82, p<0.05) was elevated in the aging control *Drosophila* from day 10 to day 30 (FIG. 7d; p<0.01). At day 30, supplementation with Lp8826, TFLA and the synbiotic formulation significantly reduced dAkt expression (p<0.05). Notably, TFLA, the probiotic and synbiotic formulations completely rescued dAkt levels at day 30 with the synbiotic formulation reducing dAkt expression greater than LfS221 and Bi702255. Directly downstream of dAkt is dTOR (F (3,18)=4.91, p<0.01), whose expression was likewise elevated from day 10 to 30 in control *Drosophila* (FIG. 7e; p<0.01). Only Lp8826 did not reduce dTOR levels at day 30 while TFLA, the probiotic and synbiotic formulation completely rescued expression. Finally, dFOXO, a transcription factor downregulated by dAkt (F (3,18)=4.12, p<0.01), was downregulated in control aging *Drosophila* from day 10 to day 30

Figure 7F:
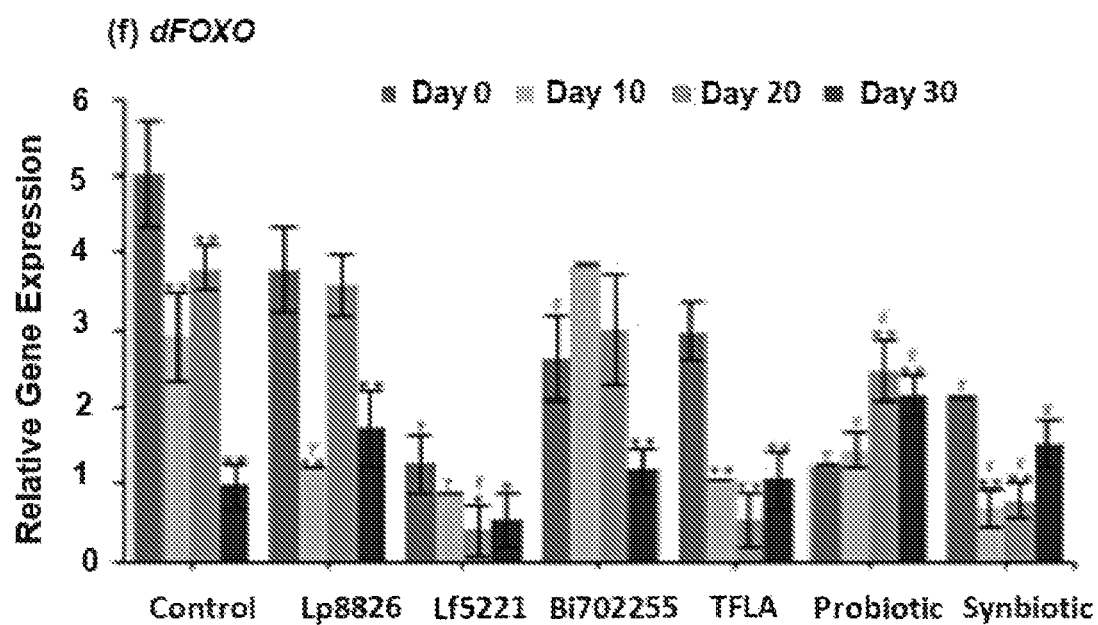

(FIG. 7f, p<0.01). Only the probiotic and synbiotic formulations were able to elevate dFOXO expression levels and only the synbiotic formulation completely rescued its expression to the level of day 0 controls. Overall, the individual probiotics and TFLA had differential yet positive impacts on the insulin-signaling pathways in aging *Drosophila*', however, the probiotic and synbiotic formulations demonstrated combinatorial effects on rescuing the underlying insulin signaling dysregulation in aging *Drosophila*.

Fatty Acid Metabolism is Benefited from Supplementation of the Probiotic and Synbiotic Formulation in Aging *Drosophila melanogaster*

Figure 8A:
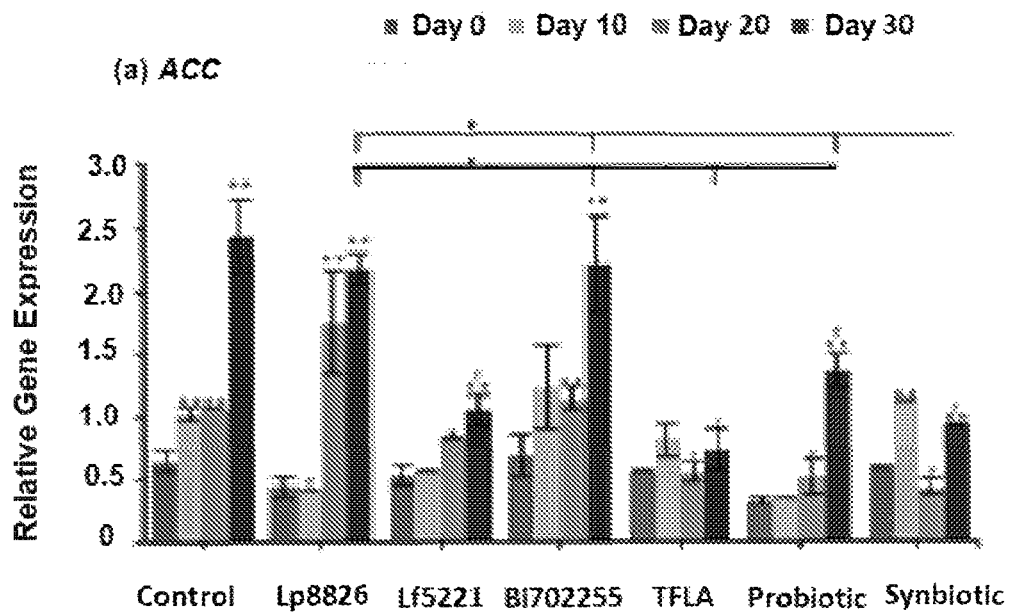
Figure 8B:
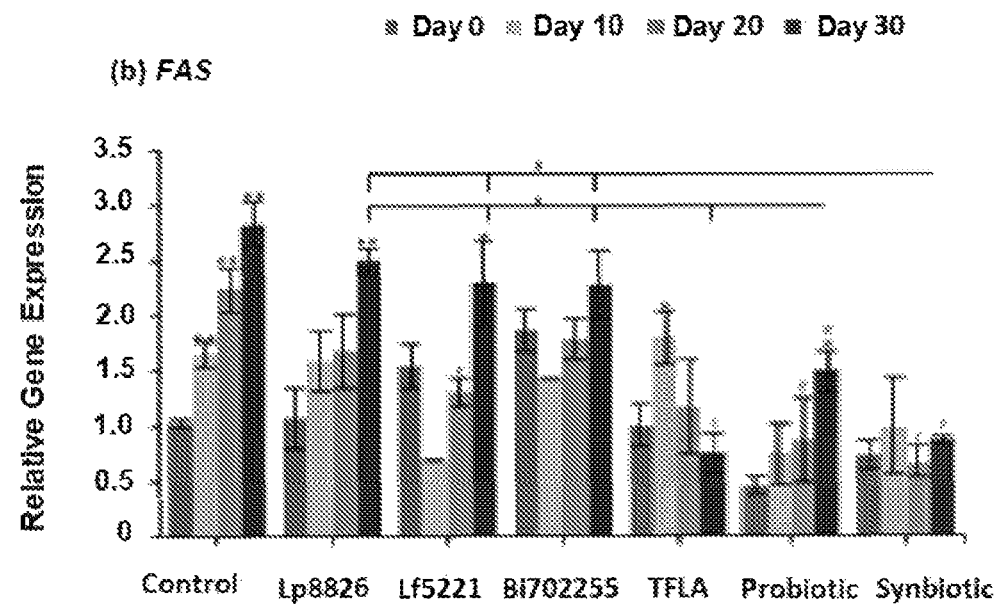
Figure 8C:
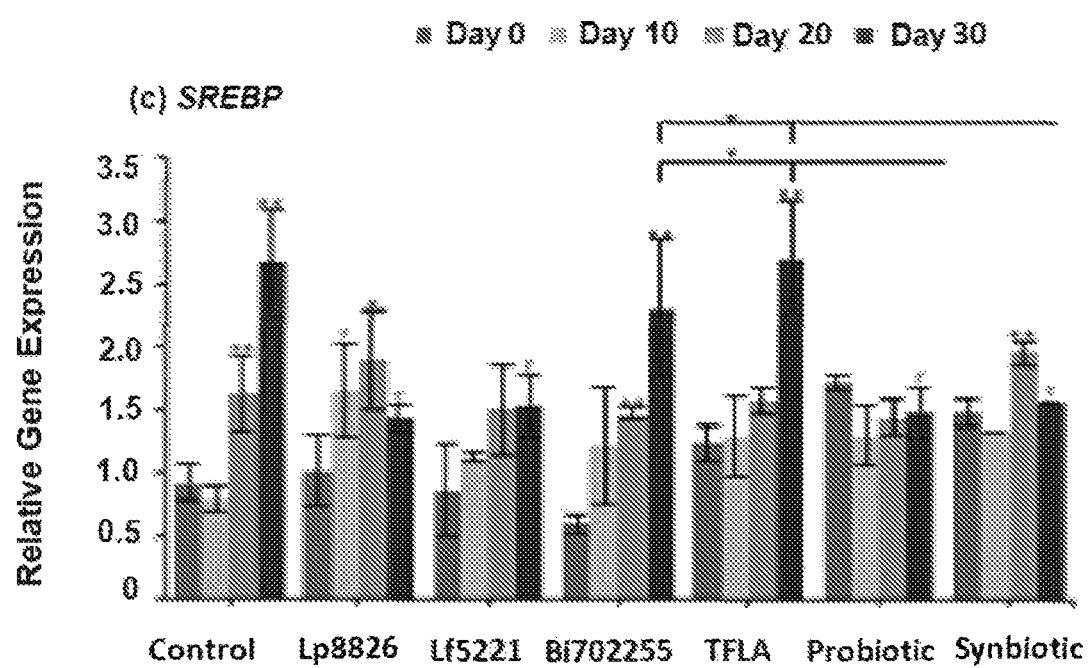
Figure 8D:
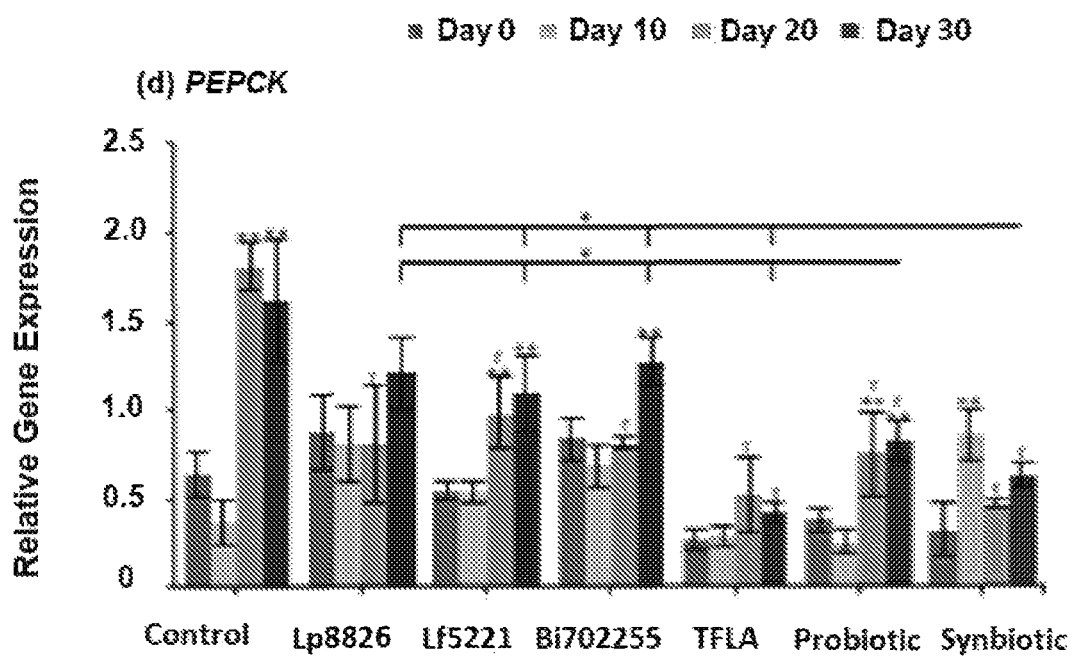
Figure 8E:
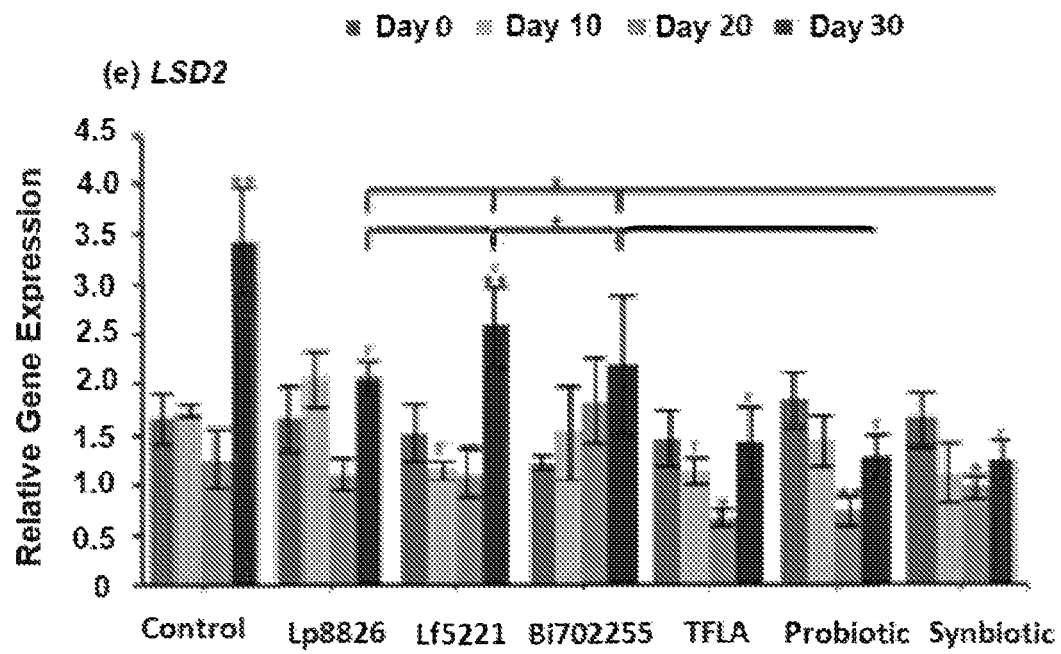
Figure 8F:
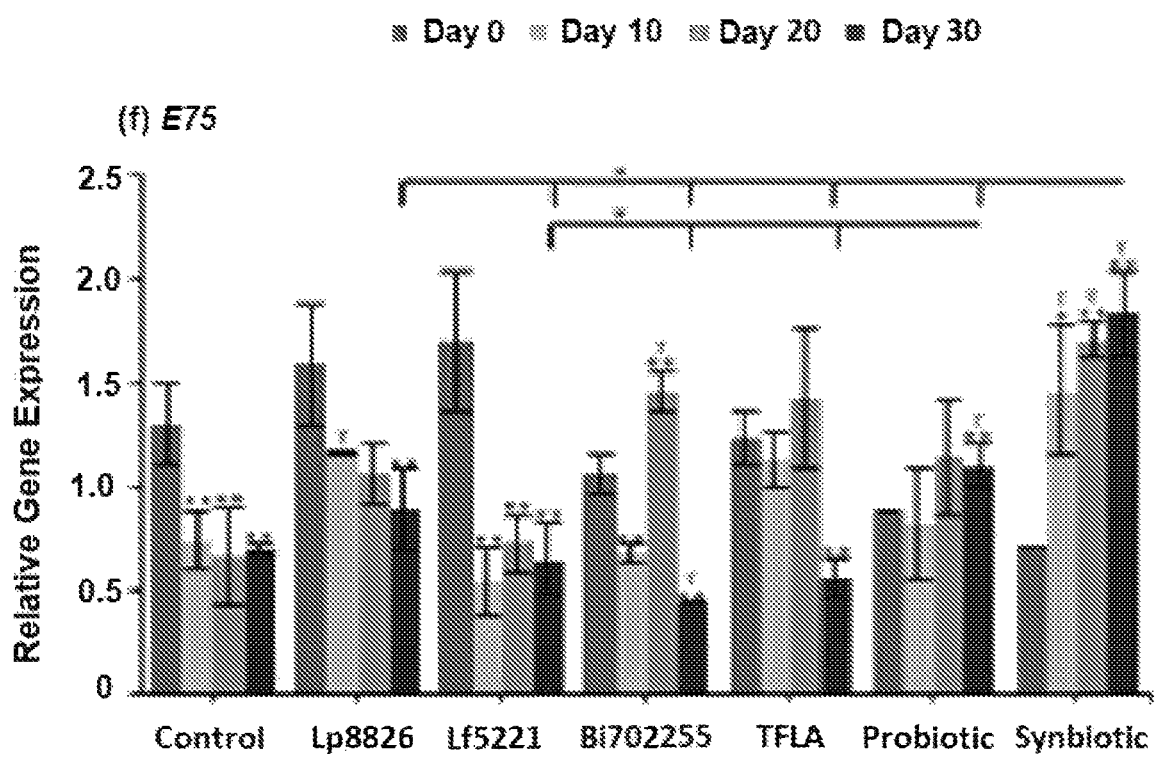

To determine the mechanism through which the total triglycerides were elevated in aging *Drosophila* and how the probiotics alleviated this effect, the expression of several lipogenesis and adipogenesis regulatory factors was assessed. Acetyl-CoA carboxylase (ACC) and fatty acid synthase (FAS) are both lipogenic factors activated by the transcription factor sterol regulatory element binding protein (SREBP). Expression of both ACC (F (3,18)=4.12, p<0.05) (FIG. 8a) and FAS (F (3,18)=3.91, p<0.05) (FIG. 3b) were significantly elevated from day 10 to day 30 (p<0.01) indicating an elevation in lipogenesis in aging control *Drosophila*. At day 30, ACC expression was reduced by Lf5221, TFLA, the probiotic and synbiotic formulation with the synbiotic formulation having a greater effect than the probiotic formulation (p<0.05). FAS expression was only reduced by TFLA, the probiotic and synbiotic formulations at day 30 where TFLA and the synbiotic formulations rescued FAS expression to the level of day 0 controls. SREBP expression (F (3, 18)=3.2, p<0.05) followed the same trend (FIG. 8c). The elevation at days 20 and 30 (p<0.01) was reduced by Lp826 and Lf5221 and rescued by the probiotic and synbiotic formulations at day 30 (p<0.01). Phosphoenolpyruvate carboxykinase (PEPCK) is a major regulator of gluconeogenesis and like the lipogenesis genes (F (3,18)=4.63, p<0.05), increased in expression at days 20 and 30 in control *Drosophila* (FIG. 8d; p<0.01). At day 30, PEPCK expression was reduced by TFLA, the probiotic and synbiotic formulations with TFLA and the synbiotic formulation rescuing PEPCK expression to the level of day 0 controls (p<0.01). Lipid storage droplet (LSD) 2 is expressed in the fat body and controls triglyceride accumulation. LSD2 expression (F (3, 18)=3.28, p<0.05) was elevated at day 30 in control *Drosophila* (FIG. 8e; p<0.01) and rescued by Lp8826, TFLA, the probiotic and synbiotic formulations (p<0.01). Finally, E75 a transcriptional target of the *Drosophila* PPARγ homolog responsible for adipogenesis and insulin sensitivity. E75 expression (F (3,18) =5.09, p<0.05) was significantly reduced at days 10 through 30 in aging controls (p<0.01), an effect that was reduced by Bi702255 at day 30 and elevated only by the probiotic and synbiotic formulation at day 30 with the synbiotic formulation having a greater impact than the probiotic formulation (p<0.05).

Inflammatory Markers Elevated with Age are Reduced by Combinatorial Prebiotic and Probiotic Treatment The agar diffusion test measures the amount of secretable immunogenic factors and their immunogenicity against a pathogenic lawn on a nutrient agar plate. Against *E. coli*, control *Drosophila* experienced a large reduction in immunogenicity (F (3, 18)=3.98, p<0.05) as the clearance diameter was reduced by 47% from day 0 to day 30 (FIG. 9a; p<0.01). At day 20, TFLA, the probiotic and synbiotic formulations improved the clearance diameter (p<0.01) while at day 30, all the supplementation groups had a positive effect. At day 20 and 30, the synbiotic formulation was the most effective at improving the clearance diameter supporting its combinatorial effect. A similar trend was noted for the clearance diameter on a *S. aureus* plates (F (3, 18)=4.12, p<0.05) where control *Drosophila* demonstrated a 56% decrease in clearance diameter from day 0 to day 30 (FIG. 9b; p<0.01). All supplementation groups elicited a positive effect at days 20 and 30; however, both the probiotic and synbiotic formulations had a greater effect than the individual probiotics or TFLA alone.

Figure 9C:
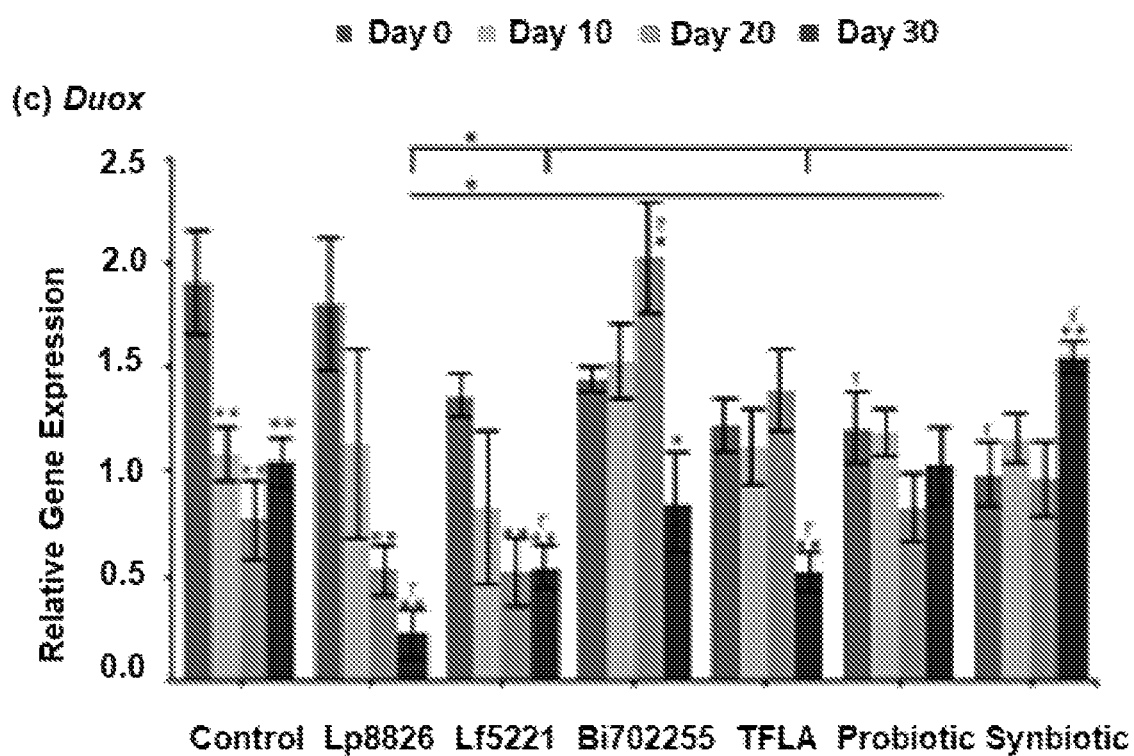
Figure 9D:
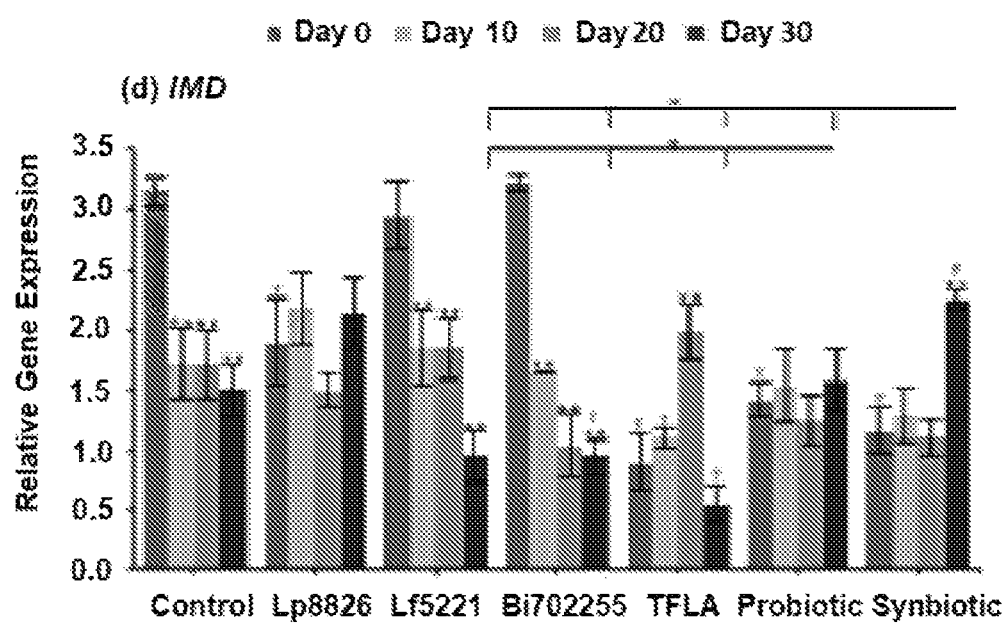
Figure 9E:
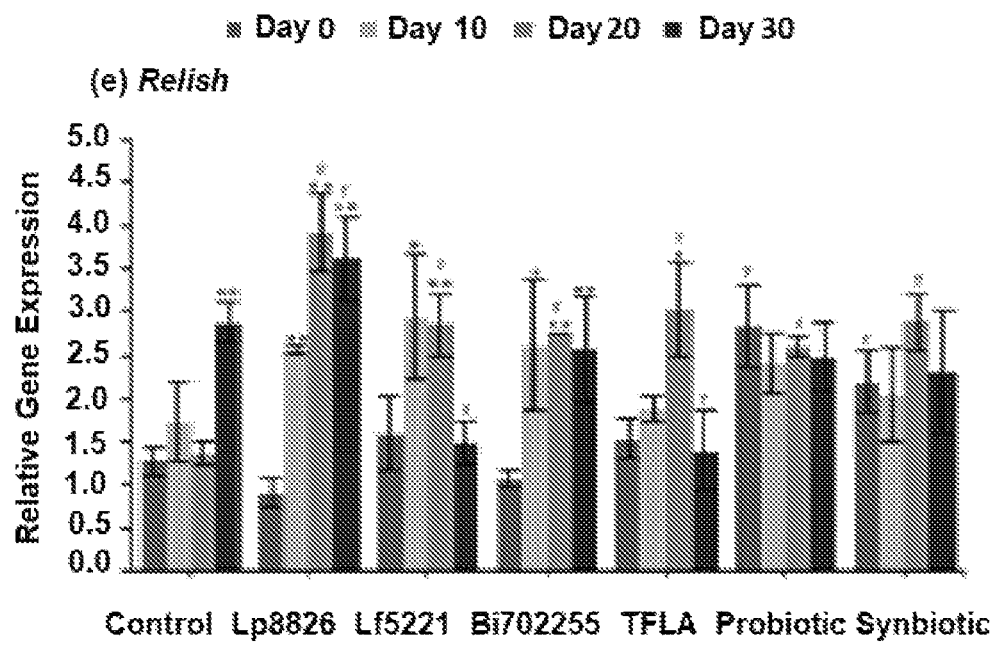

Concerning regulation of the immunological genetic markers, expression of dual oxidase (Duox), the primary innate immune response that stimulates ROS release following a pathogenic insult (F (3,18)=3.78, p<0.05), was reduced at days 10 through 30 in the untreated *Drosophila* (FIG. 9c; p<0.01). At day 30, Duox expression was rescued by the probiotic and synbiotic treatment compared to the day 0 control, but only the synbiotic formulation at day 30 improved Duox expression compared to the untreated control. Immune deficiency (IMD) is another innate immune responder though is slightly more sensitive to gram negative bacteria. IMD expression (F (3, 18)=4.71, p<0.05) was reduced in control *Drosophila* at days 10 through 30 (FIG. 9d; p<0.01) and at day 30, was only elevated by the synbiotic formulation. Nevertheless, due to variations in baseline expression, Lp8826, TFLA the probiotic and synbiotic formulation all effectively rescued ID expression at day 30 (p>0.05). Relish is a cytokine-like factor downstream of IMD pathway (F (3,18)=2.54, p>0.05) whose expression was upregulated at day 30 in control *Drosophila* (FIG. 4e; p<0.01). The impact of the probiotic bacteria was limited and varied though both the probiotic and synbiotic formulations eliminated any variation in Relish expression in the aging *Drosophila*.

Figure 9F:
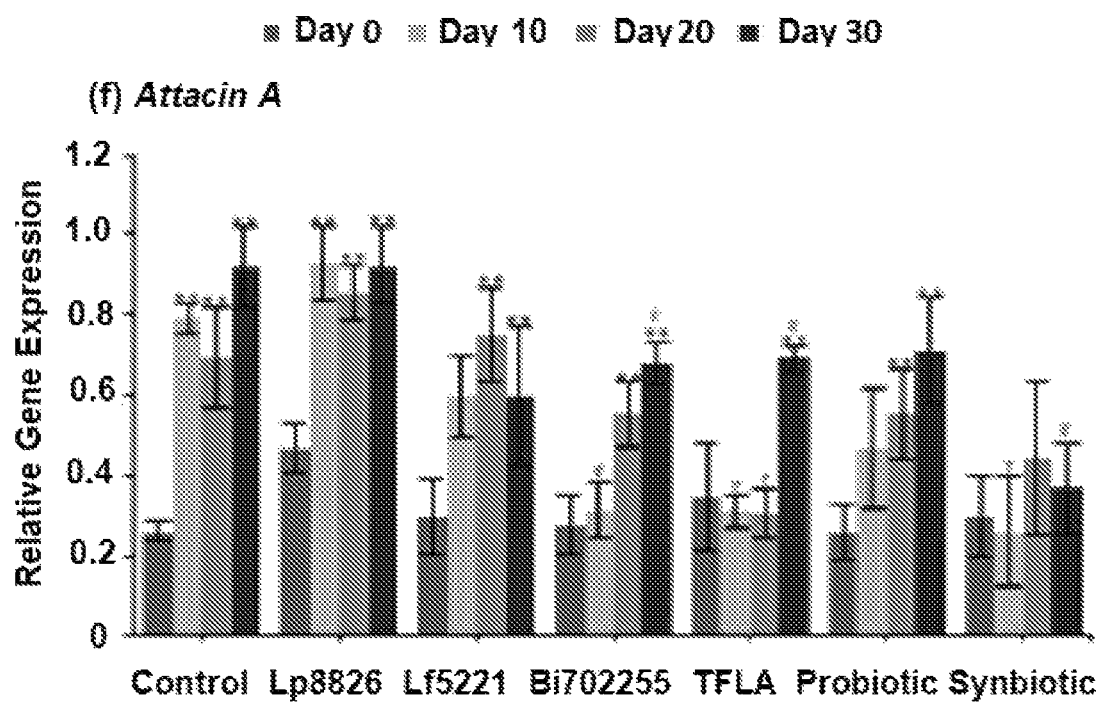
Figure 9G:
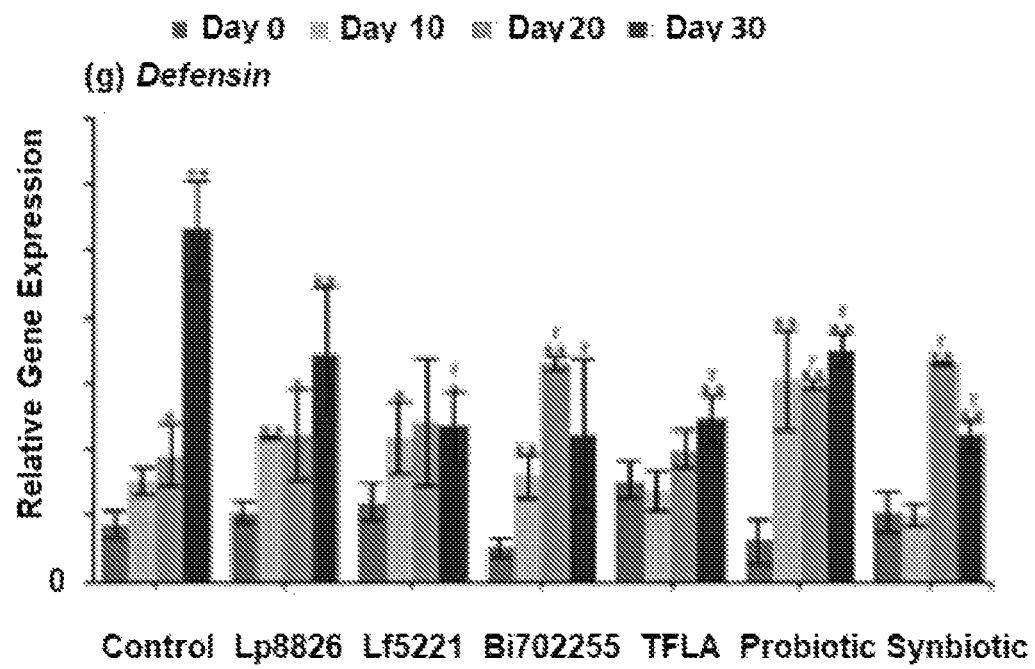
Figure 9H:
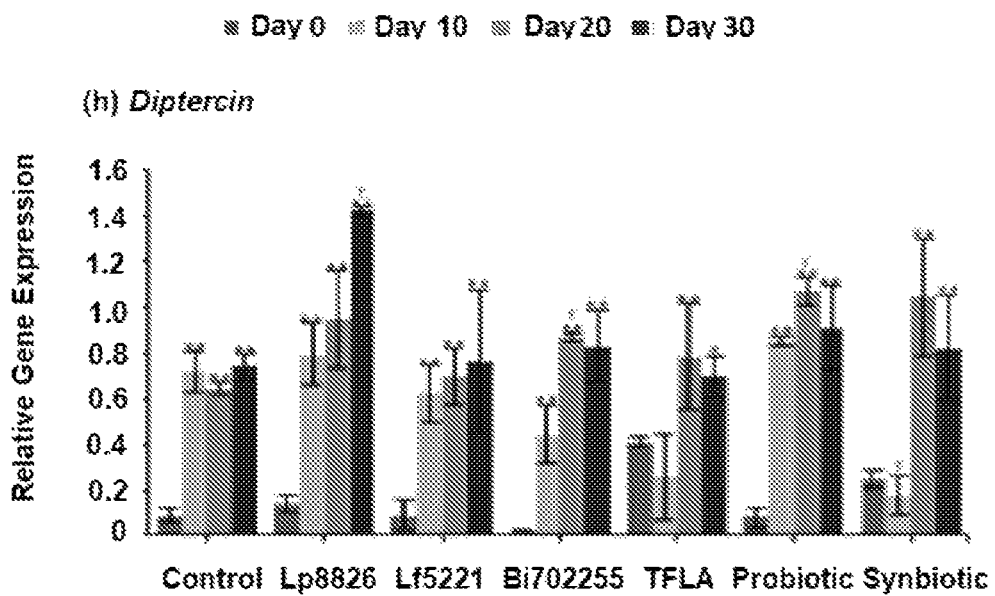

The antimicrobial peptides (AMPs) are the effector molecules of the innate immune system induced downstream of the IMD and Toll-pathways. Attacin A transcription is activated both by gram-positive and gram-negative bacterial insults (F (3,18)=3.73, p<0.05) and in the present model, increased dramatically in aging control *Drosophila* in days 10 through 30. (FIG. 9f; p<0.01). At day 30, Attacin A expression was reduced by Bi702255, TFLA and the synbiotic formulation with the latter rescuing expression to the level of day 0 controls (p<0.01). Defensin is activated downstream of the toll-pathway and gram-positive bacterial insults. Like Attacin A, Defensin expression (F (3, 18)=4.13, p<0.05) was elevated in aging control *Drosophila* (FIG. 9g; p<0.01) and reduced at day 30 by all supplementation groups except Lp8826. Finally Diptercin, activated downstream of IMD from a gram-negative challenge (F (3, 18)=2.31, p>0.05), was also elevated in aging control *Drosophila* on days 10 through 30 (FIG. 9h; p<0.01), though there was little impact of any probiotic and/or prebiotic treatment.

Figure 10A:
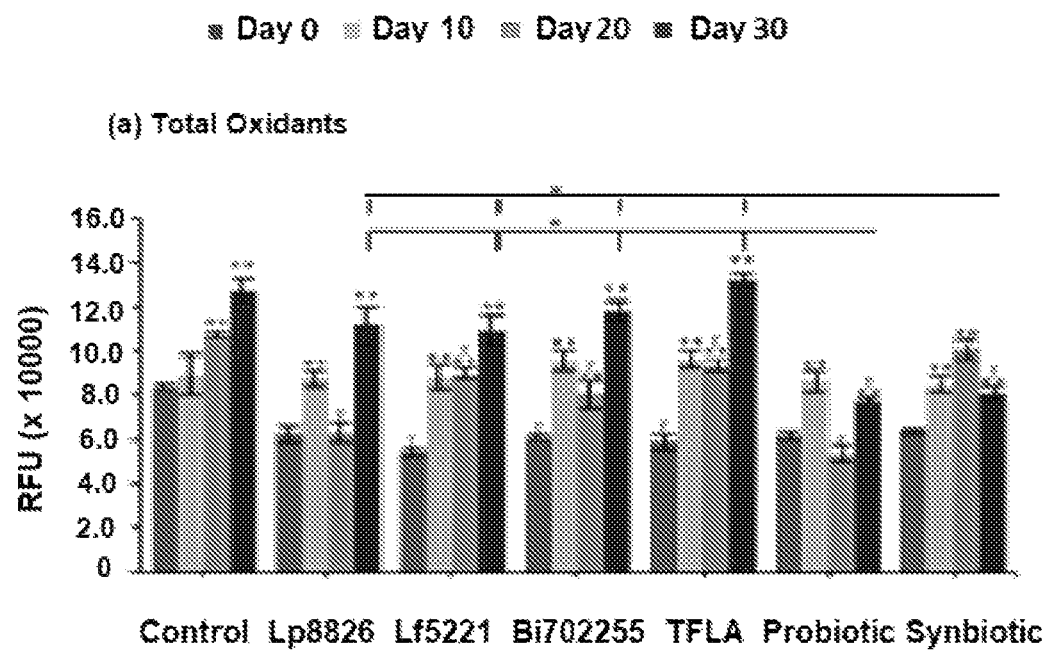
Figure 10B:
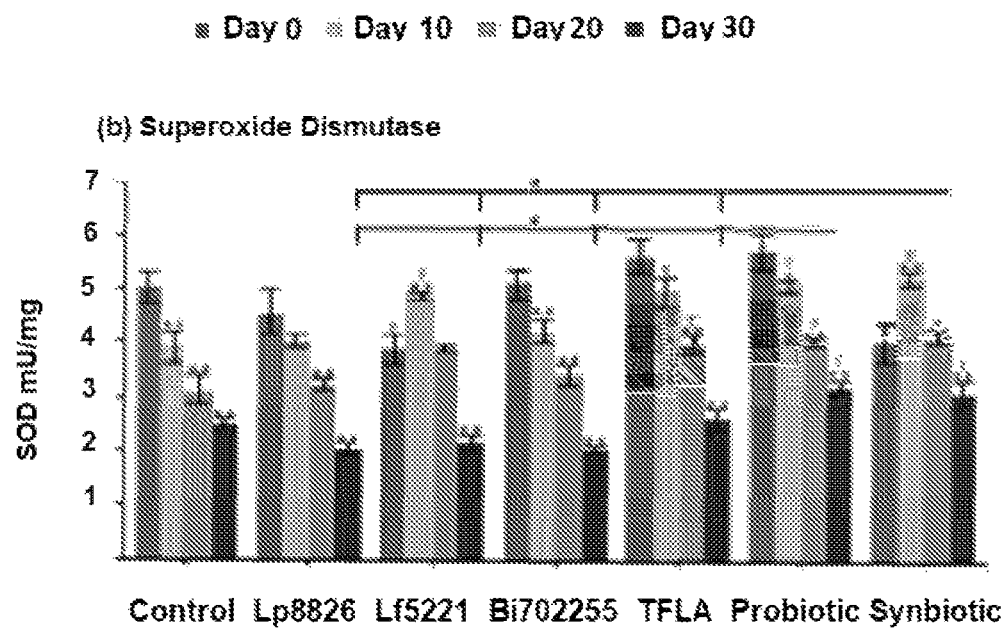
Figure 10C:
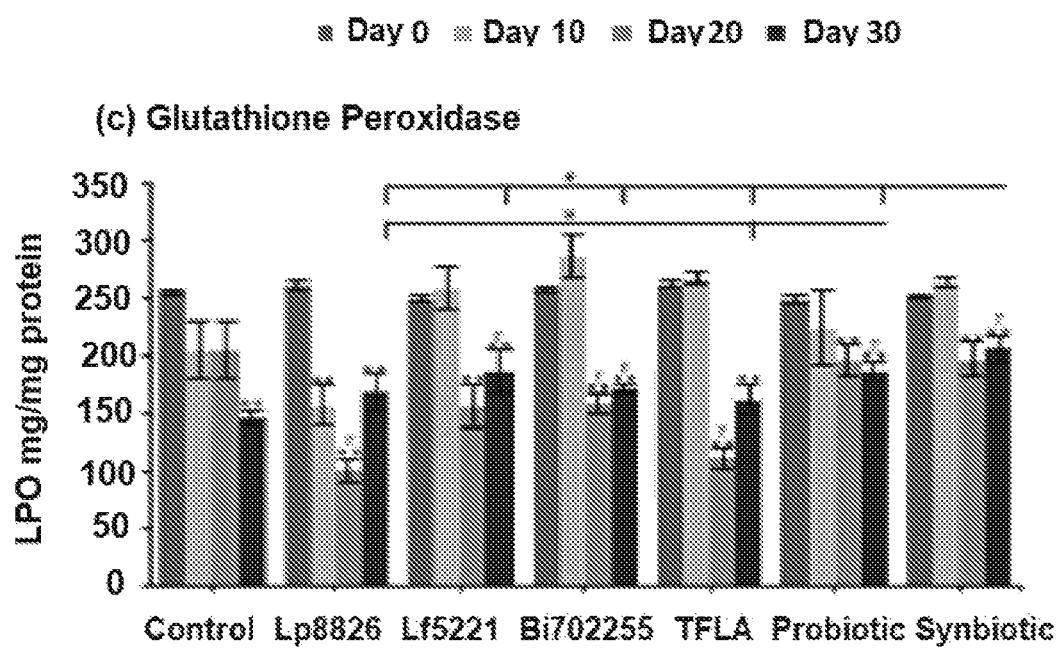
Figure 10D:
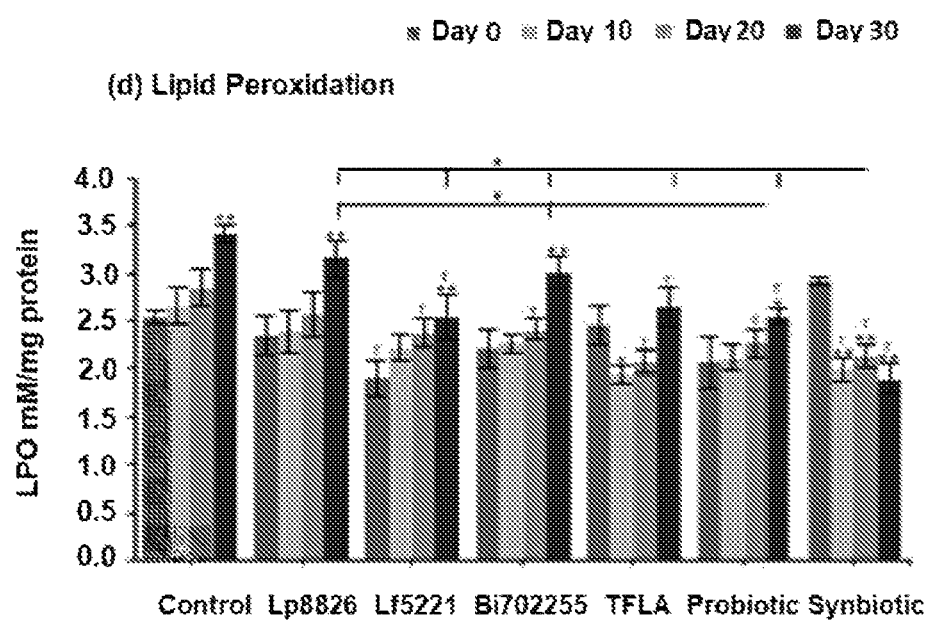
Figure 10E:
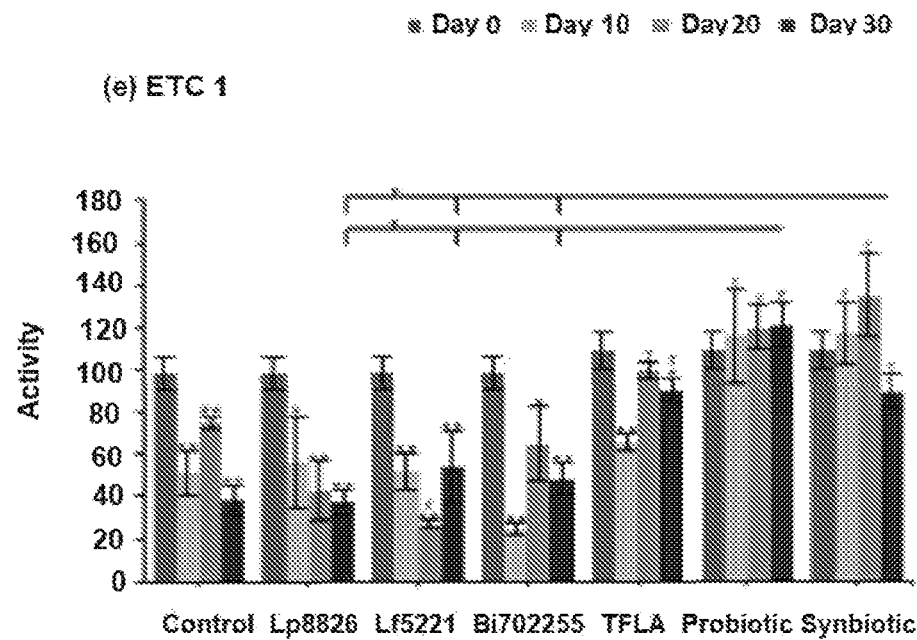
Figure 10F:
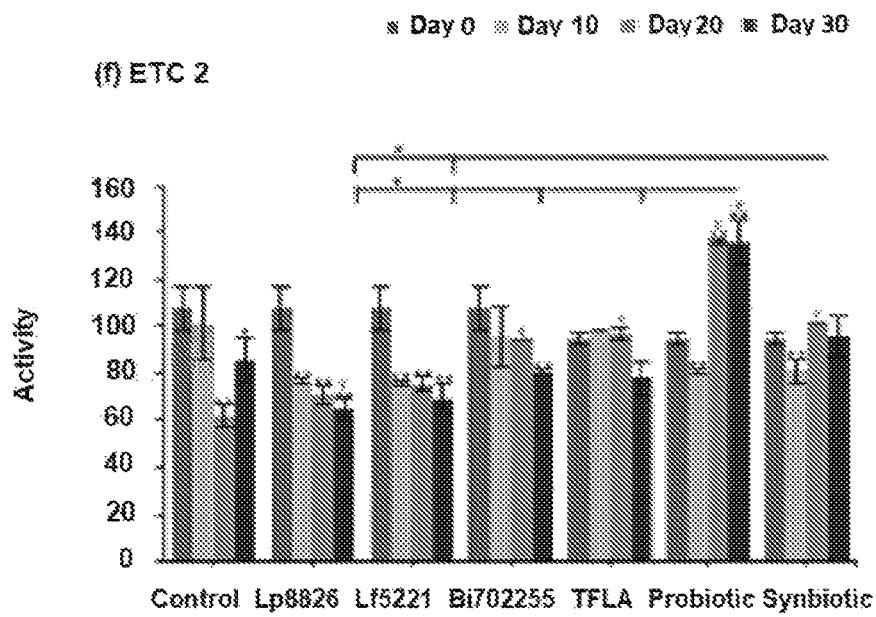
Figure 10G:
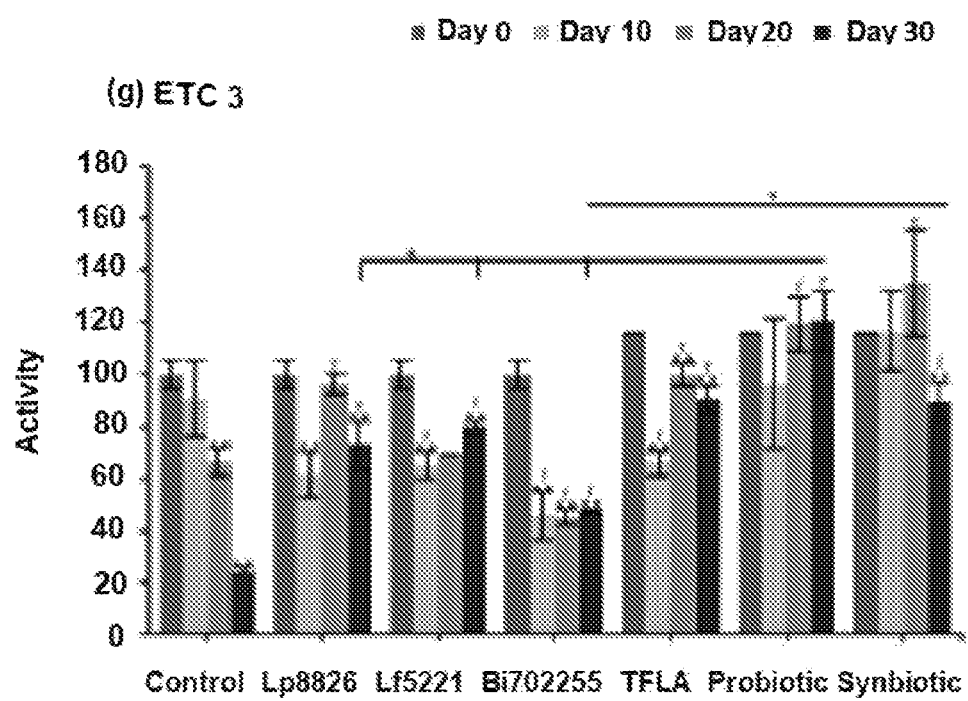
Figure 10H:
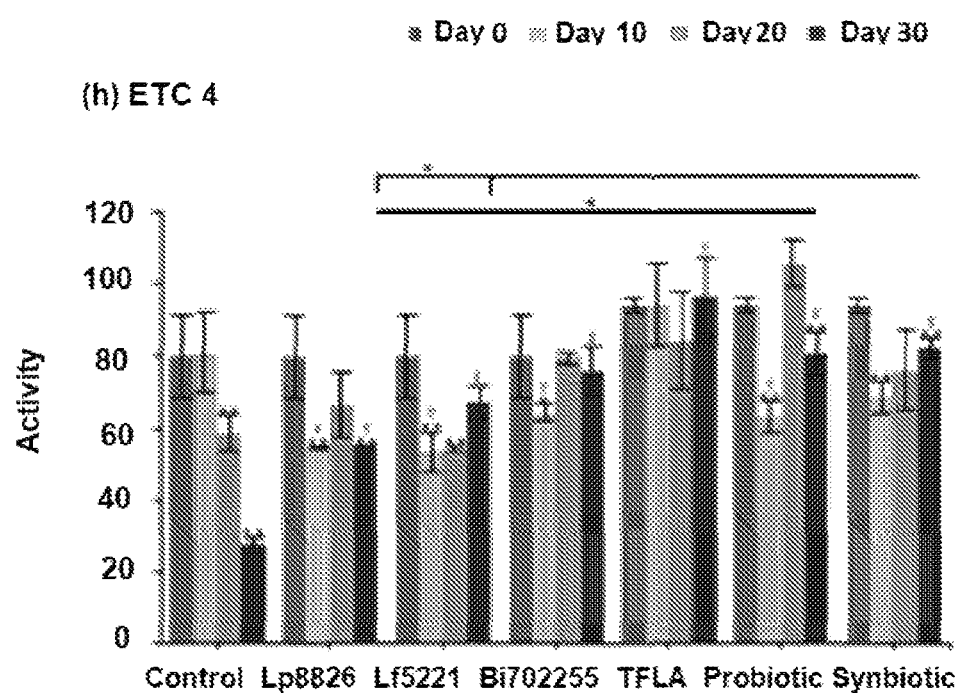

Age-Related Elevations in Oxidative Stress are Alleviated by Probiotic and/or Prebiotic Treatment The gradual accumulation of oxidative stress is a major contributor to aging and in the present model an increase in oxidants and corresponding decrease in antioxidant enzyme activity was dually observed. The level of total oxidants (F (3,18)=3.78, p<0.05) was significantly elevated in control *Drosophila* at days 20 and 30 peaking at a 50% increase by day 30 (FIG. 10a; p<0.01). Supplementation only with the probiotic or synbiotic formulation reduced the total oxidant load at day 30, which for both groups was significantly greater than the effect of the individual probiotics or TFLA (p<0.05). Notably, Lf5221, Bi702255 and TFLA all elicited beneficial reductions in total oxidants at day 20. Superoxide dismutase (SOD) is essential for converting superoxide anions in the less harmful hydrogen peroxide. SOD activity (F $(3,18)=3.92$, $p<0.05$) was reduced by 50% in control *Drosophila* from day 0 to day 30 (FIG. 10b; $p<0.01$), an effect that was only positively impacted by the probiotic or synbiotic formulations at days 10, 20 and 30 ($p<0.05$). The TFLA formulation also improved SOD activity at days 10 and 20; however, to a lesser extent than both the probiotic and synbiotic formulations. Similarly, glutathione peroxidase (GPx) activity (F $(3,18)=4.08$, $p<0.05$) which converts hydrogen peroxide to water, was reduced by 42% in aging control *Drosophila* from day 0 to day 30 (FIG. 10c; $p<0.01$). At day 30, Lf5221, the probiotic or synbiotic formulation had beneficial effects, with the synbiotic formulation having more significant impact than any of the other supplementation groups. Finally, lipid peroxidation (LPO) levels (F $(3, 18)=5.31$, $p<0.01$) were significantly elevated by 26% in control *Drosophila* from day 0 to day 30 (FIG. 10d; $p<0.01$); which was reduced at day 30 by Lf5221, TFLA, the probiotic and synbiotic formulations. Again, the synbiotic formulation had a significantly higher impact than the probiotic formulation and any of the individual therapies and was the only group which rescued the level of LPO compared to the day 0 controls ($p<0.01$). Clearly, the synbiotic formulation has the most robust and consistent impact on markers of oxidative stress indicating its combinatorial action.

An elevation in oxidative stress is result of increased production of ROS particles due to dysfunctional mitochondria coupled with a reduction in antioxidant capacity. To test the mitochondrial functionality, the activity of each of the complexes of the ETC were tested before and after supplementation with probiotics and/or prebiotics in aging *Drosophila*. NADH coenzyme Q reductase (ETC complex I) accepts electrons from the Krebs cycle on the electron carrier NADH to transfer them to complex II. ETC complex I's activity (F $(3,18)=4.31$, $p<0.05$) was reduced at days 10, 20 and 30 in control *Drosophila* reaching a 62% decrease in activity by day 30 (FIG. 10e; $p<0.01$). Supplementation with TFLA, the probiotic and synbiotic formulations elevated complex I activity at day 30 with the probiotic and synbiotic formulations completely rescuing its activity ($p<0.01$). Complex II's (succinate dehydrogenase) activity (F $(3,18)=2.53$, $p>0.05$) was also reduced at days 20 and 30 (FIG. 10f; $p<0.05$), though none of the treatments benefited complex II's activity at day 30. However, the TFLA and synbiotic group reduced ETC complex II's activity to the level of the day 0 control ($p>0.05$). Complex III (cytochrome bc1 complex) activity (F $(3, 18)=3.98$, $p<0.05$) was also reduced in the control group by 76% at day 30 compared to day 0 (FIG. 10g; $p<0.01$). At day 30, every probiotic and/or prebiotic group elicited a beneficial effect on complex III activity; however, the probiotic and synbiotic formulations rescued complex III expression to the level of day 0 controls ($p>0.05$). The probiotic formulation had a significantly greater impact than the individual probiotics while the synbiotic formulation was greater than Bi702255. Finally, complex IV (cytochrome c oxidase) activity (F $(3,18)=4.01$, $p<0.05$) was similarly reduced by 67% in control *Drosophila* by day 30 ($p<0.01$), an effect elevated by all probiotic and or prebiotic treatments (FIG. 1 Id; $p<0.05$). Treatment with Lf5221, Bi702255 and TFLA rescued complex IV's activity to the level of day 0 controls however the synbiotic formulation at day 30 had a significantly higher impact than Lp8826 or Lf5221 on complex IV's expression.

Altering Gut Microbiota for Treating Neurological Diseases

We designed novel probiotic and synbiotic formulations optimized to alter the gut microbiota to elicit the most potential impact on neurological diseases. The probiotic formulation contains three probiotic species *Lactobacillus plantarum* NCIMB 8826, *Lactobacillus fermentum* NCIMB 5221 and *Bifidobacterium longum* spp. *infantis* NCIMB 702255 each at a dosage of $1.0\times10^9$ CFU/ml for a total dosage of $3.0\times10^9$ CFU/ml of *Drosophila* media.

To design the synbiotic formulation, a newly characterized polyphenol-rich water extract of Triphala, a poly-herbal formulation, was combined with the probiotic formulation. The prebiotic activity of Triphala was characterized using in vitro batch cultures of isolated *Lactobacillus* and *Bifidobacteria* strains, the in vivo *Drosophila* model as well as a humanized in vitro model of the gastrointestinal tract where in each mode was demonstrated to increase the populations of beneficial bacteria while decreasing the population of pathogenic species. At the same time, Triphala, at a concentration of 0.5% w/v was demonstrated to have no toxicity in *Drosophila*, did not invoke an immune response and even elicited beneficial effects on the *Drosophila*'s longevity and motility indicating a metabolically beneficial effect. Finally, in these physiological measures (longevity and motility), the probiotic and synbiotic formulations demonstrated a combinatorial effect compared to the individual probiotics or Triphala alone.

Discussion

*Drosophila*'s gut microbiota varies significantly with age with a strong expansion of most groups and a disproportionate rise in the pathogenic Gammaproteobacteria spp. and *Enterococcus* spp.[28]. This is a known phenomenon in *Drosophila* reflecting age-related immunosenescence and accumulating intestinal barrier dysfunctions from proinflammatory pathobionts[29]. These changes parallel the age-related variations observed in aging humans[14,19]. Treatment with the probiotic and/or prebiotic agents used in the present study were previously shown to reduce the bacterial load in aging *Drosophila*[21], have immunomodulatory effects[30], regulate metabolism[31] and enhance longevity[28] indicating the potential of a probiotic-based therapeutic agent for age-related disease.

The synbiotic formulation boosted longevity by 60% compared to *Drosophila* on a conventional diet while the probiotic formulation increased longevity by 55%[28]. There have been a handful of other studies indicating the prolongevity potential of probiotic supplementation[32-35] though, described herein is the first study that demonstrates the simultaneous and multi-faceted action of the novel synbiotic formula as described herein on several markers of aging attributing to its prolongevity effects.

Suppression of insulin-like growth factor (IGF)-1 and insulin signaling have been identified as the main mechanisms through which calorie restriction leads to an increase in longevity[36].

In the present study, all levels of metabolic distress in aging control *Drosophila* were rescued by the synbiotic formulation including total weight, glucose and triglyceride levels. Previous studies have shown that downregulation of the dilps and the insulin receptor increases lifespan in *Drosophila*31 and these factors are under dietary regulation[38].

Regarding the insulin-signaling pathway, elevation of dAkt and dTOR along with the reduction of dFOXO were all rescued by the synbiotic treatment, with beneficial yet variable effects by the individual probiotics and TFLA.

Inhibition of TOR signaling with its natural inhibitor rapamycin has been shown to increase longevity in yeast[39], nematodes[40], Drosophila[41] and mice[42] by mimicking the effects of calorie restriction. Downstream of TOR signaling is the FOXO family of transcription factors. AMPK activation by calorie restriction is also linked to elevated FOXO expression and pro-longevity effects[43] including the simultaneous inhibition of ROS production[44], NF-κB induction[45], senescence[46] and prevention of apoptosis[47] along with encouragement of the protective mechanisms of mitophagy and autophagy[48]. Several studies have linked polymorphisms of FOX03 in humans to increased longevity[5,49] while FOX03 overexpression in Drosophila[50] and mice[51] also imparted lifespan extension. Interestingly, several studies indicated that consumption of polyphenols including green tea epigallocatenin, curcumin and resveratrol stimulate FOXO expression and consequently longevity through mechanisms involving increased SOD, GPx and sirtuin 1 expression with decrease in NF-KB, TNF-oc, ROS, inflammation and oxidative stress[52,53]. Likewise, in the present study, FOXO expression was upregulated by the synbiotic formulation.

Similar to the glucose-regulating factors, many of the underlying lipogenic factors were also positively affected by the probiotic and synbiotic formulations. There was an improvement of lipogenesis dysregulation, indicated by the rescued expression of FAS, SREBP and LSD2 in Drosophila supplemented with the synbiotic formulation. The inherent increase in lipogenic ACC and FAS genes in aging control flies was downregulated most significantly by the probiotic and symbiotic formulations, as was the gluconeogenic PEPCK factor. These changes may be attributed to the transcriptional regulation by SREBP, whose expression was reduced to the level of young flies by both the probiotic and synbiotic formulations. Importantly, SREBP regulation is under the control of the IIS pathway, being activated by both Akt and TOR signaling[54]. The regulation of fatty acid lipogenesis is an important consideration to many aspects of age and age-related conditions, particularly inflammation as obesity is inherently linked with a proinflammatory state[55] which is known to be preventable with adequate probiotic and prebiotic treatment[56,57].

It was previously shown that PPARγ mediated responses are central to the synbiotic's action in metabolic stress models in Drosophila melanogaster[31]. PPARγ is highly expressed in the adipose tissue and a key regulator of lipogenesis and adipogenesis[58] as well as a major insulin sensitizer[59]. Further PPARγ expression in other tissues is thought to regulate their metabolism and the inflammatory response[61] making it at the hub of many aging hypotheses. In the present study, the Drosophila PPARγ target E75 was significantly downregulated in aging control Drosophila, an effect that was improved only in the probiotic and synbiotic groups with the latter actually increasing PPARγ expression over time. This effect would explain the beneficial action on the lipogenesis factors and insulin sensitivity supporting the notion that the synbiotic treatment is regulating metabolic stress in aging Drosophila at a high level and explaining the broad metabolic effects Aging is associated with immunosenescence caused by an exhaustion of stem cells reducing the immune system's regenerative capacity, accumulation of antigens and thymic atrophy[62]. Dysfunctional immune cells disable the body from mounting an appropriate immune response leading to the accumulation of damaged cells that release proinflammatory cytokines. Chronic low-grade inflammation (inflammaging) is associated with many age-related diseases such as neurodegeneration, cardiovascular disease, insulin resistance, diabetes, osteoporosis, cognitive decline, dementia, frailty, cancer and importantly, mortality (rev. in[63]).

The gut microbiota of elderly persons reflects a pro-inflammatory constitution enriched in Proteobacteria spp. and lacking butyrate producing bacteria2. With age, the integrity of the GIT epithelial lining becomes compromised allowing the infiltration of bacteria and bacterial products into the host's bloodstream contributing to inflammaging[64]. All of these factors involve the gut microbiota[63], and age-related variations in the microbiota reduce gut epithelial integrity and induce intestinal dysplasia[66]. The proinflammatory environment also encourages NF-κB activation through LPS-TLR4 interaction as well as the differentiation of naTve T cells into proinflammatory Thl7 cells67. The gradual accumulation of chronic low-grade inflammaging could be the source of many age-related chronic diseases as inflammation is comorbid with elevated ROS production, mitochondrial dysfunction and metabolic abnormalities.

As previously shown, there is an upregulation of proinflammatory pathobionts in aging Drosophila, which were downregulated by the synbiotic formulation[28]. Indeed, aging Drosophila have been shown to be more prone to infection and have an impaired immune system, such as phagocytosis and melanization[61]. A general increase in immune-related genes, increased bacterial loads and more persistent AMP activation after infection resembling the chronic-inflammation state observed in humans has also been observed in Drosophila. In the present study, there was an age-related decline in innate immune functionality in control Drosophila. In particular, there was a decline in the active immunological agents against both gram-positive (S. aureus) and gram-negative (E. coli) challenges, an effect that was significantly impacted by all the probiotic treatments, but to the greatest extent, by the probiotic and synbiotic formulations. This could reflect the decreased ability of aging Drosophila to mount an immune attack against invading pathogens as previously noted[70]. In contrast to other studies that observed an increase in immune gene expression[68], a decrease in the expression of Duox and IMD was observed in aging control flies indicating a weakening of the innate immune response and supporting the weakened immunity to a pathogenic insult as observed in the agar diffusion assay. Duox and IMD are among the first line of defense of the Drosophila innate immune system and regulated directly by antigen recognition of invading pathogens, so, it is possible that the response of the core immune-modulating cells in the fat body is compromised by age affecting the production of Duox and IMD. This could include the Janus Kinase/Signal Transducer Activator of Transcription (JNK/STAT) pathway which has been shown to have competing or cooperative action on the systemic immune response in Drosophila[71].

Despite the decrease in IMD expression in aging Drosophila, an increase in AMP expression, particularly Attacin A, Defensin and Diptercin, was observed and dramatically benefitted by both individual probiotic, prebiotic and the probiotic and synbiotic formulation supplementation. This has been previously observed[72] and directly linked to intestinal barrier dysfunction, which is correlated to lifespan in Drosophila[73]. The reason for the discrepancy between the IMD signaling and AMP expression could be due to the different levels of regulation of AMP expression. Elevated AMP expression in aging flies is correlated to an increase in oxidative stress[74]. Some of the AMPs including Attacin A are co-regulated by inflammatory elements such as the AP-I and NF-κB proteins as well as HDAC activity[72]. Also, the AMPs are influenced by hormonal signaling, namely 20-hydroxyecdysone and juvenile hormone[75], which are differentially affected by aging. AMP expression is also impacted by IIS[68] which could explain the dramatic impact of probiotic treatment on AMP expression in aging Drosophila. Indeed, dFOXO was shown to regulate AMP expression, especially in conditions when the Toll and IMD pathways are defective[76].

Mitochondria progressively lose their energetic capacity with age[77] along with morphological changes, reduction in numbers, loss of protein quantity and mtDNA mutations[78]. Dysregulation of mitophagy and the mitochondrial fission-fusion cycles also compromises the mitochondrial integrity leading to elevated ROS production and consecutive mitochondrial damage[79].

A decline in mitochondrial functionality was confirmed in the present study as the activity of each of the ETC complexes in control flies was reduced over time. The mitochondria play a key role in aging and Drosophila have been identified as powerful model for studying mitochondrial activity in age[80]. A similar phenomena was observed in various tissues in mice and rats, though decline in activities of only complexes I and IV were observed81 while the activity of complexes II and III remained relatively unchanged[82]. TFLA, the probiotic and synbiotic formulations were able to increase ETC complex 1, 3 and 4 activities at day 30 compared to controls, which is very significant in demonstrating how a probiotic treatment can influence mitochondrial complex integrity and consequently the production of ROS particles.

One of the key regulators of mitochondrial biogenesis is the PGC-1 family of transcriptional coactivators, whose expression declines with age[83]. The loss of PGC-1a is associated with a reduction in mitochondrial biogenesis, reduced fission-fusion cycles and dysfunctions in mitophagy[84]. Nutrient deprivation is a key modulator of mitochondrial dynamics as calorie restriction will lower the AMP/ATP and NADH/NAD+ ratios which ultimately stimulates mitochondrial biogenesis and activity through PGC-1 a and SIRT1, respectively. It was shown in Drosophila that overexpression of the PGC-1 a homology (dPGC-1/spargel) was sufficient to increase mitochondrial activity and that tissue-specific expression of dPGC-1 in the digestive tract extends longevity[83]. Supporting this, E75, the Drosophila PPARγ target, was shown to decline with age in the present study, likely representing the decline in PGC-1 a equivalents. The individual probiotic treatment offered little benefit to E7S expression; however, treatment with either the probiotic or synbiotic formulations elevated E75 expression at day 30. This indicates that the management of PPARγ can be one of the critical mechanisms through which the gut microbiota is managing longevity through mitochondrial complex integrity.

ROS production is an essential part of health, though in excess promotes disease. Immunosenescence aggravates redox stress and vice versa stimulating a positive-feedback loop between ROS production and inflammation[85]. ROS levels were significantly elevated in the current aging model as control Drosophila saw an increase in total oxidants and LPO levels with significant decreases in SOD and GPx activity. The probiotic and synbiotic formulations had a mild impact on the antioxidant enzyme activities, however significantly reduced the levels of total oxidant and LPO, with the synbiotic formulation being more significant in the latter. This is very significant in the context of neurodegeneration as there are a high level of PUFAs in neuronal membranes and the level of LPO in Alzheimer's disease is correlated with the degree of cognitive impairment[86].

In the present study, an optimized probiotic formulation, an exemplary formulation as provided herein, containing three bioactive probiotics was combined with a novel polyphenol-rich prebiotic Triphala to create a novel synbiotic formulation that promotes longevity. The synbiotic formulation has a combinatorial effect on various markers of aging including the basic signaling pathways mat manage the cross-regulation of these markers. By understanding how the gut microbiota and probiotic treatments intersect with these key aging pathways, specific formulations may be prescribed early in life to prevent chronic disease onset including cardiovascular disease, diabetes, obesity, cancer and even neurodegeneration.

Materials and Methods

Cultivation of Probiotics

Three probiotic strains, *Lactobacillus plantarum* NCIMB 8826 (Lp8826), *Lactobacillus fermentum* NCIMB 5221 (Lf5221) and *Bifidobacteria longum* spp. *infantis* NCIMB 702255 (Bi702255) were obtained from NCIMB culture collection (Aberdeen, Scotland, UK). Cells were cultured in Man-Rogosa-Sharpe (MRS) media obtained from Sigma Aldrich (Oakville, ON, Canada) at 37° C. on MRS-agar plates or in liquid media. After one round of liquid culture, several bacterial stocks were made in MRS containing 20% (v/v) glycerol and stored at −80° C. As constant culturing was required to carry out all experiments, bacterial stocks were renewed from the frozen stock bi-weekly in order to maintain culture purity. To preform each individual experiment, a 1% (v/v) inoculum was used for subculturing, incubated at 37° C. for 18 h and removed immediately before use.

Probiotic and Synbiotic Formulation

The dried components of Triphala (TFLA; *Emblica officinalis, Terminalia bellirica* and *Terminalia chebula*) were obtained from the Ayurvedic Pharmacy at Banaras Hindu University in Varanasi, India. Each component was individually weighed and combined in equal parts (by weight) before being manually crushed and ground with a mortar and pestle. The 5 g of TFLA powder was combined with 1 L of the *Drosophila* media during the boiling process to make a final concentration of 0.5% TFLA in the complete media. The probiotic formulation contained a total of 3.0× 109 CFU/ml of probiotics with equal distribution between Lp8826 (1.0×109 CFU/ml), Lf5221 (1.0×109 CFU/ml) and Bi702255 (1.0×109 CFU/ml). The synbiotic formulation contained the described probiotic formulation in combination with the 0.S % addition of TFLA powder.

*Drosophila* Husbandry

Wildtype *Drosophila melanogaster* (Oregon R) were procured from the Bloomington *Drosophila* Stock Center (Indiana University, Bloomington Indiana). Flies were reared on a standard cornmeal-sucrose-yeast media without active yeast culture prepared by boiling the cornmeal (83 g), sucrose (SO g) and yeast extract (30 g) in distilled water for 30 min. *Drosophila* were kept in controlled conditions with a 12 h:12 h light-dark cycle at 20° C. To prepare the *Drosophila* bottles inoculated with probiotics and/or pathogenic bacteria, the overnight cultures as described were centrifuged at 3000×g for 10 min at 4° C. The pellet was washed once and resuspended in 0.8S % (w/v) physiological saline. Total colony counts were determined by spectrophotometry compared to a standard curve prepared with colony forming units (CFUs) on MRS plates. Inoculated media was prepared by partitioning the concentrated bacterial culture into the cooled, yet liquid, media to the indicated final concentrations measured as CFU/ml media. This is a verified method of oral-inoculation to flies as bacterial cells remained viable in the *Drosophila* media for up to two weeks before a detectable loss of concentration by daily CFU counting. Nevertheless, flies were transferred to new inoculated bottles every 3-4 days during the course of an experiment.

Metabolic Measurements in *Drosophila*

Body weight was assessed by weighing ten flies in replicates of five at the time of anesthization. Glucose measurements were taken from both hemolymph and whole-body homogenates of *Drosophila* representing the levels of circulating and total glucose, respectively. Hemolymph was extracted by piercing anesthetized *Drosophila* with a fine tungsten needle, placing them in a small tube perforated with several holes situated in a larger tube and centrifuged for 10 min at 4000 rpm. For the whole-body homogenates, the total protein content was first determined using a Bradford Assay and resultant quantification of metabolic markers was standardized against the total protein content in order to account for variations in fly mass. Following, the homogenate was heat-treated for 20 min at 70° C. to remove any complexes. Glucose levels were measured in 2 µl of hemolymph or 5 µl of whole-body homogenate using the Glucose (HK) Assay kit (Sigma, Oakvilla, ON, Canada) according to the manufacturer's instructions. Whole-body triglycerides were determined in 10 µl of homogenate using the Triglycerides Liquicolor Test Mono (Stanbio, TX, USA) according to the manufacturer's instructions.

Genetic Variation of Metabolic Markers

RNA was extracted from twenty-five whole flies using Trizol (ThermoFisher, MA, USA) according to the manufacturer's instructions. cDNA was synthesized from 1 µg of RNA measured with the ND-2000 Nanodrop (FisherScientific, Ottawa, ON, Canada) using the High-Capacity cDNA Synthesis Kit (ThermoFisher, MA, USA) according to the manufacturer's instructions. Expression of various immunological factors genes was conducted using SybrGreen (EvaGreen qPCR Mastermix, Diamed, Mississauga, Canada) real-time quantitative PCR (Eco Real-Time PCR System, Illumina, CA, USA). Primers, their sequences and annealing temperatures are listed in Table 3 and final gene expression was calculated using the 2ddCT method relative to the level of ribosomal protein Rp49.

TABLE 3

Primer sequences of *Drosophila melanogaster* metabolic markers

| Gene Name | Sequence | Annealing Temp. | Seq ID No. | Reference |
|---|---|---|---|---|
| Dilp 2 | F: 3'-AGCAAGCCTTTGTCCTT CATCTC-5' | 50° C. | 39 | 87 |
| | R: 3'-ACACCATACTCAGCACC TCGTTG-5' | | 40 | |
| Dilp 3 | F: 3'-TGTGTGTATGGCTTCAA CGCAATG-5' | 50° C. | 41 | 87 |
| | R: 3'-CACTCAACAGTCTTTCC AGCAGGG-5' | | 42 | |
| InR | F: 5'-AACAGTGGCGGATTCGG TT-3' | 54° C. | 43 | 88 |
| | R: 5'-TACTCGGAGCATTGGAG GCAT-3' | | 44 | |
| ACC | F: 3'-TTAGTCAGCTGCAGGCA AAGG-5' | 54° C. | 45 | 89 |
| | R: 3'-CGGAAGCTAACGCCACA CA-5' | | 46 | |
| FAS | F: 3'-CAACAAGCCGAACCCAG ATCTT-5' | 50° C. | 47 | 54 |
| | R: 3'-CAAAGGAGTTCAGGCCG ATGAT-5' | | 48 | |
| PEPCK | F: 3'-CGCCCAGCGACATGGAT GCT-5' | 60° C. | 49 | This study |
| | R: 3'-GTACATGGTGCGACCCT TCA-5' | | 50 | |
| dTOR | F: 3'-GGCCGTCCAGGTTCAAA AAC-5' | 59° C. | 51 | This study |
| | R: 3'-AATCCGGCGATAGTTCC GTC-5' | | 52 | |
| dAkt | F: 3'-GAGTCGTGTGCTCAAGT CCA-5' | 59° C. | 53 | This study |
| | R: 3'-TGCATCACAAAACACAG GCG-5' | | 54 | |

TABLE 3-continued

Primer sequences of Drosophila melanogaster metabolic markers

| Gene Name | Sequence | Annealing Temp. | Seq ID No. | Reference |
|---|---|---|---|---|
| dFOXO | F: 3'-TCGCCGAACTCAGTAAC CAC-5' | 59° C. | 55 | 90 |
|  | R: 3'-TCCTATCAAAGTAGAGG CGCA-5' |  | 56 |  |
| SREBP | F: 5'-GGCAGTTTGTCGCCTGA TG-3' | 56° C. | 57 | This study |
|  | R: 5'-CAGACTCCTGTCCAAGA GCTGTT-3' |  | 58 |  |
| E78 | F: 5'-CAGTGTCTCTCGTTGCT CA-3' | 54° C. | 59 | 90 |
|  | R: 5'-AACCGATTGCTTCGCTC TCT-3' |  | 60 |  |
| LSD | F: 5'-ACTTGTAGTGCCAGTTC CCG-3' | 52° C. | 61 | This study |
|  | R: 5'-ACCAGACTGCTCCACAT TCG-3' |  | 62 |  |
| Rp49 | F: 3'-AGATCGTGAAGAAGCGC ACCAAG-5' | 52° C. | 63 | This study |

Oxidative Stress Markers

Oxidative stress markers were measured from a fresh Drosophila homogenate 5 prepared from 25 flies in Tris-EDTA-TRITON X-100 buffer, pH 7.4 filtered through a fine cloth to remove solid particles. Total oxidants were assayed using 2'-7'-dichlorofluorescein diacetate (DCFA) (Sigma, Oakville, ON) as previously outlined[92]. Briefly, 20 µl of fly homogenate was mixed with 170 µl of Locke's buffer.

Following, 10 µl of 1 mM DCFA solution was added to each well and after 3 min incubation and fluorescently read at 474 nm excitation and 530 nm emission wavelengths.

Quantification was normalized to the amount of protein in each sample.

SOD activity was tested using a xanthine-xanthine oxidase reaction to generate superoxide radicals and nitrotetrazolium blue (NBT) reduction as an indicator of superoxide production[93]. Briefly, the working solution consisted of 110 µl of potassium phosphate buffer with 20 mg ml BSA, 6.2S µl catalase (40 U/ml), 6.25 µL of NBT and 50 µl of xanthine (1.8 mM). To the working solution, 7.5 µl of homogenate and 20 µl of xanthine oxidase (XOD, 5 U/ml) was added and incubated at 37° C. for 20 min in the dark with agitation to allow colour to develop. Absorbance of reduced NBT was recorded at 570 nm, compared to a standard curve of SOD and normalized to the amount of protein in the sample GPx activity was assessed based on the oxidation of glutathione (GSSG), which was constantly supplied by an excess of glutathione reductase (GR). To measure GPx activity the consequent reduction of the cosubstrate NADPH was monitored at 340 nm as previous shown[94] with modifications. Briefly, a GPx buffer was made containing 0.5 M sodium phosphate (pH 7.2), 100 mM EDTA and 1.1 mM sodium azide. The GPx assay buffer consisted of 1.33 mM of GSSH and 1.33 U/ml GR in GPx buffer. The assay solution consisted of 160 µl of GPx assay solution, 10 µl of NADPH (5 mM), 20 µl hydrogen peroxide (0.5%) and 15 µl of homogenate. The absorbance at 340 nm was monitored for 3 min and the linear portion of the curve was assessed for GPx activity and quantification was normalized to the amount of protein in the sample.

The level of lipid peroxidation (LPO) was assessed as bound malondialdehyde (MDA) was hydrolyzed in the presence of butylated hydroxytolene (BHT) as adapted from[95]. The reaction solution contained 10 mM of 1-methyl-2-phenylindole in a 3:1 mixture of acetonitrile:methanol. To 120 µl of this solution, 20 µl of sample and 40 µl of 37% HCl was added and allowed to react at 100° C. for 60 min. The absorbance of the resulting solution was measured at 550 nm, compared to MDA standard solution and normalized to the amount of total protein in the sample.

Agar Disk Diffusion Assay

To assess the Drosophila's direct ability to inhibit the growth of both E. coli and S. aureus, hemolymph from flies reared for 10 days on media containing the probiotic and/or prebiotic therapy was placed on a lawn of either S. aureus or E. coli on Tryptose Sulfite Cycloserine (TSC)-agar (Sigma, Oakville, ON) plates. To isolate hemolymph, 50 flies were pierced with a fine needle in the thorax region and placed in a small Eppendorf tube perforated with several holes, situated in a larger Eppendorf tube. The pierced flies were centrifuged at 3000×g, at 4° C. for 20 min to remove sufficient hemolymph for analysis. The hemolymph (20 1) was diluted to 50 µl with sterile physiological saline and pipetted onto a 5 mm sterile circle of filter paper situated on the nutrient-agar plates freshly spread with 100 µl of overnight S. aureus or E. coli solution. The plates inoculated with the hemolymph saturated filter paper were placed at 37° C. for 24 h and the zone of inhibition (diameter) was measured. Each treatment was run in triplicate on separate nutrient-agar plates.

Inflammatory Markers

The expression the genetic inflammatory markers was assessed as described in the metabolic markers section, except using the primer sequences outlined in Table 4.

TABLE 4

Primer sequences of Drosophila melanogaster inflammatory markers

| Gene Name | Sequence | SEQ ID NO: | Annealing Temp | Reference |
|---|---|---|---|---|
| Duox | F: GCTGCACGCCAACCAC AAGAGACT | 64 | 54° C. | 90 |
| | R: CACGCGCAGCAGGATG TAAGGTTT | 65 | | |
| IMD | F: TCGAATGCCAATAATC TGCA | 66 | 52° C. | 90 |
| | R: CGCGATGCTGGGACTC CCAC | 67 | | |
| Relish | F: TGGGAGGCATACGCAA AGT | 68 | 55° C. | This study |
| | R: CAATTACGCTCCGTGG CTTG | 70 | | |
| Attacin A | F: GGCCCATGCCAATTTA TTCA | 69 | 56° C. | 96 |
| | R: CATTGCGCTGGAACTC GAA | 71 | | |
| Diptericin | F: AGGTGTGGACCAGCGA CAA | 72 | 56° C. | 96 |
| | R: TGCTGTCCATATCCTC CATTCA | 73 | | |
| Defensin | F: GCACAATGAAGTTCAC CATCGT | 74 | 56° C. | 96 |
| | R: CCACACCCATGGCAAA AAC | 75 | | |

Mitochondrial Electron Transport Chain (ETC) Complex Activity

Mitochondria was isolated from *Drosophila* by homogenizing 40 anesthetized flies in 4 mL of ice-cold hypotonic buffer (25 mM $K_2HPO_4$ and 5 mM MgCb) with a pre-cooled smooth pestle tissue grinder (Corning, NY, USA) on ice. Large pieces were filtered out using a fine nylon mesh and the remaining isolate was flash-frozen on dry ice before being stored at −80° C. Before use, the homogenates underwent 3 freeze-thaw cycles to open the mitochondrial membrane.

ETC complex I (NADH—ubiquinone oxidoreductase) activity was assessed by measuring the electron transfer to decyluniquinone from NADH as previously described[15]. The assay buffer contained potassium phosphate buffer (50 mM, pH 7.2) in addition to BSA (50 mg/mL), potassium cyanide (KCN; 10 mM), NADH (10 mM) and rotenone (1 mM). To start the reaction, 25 μL, of the homogenate was added to 150 μL of the assay buffer in addition to decyluniquinone (10 μM). The change in absorbance at 340 nm was monitored over two minutes and the slope of NADH reduction was recorded and normalized to the total protein in the sample.

ETC complex II (succinate-ubiquinone oxidoreductase) was measured as the rate of 2,6-dicholorophenolindophenol (DCPIP) reduction as previously described[75]. The assay buffer contained potassium phosphate buffer (50 mM, pH 7.6) in addition to BSA (50 mg/mL), potassium cyanide (KCN, 10 mM), succinate (400 mM) and DCPIP (0.015% w/v). To start the reaction, 10 μL of the homogenate in addition to phenazine methosulfate (65 mM) was added to 160 μl of the assay buffer. The rate of reduction was measured at 600 nm over two minutes and the activity of ETC complex II was measured as the linear portion of the slope of DCPIP reduction and normalized to the amount of protein in the sample.

ETC complex III (NADH-cytochrome c oxidoreductase) activity was determined as the rate of antimycin dependent reduction of cytochrome c as previously described[75]. The assay buffer contained potassium phosphate buffer (50 mM, pH 7.2) in addition to oxidized cytochrome c (ImM), KCN (10 mM), EDTA (5 mM), TWEEN-20 (2.5%) and antimycin A (1 mg/mL). To start the reaction, 20 μl of sample homogenate was added to the assay buffer in addition to 10 of decyubiquiol (10 mM). The reduction of cytochrome c was monitored at 550 nm for 2 min both with and without antimycin A and the difference in the reaction rates was taken as the antimycin A sensitive complex activity and normalized to the amount of protein in the sample.

Finally, ETC complex IV (cytochrome c oxidase) activity was determined by monitoring the rate of cytochrome c oxidation. The assay buffer contained potassium phosphate buffer (50 mM, pH 8.0) supplemented with reduced cytochrome c (1 mM). Cytochrome c was reduced by adding a few grains of sodium dithionite to the oxidized cytochrome c solution until the red colour turned to orange and an absorbance ratio greater of 550 run to 565 nm was greater than 6. The reaction was initialized with the addition of 25 µl of the homogenate and the rate of reduction recorded for 3 min at 550 nm. The complex rate was normalized to the total amount of protein in the sample.

Statistics

All statistical analyses were conducted using [R] software. All experiments were conducted with 5 independent trials. Variations in body weight and motility over the dose-curves of probiotic were assessed via one-way ANOVA analyses with Tukey post-hoc analyses. Significance of metabolic markers and genetic expression was assessed with two-way ANOVA with Tukey post-hoc analyses. Significance was determined if $p<0.05$ and evaluation at $p<0.01$.

REFERENCES

1. Patrignani, P., Tacconelli, S. & Bruno, A. Gut microbiota, host gene expression, and aging. *J Clin Gastroenterol* 48 Suppl 1, S28 31 (2014).
2. Biagi, E. et al. Through Ageing, and Beyond: Gut Microbiota and Inflammatory Status in Seniors and Centenarians. 5, e10667 (2010).
3. Claesson, M. J. et al. Composition, variability, and temporal stability of the intestinal microbiota of the elderly. *Proc. Natl. Acad. Sci.* U.S.A. 108, (2011).
4. Weinert, B. T. & Timiras, P. S. Invited review: Theories of aging. J Appl Physiol (1985) 95, 1706-1716 (2003).
5. Kenyon, C. J. The genetics of ageing. Nature 464, 504-512 (2010).
6. Govindaraju, D., Atzmon, G. & Barzilai, N. Genetics, lifestyle and longevity: Lessons from centenarians. Appl Transl Genom 4, 23-32 (2015).
7. Park, D. C. & Yeo, S. G. Aging. Korean J Audio! 17, 39-44 (2013).
8. Troen, B. R. The biology of aging. Mt Sinai J Med 70, 3-22 (2003).
9. Khalyavkin, A. V. & Krufko, V. N. Early Thymus Involution-Manifestation of an Aging Program or a Program of Development? Biochemistry QAosc) 80, 1622-1625 (2015).
10. Sanz, A. & Stefanatos, R. K. A. The mitochondrial free radical theory of aging: a critical view. Curr Aging Sci 1, 10-21 (2008).
11. Fontana, L., Partridge, L. & Longo, V. D. Extending healthy life span-from yeast to humans. Science 328, 321-326 (2010).
12. Biagi, E. et al. Through ageing, and beyond: gut microbiota and inflammatory status in seniors and centenarians. PLoS One 5, (2010).
13. Claesson, M. J. et al. Composition, variability, and temporal stability of the intestinal microbiota of the elderly. Proc. Natl. Acad. Sci. U.S.A. 108 Suppl 1, 4586^591 (201 1).
14. Biagi, E. et al. Gut Microbiota and Extreme Longevity. Curr Biol 26, 1480-1485 (2016).
15. Park, S.-H. et al. Comparative analysis of gut microbiota in elderly people of urbanized towns and longevity villages. BMC Microbiol 15, 49 (2015).
16. Keenan, M. J., Marco, M. L., Ingram, D. K. & Martin, R. J. Improving healthspan via changes in gut microbiota and fermentation. Age (Dordr) 37, 98 (2015).
17. Shoaie, S. et al. Quantifying Diet-Induced Metabolic Changes of the Human Gut Microbiome. Cell Metabolism 22, 320-331 (2015).
18. Claesson, M. J. et al. Gut microbiota composition correlates with diet and health in the elderly. Nature 488, 178-184 (2012).
19. Kong, F. et al. Gut microbiota signatures of longevity. Curr Biol 26, R832-R833 (2016).
20. Layden, B. T., Angueira, A. R., Brodsky, M., Durai, V. & Lowe, W. L. J. Short chain fatty acids and their receptors: new metabolic targets. Transl Res 161, 131-140 (2013).
21. Burokas, A., Moloney, R. D., Dinan, T. G. & Cryan, J. F. Microbiota regulation of the Mammalian gut-brain axis. Adv Appl Microbiol 91, 1-62 (2015).
22. Dinan, T. G. & Cryan, J. F. Gut instincts: microbiota as a key regulator of brain development, ageing and neurodegeneration. The Journal of Physiology 595, 489-503 (2017).
23. Jeong, J.-J., Kim, K. A., Hwang, Y.-J., Han, M. J. & Kim, D.-H. Anti-inflammaging effects of *Lactobacillus brevis* OW38 in aged mice. Bene/Microbes 7, 707-718 (2016).
24. Sharma, R. et al. Dietary supplementation of milk fermented with probiotic *Lactobacillus fermentum* enhances systemic immune response and antioxidant capacity in aging mice. Nutr Res 34, 968-981 (2014).
25. Matsumoto, M., Kurihara, S., Kibe, R., Ashida, H. & Benno, Y. Longevity in mice is promoted by probiotic-induced suppression of colonic senescence dependent on upregulation of gut bacterial polyamine production. PLoS One 6, e23652 (20U).
26. Grompone, G. et al. Anti-inflammatory *Lactobacillus rhamnosus* CNCM I-3690 strain protects against oxidative stress and increases lifespan in *Caenorhabditis elegans*. 7, e52493 (2012).
27. Zhao, Y. et al. *Lactobacillus salivarius* strain FDB89 induced longevity in *Caenorhabditis elegans* by dietary restriction. J Microbiol 51, 183-188 (2013).
28. Westfall, Lomis, N. & Prakash, S. Characterization of Triphala as a novel prebiotic and its activity in an optimized synbiotic formulation: linking longevity, motility and the gut microbiota.
29. Clark, R. I. et al. Distinct Shifts in Microbiota Composition during *Drosophila* Aging Impair Intestinal Function and Drive Mortality. Cell Rep 12, 1656-1667 (2015).
30. Westfall, S., Lomis, N. & Prakash, S. Combinatorial effects of probiotics and prebiotics on inflammation and oxidative stress in *Drosophila melanogaster*. Inflamm Bowel Dis
31. Westfall, S., Lomis, N. & Prakash, S. The combination of a polyphenol ic prebiotic with a novel probiotic formulation on genetic markers of metabolic stress in *Drosophila melanogaster* dietary models of diabetes and obesity. J Func Foods
32. Lee, J. et al. Evaluation of probiotic characteristics of newly isolated *Lactobacillus* spp.: immune modulation and longevity. Int J Food Microbiol 148, 80-86 (201 1).
33. Han, B. et al. Microbial Genetic Composition Tunes Host Longevity. Cell 169, 1249-1262.el3 (2017).
34. Kibe, R. et al. Upregulation of colonic luminal polyamines produced by intestinal microbiota delays senescence in mice. Sci Rep 4, 4548 (2014).
35. Valentini, L. et al. Impact of personalized diet and probiotic supplementation on inflammation, nutritional parameters and intestinal microbiota—The 'RISTOMED project': Randomized controlled trial in healthy older people. Clin Nutr 34, 593-602 (2015).

36. Anisimov, V. N. & Bartke, A. The key role of growth hormone-insulin-IGF-1 signaling in aging and cancer. CritRev Oncol Hematol 87, 201-223 (2013).
37. Gronke, S., Clarke, D.-F., Broughton, S., Andrews, T. D. & Partridge, L. Molecular evolution and functional characterization of *Drosophila* insulin-like peptides. PLoS Genet 6, e1000857 (2010).
38. Min, K.-J., Yamamoto, R., Buch, S., Pankratz, M. & Tatar, M. *Drosophila* lifespan control by dietary restriction independent of insulin-like signaling. Aging Cell 7, 199-206 (2008).
39. Powers, R. W. 3., Kaeberlein, M., Caldwell, S. D., Kennedy, B. K. & Fields, S. Extension of chronological life span in yeast by decreased TOR pathway signaling. Genes Dev 20, 174-184 (2006).
40. Robida-Stubbs, S. et al. TOR signaling and rapamycin influence longevity by regulating SKN-l/Nrf and DAF-16/FoxO. Cell Metabolism 15, 713-724(2012).
41. Bjedov, I. et al. Mechanisms of life span extension by rapamycin in the fruit fly *Drosophila melanogaster*. Cell Metabolism 1 1, 35-46 (2010).
42. Harrison, D. E. et al. Rapamycin fed late in life extends lifespan in genetically heterogeneous mice. Nature 460, 392-395 (2009).
43. Greer, E. L. et al. An AMPK-FOXO pathway mediates longevity induced by a novel method of dietary restriction in *C. elegans*. Curr Biol 17, 1646-1656 (2007).
44. Murakami, S. Stress resistance in long-lived mouse models. Exp Gerontol 41, 1014-1019 (2006).
45. Navab, M., Gharavi, N. & Watson, A. D. Inflammation and metabolic disorders. Curr Opin Clin Nutr Metab Care 11, 459-464 (2008).
46. Johnson, S. C, Rabinovitch, P. S. & Kaeberlein, M. mTOR is a key modulator of ageing and age-related disease. Nature 493, 338-345 (2013).
47. Barthelemy, C, Henderson, C. E. & Pettmann, B. Foxo3a induces motoneuron death through the Fas pathway in cooperation with INK. BMCNeurosci 5, 48 (2004).
48. Liesa, M. & Shirihai, O. S. Mitochondrial dynamics in the regulation of nutrient utilization and energy expenditure. Cell Metabolism 17, 491-506 (2013).
49. Zeng, Y. et al. GxE interactions between FOXO genotypes and drinking tea are significantly associated with prevention of cognitive decline in advanced age in China. J Gerontol A Biol Sci Med Sci 70, 426-433 (2015).
50. Giannakou, M. E. et al. Long-lived *Drosophila* with overexpressed dFOXO in adult fat body. Science 30S, 361 (2004).
51. Bluher, M., Kahn, B. B. & Kahn, C. R. Extended longevity in mice lacking the insulin receptor in adipose tissue. Science 299, 572-574 (2003).
52. Morris, B. J., Willcox, D. C, Donlon, T. A. & Willcox, B. J. FOX03: A Major Gene for Human Longevity-A Mini-Review. Gerontology 61, 515-525 (2015).
53. Niu, Y. et al. The phytochemical, EGCG, extends lifespan by reducing liver and kidney function damage and improving age-associated inflammation and oxidative stress in healthy rats. Aging Cell 12, 1041-1049 (2013).
54. Porstmann, T. et al. SREBP activity is regulated by mTORCl and contributes to Akt-dependent cell growth. Cell Metabolism 8, 224-236 (2008).
55. Saad, M. J. A., Santos, A. & Prada, P. O. Linking Gut Microbiota and Inflammation to Obesity and Insulin Resistance. Physiology (Bethesda) 31, 283-293 (2016).
56. Anhe, F. F. et al. A polyphenol-rich cranberry extract protects from diet-induced obesity, insulin resistance and intestinal inflammation in association with increased *Akkermansia* spp. population in the gut microbiota of mice. Gut 64, 872-883 (2015).
57. Cani, P. D., Osto, M., Geurts, L. & Everard, A. Involvement of gut microbiota in the development of low-grade inflammation and type 2 diabetes associated with obesity. Gut Microbes 3, 279-288 (2012).
58. Janani, C. & Ranjitha Kumari, B. D. PPAR gamma gene—a review. Diabetes Metab Syndr 9, 46-50 (2015).
59. Ahmadian, M. et al. PPARgamma signaling and metabolism: the good, the bad and the future. Nat Med 19, 557-566 (2013).
60. Ulrich-Lai, Y. M. & Ryan, K. K. PPARgamma and stress: implications for aging. Exp Gerontol 48, 671-676 (2013).
61. Barbieri, M. et al. Gender specific association of genetic variation in peroxisome proliferator-activated receptor (PPAR)gamma-2 with longevity. Exp Gerontol 39, 1095-1100 (2004).
62. Cannizzo, E. S., Clement, C. C, Sahu, R., Folio, C. & Santambrogio, L. Oxidative stress, inflamm-aging and immunosenescence. J Proteomics 74, 2313-2323 (201 1).
63. Buford, T. W. (Dis)Trust your gut: the gut microbiome in age-related inflammation, health, and disease. Microbiome 5, 80 (2017).
64. Steele, A. K. et al. Contribution of intestinal barrier damage, microbial translocation and HIV-1 infection status to an inflammaging signature. PLoS One 9, e97171 (2014).
65. Hardy, H., Harris, J., Lyon, E., Beal, J. & Foey, A. D. Probiotics, Prebiotics and Immunomodulation of Gut Mucosal Defences: Homeostasis and Immunopathology. Nutrients 5, 1869-1912 (2013).
66. Ayyaz, A. & Jasper, H. Intestinal inflammation and stem cell homeostasis in aging *Drosophila melanogaster*. Front Cell Infect Microbiol 3, 98 (2013).
67. Atarashi, K. et al. Induction of colonic regulatory T cells by indigenous *Clostridium* species. Science 331, 337-341 (2011).
68. Eleftherianos, I. & Castillo, J. C. Molecular mechanisms of aging and immune system regulation in *Drosophila*. Int J Mol Sci 13, 9826-9844 (2012).
69. Myllymaki, H., Valanne, S. & Ramet, M. The *Drosophila* imd signaling pathway. J Immunol 192, 3455-3462 (2014).
70. Kim, Y. S. et al. Role of xanthine dehydrogenase and aging on the innate immune response of *Drosophila*. J Am Aging Assoc 24, 187-193 (2001).
71. Uvell, H. Signaling and transcriptional regulation of antimicrobial peptide genes in. 1-70 (2006).
72. Ganesan, S., Aggarwal, K., Paquette, N. & Silverman, N. NF-xB/Rel Proteins and the Humoral Immune Responses of *Drosophila melanogaster*. Current topics in microbiology and immunology 349, 25-60 (2011).
73. Rera, M., Clark, R. I. & Walker, D. W. Intestinal barrier dysfunction links metabolic and inflammatory markers of aging to death in *Drosophila*. Proc. Natl. Acad. Sci. U.S.A. 109, (2012).
74. Landis, G. N. et al. Similar gene expression patterns characterize aging and oxidative stress in *Drosophila melanogaster*. Proc. Natl. Acad Sci. U.S.A. 101, 7663-7668 (2004).
75. Spinazzi, M., Casarin, A., Pertegato, V., Salviati, L. & Angelini, C. Assessment of mitochondrial respiratory chain enzymatic activities on tissues and cultured cells. Nat Protoc 7, 1235-1246 (2012).
76. Becker, T. et al. FOXO-dependent regulation of innate immune homeostasis. Nature 463, 369-373 (2010).

77. Wallace, D. C. A mitochondrial paradigm of metabolic and degenerative diseases, aging, and cancer: a dawn for evolutionary medicine. Annu Rev Genet 39, 359-407 (2005).
78. Bratic, A. & Larsson, N.-G. The role of mitochondria in aging. J Clin Invest 123, 951-957 (2013).
79. D'Aquila, P., Bellizzi, D. & Passarino, G. Mitochondria in health, aging and diseases: the epigenetic perspective. Biogerontology 16, 569-585 (2015).
80. Cho, J., Hur, J. H. & Walker, D. W. The role of mitochondria in *Drosophila* aging. Exp Gerontol 46, 331-334 (2011).
81. Manczak, M., Jung, Y., Park, B. S., Partovi, D. & Reddy, P. H. Time-course of mitochondrial gene expressions in mice brains: implications for mitochondrial dysfunction, oxidative damage, and cytochrome c in aging. J Neurochem 92, 494-504 (2005).
82. Navarro, A. & Boveris, A. Brain mitochondrial dysfunction and oxidative damage in Parkinson's disease. J Bioenerg Biomembr 41, 517-521 (2009).
83. Rera, M. et al. Modulation of longevity and tissue homeostasis by the *Drosophila* PGC-1 homolog. Cell Metabolism 14, 623-634 (2011).
84. Wenz, T. Mitochondria and PGC-1 alpha in Aging and Age-Associated Diseases. J Aging Res 201 1, 810619 (2011).
85. de Almeida, A. J. P. O., Ribeiro, T. P. & de Medeiros, I. A. Aging: Molecular Pathways and Implications on the Cardiovascular System. OxidMed Cell Longev 2017, U.S. Pat. No. 7,941,563 (2017).
86. Pratico, D. & Sung, S. Lipid peroxidation and oxidative imbalance: early functional events in Alzheimer's disease. J Alzheimers Dis 6, 171-175 (2004).
87. Luo, J., Lushchak, O. V., Goergen, P., Williams, M. J. & Nassel, D. R. *Drosophila* insulin-producing cells are differentially modulated by serotonin and octopamine receptors and affect social behavior. 9, e99732 (2014).
88. Storelli, G. et al. *Lactobacillus plantarum* Promotes *Drosophila* Systemic Growth by Modulating Hormonal Signals through TOR-Dependent Nutrient Sensing. Cell Metabolism 14, 403-414 (2011).
89. Okamura, T., Shimizu, H., Nagao, T., Ueda, R. & Ishii, S. ATF-2 regulates fat metabolism in *Drosophila*. Mo I Biol Cell 18, 1519-1529 (2007).
90. Ha, E.-M. et al. Coordination of multiple dual oxidase-regulatory pathways in responses to commensal and infectious microbes in *Drosophila* gut. Nature Publishing Group 10, 949-957 (2009).
91. Westfall, Lomis, N., Singh, S. P. & Prakash, S. Ferulic acid produced by *Lactobacillus fermentum* NCIMB S221 reduced symptoms of metabolic syndrome in *Drosophila melanogaster*. Microbial Biochem Technol 8, 272-284 (2016).
92. Hosamani, R. Acute exposure of *Drosophila melanogaster* to paraquat causes oxidative stress and mitochondrial dysfunction. Arch Insect Biochem Physiol 83, 25-40 (2013).
93. Mockett, R. J., Bayne, A.-C. V., Sohal, B. H. & Sohal, R. S. Biochemical assay of superoxide dismutase activity in *Drosophila*. Methods Enzymol 349, 287-292 (2002).
94. Weydert, C. J. & Cullen, J. J. Measurement of superoxide dismutase, catalase and glutathione peroxidase in cultured cells and tissue. Nat Protoc 5, 51-66 (2010).
95. Gerard-Monnier, D. et al. Reactions of 1-methyl-2-phenylindole with malondialdehyde and 4-hydroxyalkenals. Analytical applications to a colorimetric assay of lipid peroxidation. Chem Res Toxicol 11, 1176-1183 (1998).
96. Tsai, C. W., McGraw, E. A., Ammar, E.-D., Dietzgen, R. G. & Hogenhout, S. A. *Drosophila melanogaster* mounts a unique immune response to the Rhabdovirus sigma virus. Applied and Environmental Microbiology 74, 3251-3256 (2008).

A number of embodiments of the invention have been described.

Nevertheless, it can be understood that various modifications may be made without departing from the spirit and scope of the invention. Accordingly, other embodiments are within the scope of the following claims.

What is claimed is:

1. A method of lowering circulating blood glucose level and total glucose level, lowering triglyceride level, and managing insulin resistance in an individual in need thereof,
comprising administering to the individual about one to four dosages of a probiotic formulation comprising a combination of three isolated bacterial strains, wherein the three isolated bacterial strains are *Lactobacillus fermentum* NCIMB 5221, isolated *Lactobacillus plantarum* NCIMB 8826, and isolated *Bifidobacterium longum* NCIMB 702255, wherein the lowering is when compared to a corresponding individual not administered with the formulation.

2. The method of claim 1, wherein the individual has type II diabetes, insulin resistance, hyperglycemia, or hyperglyceridemia.

3. The method of claim 1, wherein a prebiotic composition is also administered to the individual.

4. The method of claim 3, wherein the prebiotic composition is polyherbal comprising equal amounts of *Emblica offcinalis, Terminalia chebula* and *Terminalia belerica*.

5. The method of claim 1, wherein the three bacterial strains are live or dead.

6. The method of claim 1, wherein each of the three bacterial strains is present at $1\times10^5$ CFU/ml to $10^{11}$ CFU/ml of the formulation, or between $10^5$ CFU/gm and $3.0\times10^{11}$ CFU/gm of the formulation.

7. The method of claim 1, wherein the total of the three bacterial strains present is $3.0\times10^9$ CFU/ml or $3.0\times10^9$ CFU/gm of the formulation.

8. The method of claim 1, wherein each of the three bacterial strains is present at $1.0\times10^9$ CFU/ml.

9. The method of claim 1, wherein the individual is a human or an animal.

10. The method of claim 1, wherein the formulation is in the form of a solution, a suspension, an emulsion, a powder, a lozenge, a pill, a syrup, a tablet, a capsule, a geltab, an aerosol, a suppository, a chewing gum, a capsule or a sachet.

11. The method of claim 1, wherein the formulation is administered in an edible material, a drink, or a foodstuff.

12. The method of claim 1, wherein the formulation is administered in a fluid or solid dairy product, milk or condensed milk, drinkable yogurt, yogurt, fermented beverage, ice cream, cheese, soy milk, vegetable juice, fruit juice, sports drink, dessert, jelly, candy, baby food, health food, dietary supplement, or dietary additive.

13. A method of slowing the onset or progression of metabolic stress, oxidative stress, and inflammation in an individual in need thereof,
comprising administering to the individual about one to four dosages of a probiotic formulation comprising a combination of three isolated bacterial strains, wherein the three isolated bacterial strains are *Lactobacillus fermentum* NCIMB 5221, isolated *Lactobacillus plantarum* NCIMB 8826, and isolated *Bifidobacterium longum* NCIMB 702255.

14. The method of claim 13, wherein the individual has oxidative stress and/or inflammation.

15. The method of claim 13, wherein a prebiotic composition is also administered to the individual.

16. The method of claim 13, wherein the prebiotic composition is polyherbal comprising equal amounts of *Emblica offcinalis, Terminalia chebula* and *Terminalia belerica*.

17. The method of claim 13, wherein the three bacterial strains are live or dead.

18. The method of claim 13, wherein each of the three bacterial strains is present at $1\times10^5$ CFU/ml to $10^{11}$ CFU/ml of the formulation, or between $10^5$ CFU/gm and $3.0\times10^{11}$ CFU/gm of the formulation.

19. The method of claim 13, wherein the total of the three bacterial strains present is $3.0\times10^9$ CFU/ml or $3.0\times10^9$ CFU/gm of the formulation.

20. The method of claim 13, wherein each of the three bacterial strains is present at about $1.0\times10^9$ CFU/ml.

21. The method of claim 13, wherein the individual is a human or an animal.

22. The method of claim 13, wherein the formulation is in the form of a solution, a suspension, an emulsion, a powder, a lozenge, a pill, a syrup, a tablet, a capsule, a geltab, an aerosol, a suppository, a chewing gum, a capsule or a sachet.

23. The method of claim 13, wherein the formulation is administered in an edible material, a drink, or a foodstuff.

24. The method of claim 13, wherein the formulation is administered in a fluid or solid dairy product, milk or condensed milk, drinkable yogurt, yogurt, fermented beverage, ice cream, cheese, soy milk, vegetable juice, fruit juice, sports drink, dessert, jelly, candy, baby food, health food, dietary supplement, or dietary additive.

* * * * *

SEQUENCE LISTING

```
<160> NUMBER OF SEQ ID NOS: 75

<210> SEQ ID NO 1
<211> LENGTH: 19
<212> TYPE: DNA
<213> ORGANISM: Drosophila melanogaster

<400> SEQUENCE: 1
aacagtggcg gattcggtt                                                19

<210> SEQ ID NO 2
<211> LENGTH: 21
<212> TYPE: DNA
<213> ORGANISM: Drosophila melanogaster

<400> SEQUENCE: 2
tactcggagc attggaggca t                                             21

<210> SEQ ID NO 3
<211> LENGTH: 23
<212> TYPE: DNA
<213> ORGANISM: Drosophila melanogaster

<400> SEQUENCE: 3
```
agcaagcctt tgtccttcat ctc                                          23

<210> SEQ ID NO 4
<211> LENGTH: 23
<212> TYPE: DNA
<213> ORGANISM: Drosophila melanogaster

<400> SEQUENCE: 4
acaccatact cagcacctcg ttg                                          23

<210> SEQ ID NO 5
<211> LENGTH: 24
<212> TYPE: DNA
<213> ORGANISM: Drosophila melanogaster

<400> SEQUENCE: 5
tgtgtgtatg gcttcaacgc aatg                                         24

<210> SEQ ID NO 6
<211> LENGTH: 24
<212> TYPE: DNA
<213> ORGANISM: Drosophila melanogaster

<400> SEQUENCE: 6
cactcaacag tctttccagc aggg                                         24

<210> SEQ ID NO 7
<211> LENGTH: 20
<212> TYPE: DNA
<213> ORGANISM: Drosophila melanogaster

<400> SEQUENCE: 7
ggccgtccag gttcaaaaac                                              20

<210> SEQ ID NO 8
<211> LENGTH: 20
<212> TYPE: DNA
<213> ORGANISM: Drosophila melanogaster

<400> SEQUENCE: 8
aatccggcga tagttccgtc                                              20

<210> SEQ ID NO 9
<211> LENGTH: 20
<212> TYPE: DNA
<213> ORGANISM: Drosophila melanogaster

<400> SEQUENCE: 9
gagtcgtgtg ctcaagtcca                                              20

<210> SEQ ID NO 10
<211> LENGTH: 20
<212> TYPE: DNA
<213> ORGANISM: Drosophila melanogaster

<400> SEQUENCE: 10
tgcatcacaa aacacaggcg                                              20

<210> SEQ ID NO 11
<211> LENGTH: 20
<212> TYPE: DNA
<213> ORGANISM: Drosophila melanogaster

```
<400> SEQUENCE: 11
tcgccgaact cagtaaccac                                          20

<210> SEQ ID NO 12
<211> LENGTH: 21
<212> TYPE: DNA
<213> ORGANISM: Drosophila melanogaster

<400> SEQUENCE: 12
tcctatcaaa gtagaggcgc a                                        21

<210> SEQ ID NO 13
<211> LENGTH: 21
<212> TYPE: DNA
<213> ORGANISM: Drosophila melanogaster

<400> SEQUENCE: 13
ttagtcagct gcaggcaaag g                                        21

<210> SEQ ID NO 14
<211> LENGTH: 19
<212> TYPE: DNA
<213> ORGANISM: Drosophila melanogaster

<400> SEQUENCE: 14
cggaagctaa cgccacaca                                           19

<210> SEQ ID NO 15
<211> LENGTH: 22
<212> TYPE: DNA
<213> ORGANISM: Drosophila melanogaster

<400> SEQUENCE: 15
caacaagccg aacccagatc tt                                       22

<210> SEQ ID NO 16
<211> LENGTH: 22
<212> TYPE: DNA
<213> ORGANISM: Drosophila melanogaster

<400> SEQUENCE: 16
caaaggagtt caggccgatg at                                       22

<210> SEQ ID NO 17
<211> LENGTH: 20
<212> TYPE: DNA
<213> ORGANISM: Drosophila melanogaster

<400> SEQUENCE: 17
cgcccagcga catggatgct                                          20

<210> SEQ ID NO 18
<211> LENGTH: 20
<212> TYPE: DNA
<213> ORGANISM: Drosophila melanogaster

<400> SEQUENCE: 18
gtacatggtg cgacccttca                                          20

<210> SEQ ID NO 19
<211> LENGTH: 20
<212> TYPE: DNA
<213> ORGANISM: Drosophila melanogaster
```

```
<400> SEQUENCE: 19
acttgtagtg ccagttcccg                                                  20

<210> SEQ ID NO 20
<211> LENGTH: 20
<212> TYPE: DNA
<213> ORGANISM: Drosophila melanogaster

<400> SEQUENCE: 20
accagactgc tccacattcg                                                  20

<210> SEQ ID NO 21
<211> LENGTH: 19
<212> TYPE: DNA
<213> ORGANISM: Drosophila melanogaster

<400> SEQUENCE: 21
cagtgtctct cgttgctca                                                   19

<210> SEQ ID NO 22
<211> LENGTH: 20
<212> TYPE: DNA
<213> ORGANISM: Drosophila melanogater

<400> SEQUENCE: 22
aaccgattgc ttcgctctct                                                  20

<210> SEQ ID NO 23
<211> LENGTH: 19
<212> TYPE: DNA
<213> ORGANISM: Drosophila melanogaster

<400> SEQUENCE: 23
ggcagtttgt cgcctgatg                                                   19

<210> SEQ ID NO 24
<211> LENGTH: 23
<212> TYPE: DNA
<213> ORGANISM: Drosophila melanogaster

<400> SEQUENCE: 24
cagactcctg tccaagagct gtt                                              23

<210> SEQ ID NO 25
<211> LENGTH: 23
<212> TYPE: DNA
<213> ORGANISM: Drosophila melanogater

<400> SEQUENCE: 25
agatcgtgaa gaagcgcacc aag                                              23

<210> SEQ ID NO 26
<211> LENGTH: 23
<212> TYPE: DNA
<213> ORGANISM: Drosophila melanogaster

<400> SEQUENCE: 26
caccaggaac ttcttgaatc cgg                                              23

<210> SEQ ID NO 27
<211> LENGTH: 24
<212> TYPE: DNA
```

<213> ORGANISM: Drosophila melanogaster

<400> SEQUENCE: 27
gctgcacgcc aaccacaaga gact                                          24

<210> SEQ ID NO 28
<211> LENGTH: 24
<212> TYPE: DNA
<213> ORGANISM: Drosophila melanogaster

<400> SEQUENCE: 28
cacgcgcagc aggatgtaag gttt                                          24

<210> SEQ ID NO 29
<211> LENGTH: 20
<212> TYPE: DNA
<213> ORGANISM: Drosophila melanogaster

<400> SEQUENCE: 29
tcgaatgcca ataatctgca                                               20

<210> SEQ ID NO 30
<211> LENGTH: 20
<212> TYPE: DNA
<213> ORGANISM: Drosophila melanogaster

<400> SEQUENCE: 30
cgcgatgctg ggactcccac                                               20

<210> SEQ ID NO 31
<211> LENGTH: 19
<212> TYPE: DNA
<213> ORGANISM: Drosophila melanogaster

<400> SEQUENCE: 31
tgggaggcat acgcaaagt                                                19

<210> SEQ ID NO 32
<211> LENGTH: 20
<212> TYPE: DNA
<213> ORGANISM: Drosophila melanogaster

<400> SEQUENCE: 32
caattacgct ccgtggcttg                                               20

<210> SEQ ID NO 33
<211> LENGTH: 20
<212> TYPE: DNA
<213> ORGANISM: Drosophila melanogaster

<400> SEQUENCE: 33
ggcccatgcc aatttattca                                               20

<210> SEQ ID NO 34
<211> LENGTH: 19
<212> TYPE: DNA
<213> ORGANISM: Drosophila melanogaster

<400> SEQUENCE: 34
cattgcgctg gaactcgaa                                                19

<210> SEQ ID NO 35
<211> LENGTH: 19

<212> TYPE: DNA
<213> ORGANISM: Drosophila melanogaster

<400> SEQUENCE: 35
aggtgtggac cagcgacaa                                                        19

<210> SEQ ID NO 36
<211> LENGTH: 22
<212> TYPE: DNA
<213> ORGANISM: Drosophila melanogaster

<400> SEQUENCE: 36
tgctgtccat atcctccatt ca                                                    22

<210> SEQ ID NO 37
<211> LENGTH: 22
<212> TYPE: DNA
<213> ORGANISM: Drosophila melanogaster

<400> SEQUENCE: 37
gcacaatgaa gttcaccatc gt                                                    22

<210> SEQ ID NO 38
<211> LENGTH: 19
<212> TYPE: DNA
<213> ORGANISM: Drosophila melanogaster

<400> SEQUENCE: 38
ccacacccat ggcaaaaac                                                        19

<210> SEQ ID NO 39
<211> LENGTH: 23
<212> TYPE: DNA
<213> ORGANISM: Drosophila melanogaster

<400> SEQUENCE: 39
agcaagcctt tgtccttcat ctc                                                   23

<210> SEQ ID NO 40
<211> LENGTH: 23
<212> TYPE: DNA
<213> ORGANISM: Drosophila melanogaster

<400> SEQUENCE: 40
acaccatact cagcacctcg ttg                                                   23

<210> SEQ ID NO 41
<211> LENGTH: 24
<212> TYPE: DNA
<213> ORGANISM: Drosophila melanogaster

<400> SEQUENCE: 41
tgtgtgtatg gcttcaacgc aatg                                                  24

<210> SEQ ID NO 42
<211> LENGTH: 24
<212> TYPE: DNA
<213> ORGANISM: Drosophila melanogaster

<400> SEQUENCE: 42
cactcaacag tctttccagc aggg                                                  24

<210> SEQ ID NO 43

-continued

```
<211> LENGTH: 19
<212> TYPE: DNA
<213> ORGANISM: Drosophila melanogaster

<400> SEQUENCE: 43
aacagtggcg gattcggtt                                                   19

<210> SEQ ID NO 44
<211> LENGTH: 21
<212> TYPE: DNA
<213> ORGANISM: Drosophila melanogaster

<400> SEQUENCE: 44
tactcggagc attggaggca t                                                21

<210> SEQ ID NO 45
<211> LENGTH: 21
<212> TYPE: DNA
<213> ORGANISM: Drosophila melanogaster

<400> SEQUENCE: 45
ttagtcagct gcaggcaaag g                                                21

<210> SEQ ID NO 46
<211> LENGTH: 19
<212> TYPE: DNA
<213> ORGANISM: Drosophila melanogaster

<400> SEQUENCE: 46
cggaagctaa cgccacaca                                                   19

<210> SEQ ID NO 47
<211> LENGTH: 22
<212> TYPE: DNA
<213> ORGANISM: Drosophila melanogaster

<400> SEQUENCE: 47
caacaagccg aacccagatc tt                                               22

<210> SEQ ID NO 48
<211> LENGTH: 22
<212> TYPE: DNA
<213> ORGANISM: Drosophila melanogaster

<400> SEQUENCE: 48
caaaggagtt caggccgatg at                                               22

<210> SEQ ID NO 49
<211> LENGTH: 20
<212> TYPE: DNA
<213> ORGANISM: Drosophila melanogaster

<400> SEQUENCE: 49
cgcccagcga catggatgct                                                  20

<210> SEQ ID NO 50
<211> LENGTH: 20
<212> TYPE: DNA
<213> ORGANISM: Drosophila melanogaster

<400> SEQUENCE: 50
gtacatggtg cgacccttca                                                  20
```

```
<210> SEQ ID NO 51
<211> LENGTH: 20
<212> TYPE: DNA
<213> ORGANISM: Drosophila melanogaster

<400> SEQUENCE: 51
ggccgtccag gttcaaaaac                                              20

<210> SEQ ID NO 52
<211> LENGTH: 20
<212> TYPE: DNA
<213> ORGANISM: Drosophila melanogaster

<400> SEQUENCE: 52
aatccggcga tagttccgtc                                              20

<210> SEQ ID NO 53
<211> LENGTH: 20
<212> TYPE: DNA
<213> ORGANISM: Drosophila melanogaster

<400> SEQUENCE: 53
gagtcgtgtg ctcaagtcca                                              20

<210> SEQ ID NO 54
<211> LENGTH: 19
<212> TYPE: DNA
<213> ORGANISM: Drosophila melanogaster

<400> SEQUENCE: 54
tgcatcacaa acacaggcg                                               19

<210> SEQ ID NO 55
<211> LENGTH: 20
<212> TYPE: DNA
<213> ORGANISM: Drosophila melanogaster

<400> SEQUENCE: 55
tcgccgaact cagtaaccac                                              20

<210> SEQ ID NO 56
<211> LENGTH: 21
<212> TYPE: DNA
<213> ORGANISM: Drosophila melanogaster

<400> SEQUENCE: 56
tcctatcaaa gtagaggcgc a                                            21

<210> SEQ ID NO 57
<211> LENGTH: 19
<212> TYPE: DNA
<213> ORGANISM: Drosophila melanogaster

<400> SEQUENCE: 57
ggcagtttgt cgcctgatg                                               19

<210> SEQ ID NO 58
<211> LENGTH: 23
<212> TYPE: DNA
<213> ORGANISM: Drosophila melanogaster

<400> SEQUENCE: 58
cagactcctg tccaagagct gtt                                          23
```

```
<210> SEQ ID NO 59
<211> LENGTH: 19
<212> TYPE: DNA
<213> ORGANISM: Drosophila melanogaster

<400> SEQUENCE: 59
cagtgtctct cgttgctca                                                  19

<210> SEQ ID NO 60
<211> LENGTH: 20
<212> TYPE: DNA
<213> ORGANISM: Drosophila melanogaster

<400> SEQUENCE: 60
aaccgattgc ttcgctctct                                                 20

<210> SEQ ID NO 61
<211> LENGTH: 20
<212> TYPE: DNA
<213> ORGANISM: Drosophila melanogaster

<400> SEQUENCE: 61
acttgtagtg ccagttcccg                                                 20

<210> SEQ ID NO 62
<211> LENGTH: 20
<212> TYPE: DNA
<213> ORGANISM: Drosophila melanogaster

<400> SEQUENCE: 62
accagactgc tccacattcg                                                 20

<210> SEQ ID NO 63
<211> LENGTH: 23
<212> TYPE: DNA
<213> ORGANISM: Drosophila melanogaster

<400> SEQUENCE: 63
agatcgtgaa gaagcgcacc aag                                             23

<210> SEQ ID NO 64
<211> LENGTH: 24
<212> TYPE: DNA
<213> ORGANISM: Drosophila melanogaster

<400> SEQUENCE: 64
gctgcacgcc aaccacaaga gact                                            24

<210> SEQ ID NO 65
<211> LENGTH: 24
<212> TYPE: DNA
<213> ORGANISM: Drosophila melanogaster

<400> SEQUENCE: 65
cacgcgcagc aggatgtaag gttt                                            24

<210> SEQ ID NO 66
<211> LENGTH: 20
<212> TYPE: DNA
<213> ORGANISM: Drosophila melanogaster

<400> SEQUENCE: 66
tcgaatgcca ataatctgca                                                 20
```

```
<210> SEQ ID NO 67
<211> LENGTH: 20
<212> TYPE: DNA
<213> ORGANISM: Drosophila melanogaster

<400> SEQUENCE: 67
cgcgatgctg ggactcccac                                              20

<210> SEQ ID NO 68
<211> LENGTH: 19
<212> TYPE: DNA
<213> ORGANISM: Drosophila melanogaster

<400> SEQUENCE: 68
tgggaggcat acgcaaagt                                               19

<210> SEQ ID NO 69
<211> LENGTH: 20
<212> TYPE: DNA
<213> ORGANISM: Drosophila melanogaster

<400> SEQUENCE: 69
ggcccatgcc aatttattca                                              20

<210> SEQ ID NO 70
<211> LENGTH: 20
<212> TYPE: DNA
<213> ORGANISM: Drosophila melanogaster

<400> SEQUENCE: 70
caattacgct ccgtggcttg                                              20

<210> SEQ ID NO 71
<211> LENGTH: 19
<212> TYPE: DNA
<213> ORGANISM: Drosophila melanogaster

<400> SEQUENCE: 71
cattgcgctg gaactcgaa                                               19

<210> SEQ ID NO 72
<211> LENGTH: 19
<212> TYPE: DNA
<213> ORGANISM: Drosophila melanogaster

<400> SEQUENCE: 72
aggtgtggac cagcgacaa                                               19

<210> SEQ ID NO 73
<211> LENGTH: 22
<212> TYPE: DNA
<213> ORGANISM: Drosophila melanogaster

<400> SEQUENCE: 73
tgctgtccat atcctccatt ca                                           22

<210> SEQ ID NO 74
<211> LENGTH: 22
<212> TYPE: DNA
<213> ORGANISM: Drosophila melanogaster

<400> SEQUENCE: 74
```

```
gcacaatgaa gttcaccatc gt                                                    22

<210> SEQ ID NO 75
<211> LENGTH: 19
<212> TYPE: DNA
<213> ORGANISM: Drosophila melanogaster

<400> SEQUENCE: 75
ccacacccat ggcaaaaac                                                        19
```